US011872186B2

(12) United States Patent
 Lanigan et al.

(10) Patent No.: US 11,872,186 B2
(45) Date of Patent: Jan. 16, 2024

(54) RESERVOIR DEVICES, METHODS AND SYSTEMS

(71) Applicant: DEKA Products Limited Partnership, Manchester, NH (US)

(72) Inventors: Richard J. Lanigan, Concord, NH (US); Joshua Ferris, Allston, MA (US); Jason A. Demers, Manchester, NH (US); Albert A. LePage, Jr., Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 1146 days.

(21) Appl. No.: 16/432,508

(22) Filed: Jun. 5, 2019

(65) Prior Publication Data

US 2020/0121558 A1  Apr. 23, 2020

Related U.S. Application Data

(60) Provisional application No. 62/680,886, filed on Jun. 5, 2018.

(51) Int. Cl.
 *A61J 1/12* (2006.01)
 *A61M 5/14* (2006.01)
 *A61J 1/14* (2023.01)
 *A61J 1/20* (2006.01)

(52) U.S. Cl.
 CPC .............. *A61J 1/12* (2013.01); *A61J 1/1475* (2013.01); *A61J 1/1481* (2015.05); *A61J 1/2058* (2015.05); *A61M 5/14* (2013.01)

(58) Field of Classification Search
 CPC ..... F16K 27/065; A61J 1/1475; A61J 1/2058; A61J 1/1418; A61J 1/12; A61M 2209/045; A61M 2005/3114; A61M 39/223; A61M 2039/229; A61M 5/14; A61M 5/148
 See application file for complete search history.

(56) References Cited

U.S. PATENT DOCUMENTS

| | | | |
|---|---|---|---|
| 4,675,020 A | * | 6/1987 | McPhee ................ A61J 1/2089 604/414 |
| 7,306,578 B2 | | 12/2007 | Gray et al. |
| 8,262,616 B2 | | 9/2012 | Grant et al. |
| 8,414,522 B2 | | 4/2013 | Kamen et al. |

(Continued)

FOREIGN PATENT DOCUMENTS

| | | |
|---|---|---|
| EP | 3017804 | 11/2016 |
| WO | 2015195844 | 12/2015 |

(Continued)

OTHER PUBLICATIONS

International Search Report and Written Opinion dated Aug. 30, 2019, issued in International Patent Application PCT/US2019/035596, 9 pages.

(Continued)

*Primary Examiner* — Ariana Zimbouski
(74) *Attorney, Agent, or Firm* — Reid Knott Cunningham

(57) ABSTRACT

A reservoir assembly is disclosed. The reservoir assembly includes a reservoir; a port connector comprising: an inlet extending from an interior volume of the reservoir; an outlet wherein fluid contained in the interior volume of the reservoir exits the reservoir; and a filling port configured wherein the reservoir may be filled with a fluid.

21 Claims, 71 Drawing Sheets

(56) References Cited

U.S. PATENT DOCUMENTS

| | | | |
|---|---|---|---|
| 8,491,570 B2 | 7/2013 | Kamen et al. | |
| 9,617,020 B2 | 4/2017 | Lanigan et al. | |
| 2007/0119508 A1* | 5/2007 | West | F16K 11/085 |
| | | | 137/625.47 |
| 2008/0262465 A1* | 10/2008 | Zinger | A61J 1/1412 |
| | | | 604/411 |
| 2010/0168664 A1* | 7/2010 | Zinger | A61J 1/2096 |
| | | | 604/89 |
| 2014/0107579 A1 | 4/2014 | Lanigan et al. | |
| 2015/0281863 A1 | 10/2015 | Westergaard et al. | |
| 2017/0020784 A1* | 1/2017 | Schweiss | A61M 5/1407 |
| 2017/0340517 A1* | 11/2017 | Ding | A61J 1/1475 |
| 2018/0117297 A1 | 5/2018 | Allard | |
| 2019/0201624 A1 | 7/2019 | Weibel et al. | |

FOREIGN PATENT DOCUMENTS

| | | |
|---|---|---|
| WO | 2016166346 | 10/2016 |
| WO | 2017211850 | 12/2017 |
| WO | 2019032934 | 2/2019 |

OTHER PUBLICATIONS

International Preliminary Report on Patentability dated Dec. 8, 2020, issued in International Patent Application PCT/US2019/035596, 6 pages.
Communication pursuant to Rules 161(1) and 162 EPC dated Feb. 4, 2021, issued in European Patent Application No. 19733287.7, 3 pages.
U.S. Appl. No. 62/597,246, filed Dec. 11, 2017.

* cited by examiner

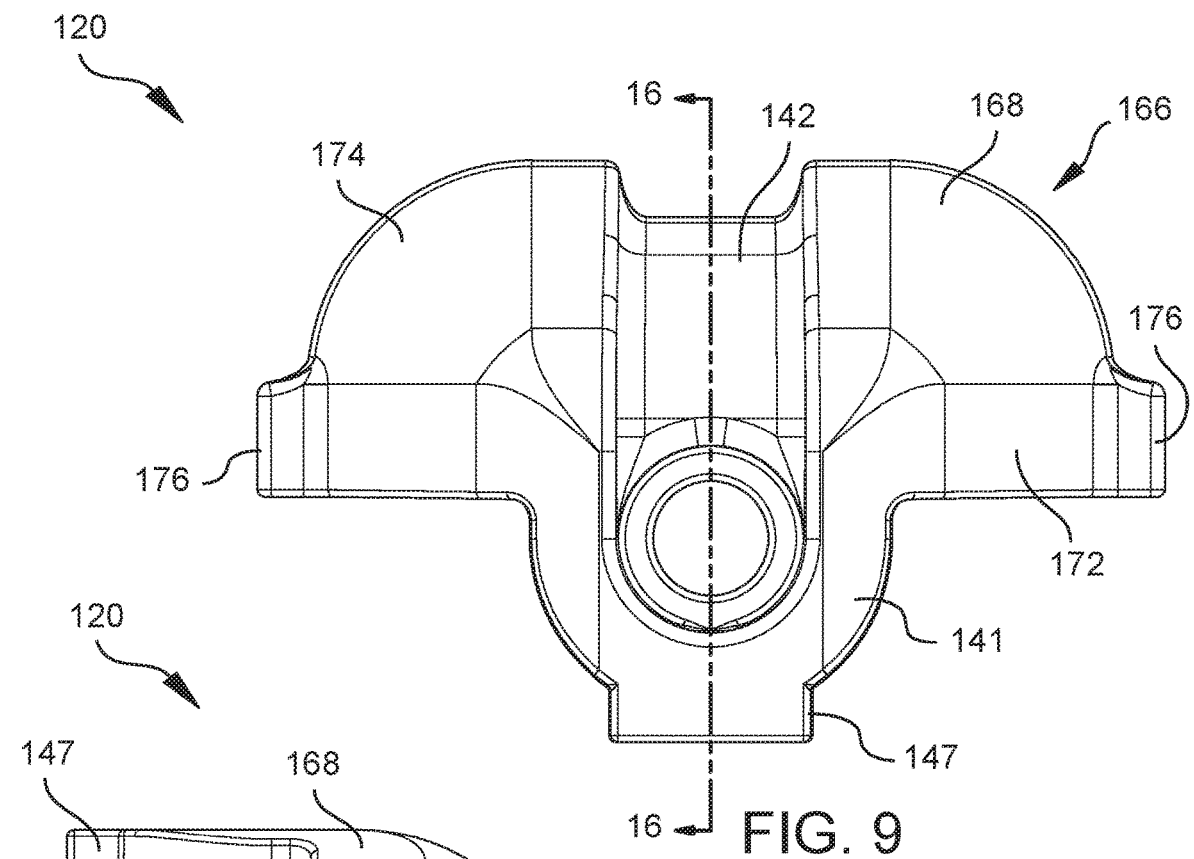
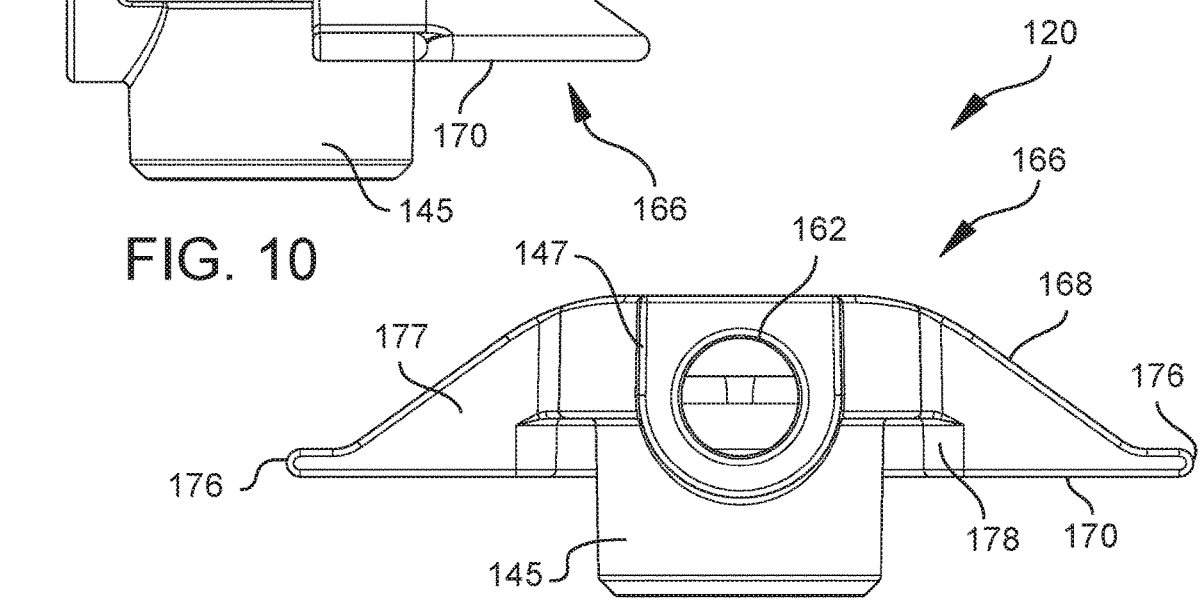

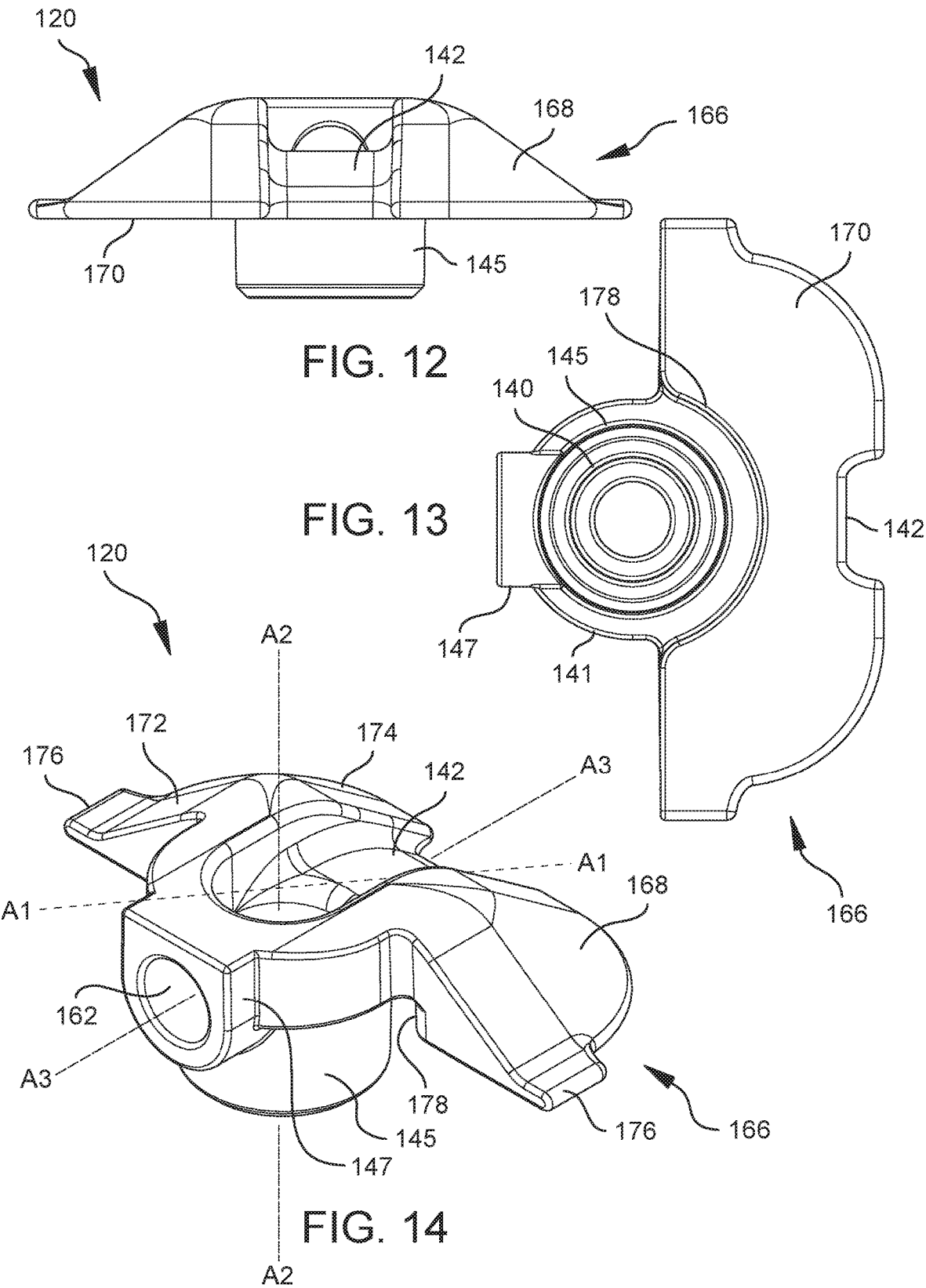

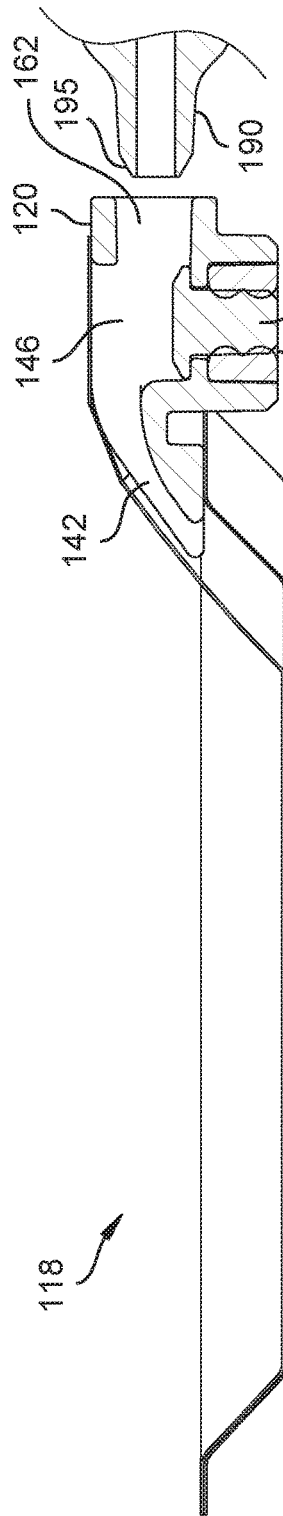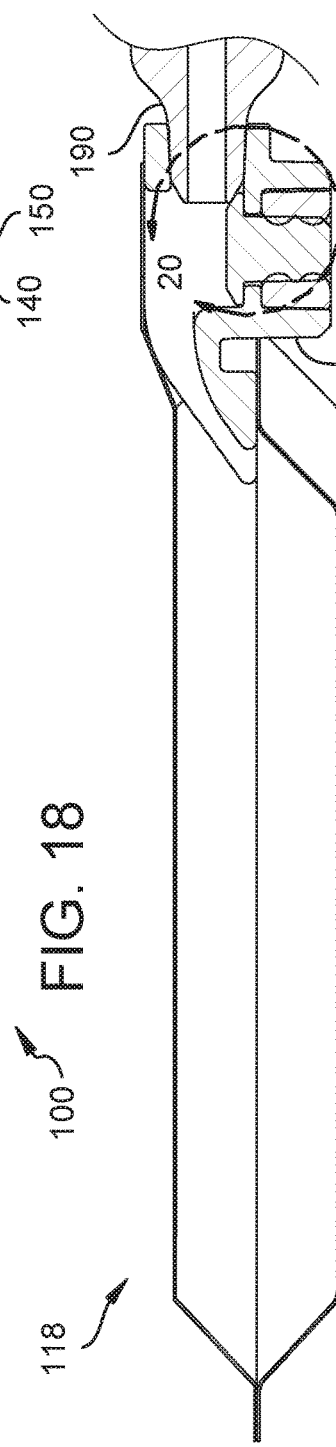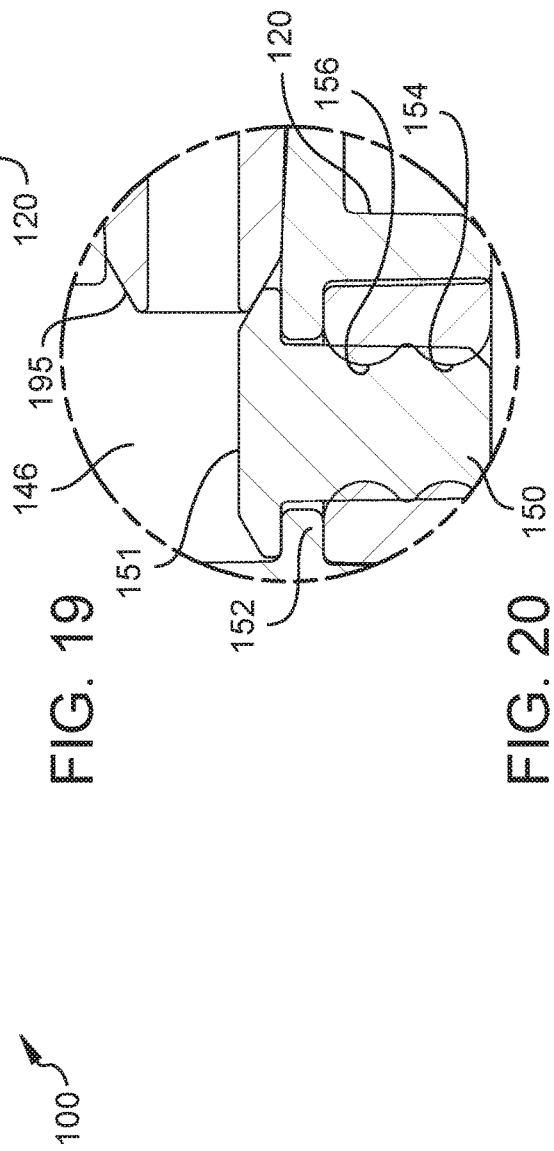

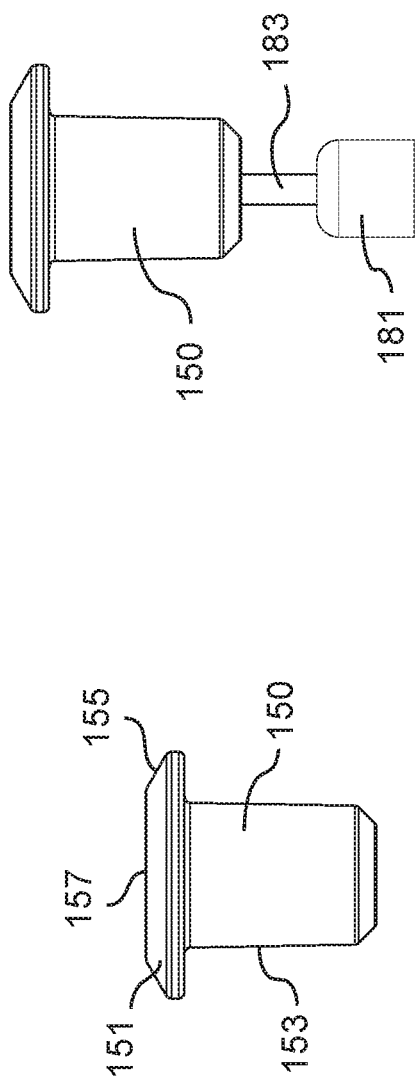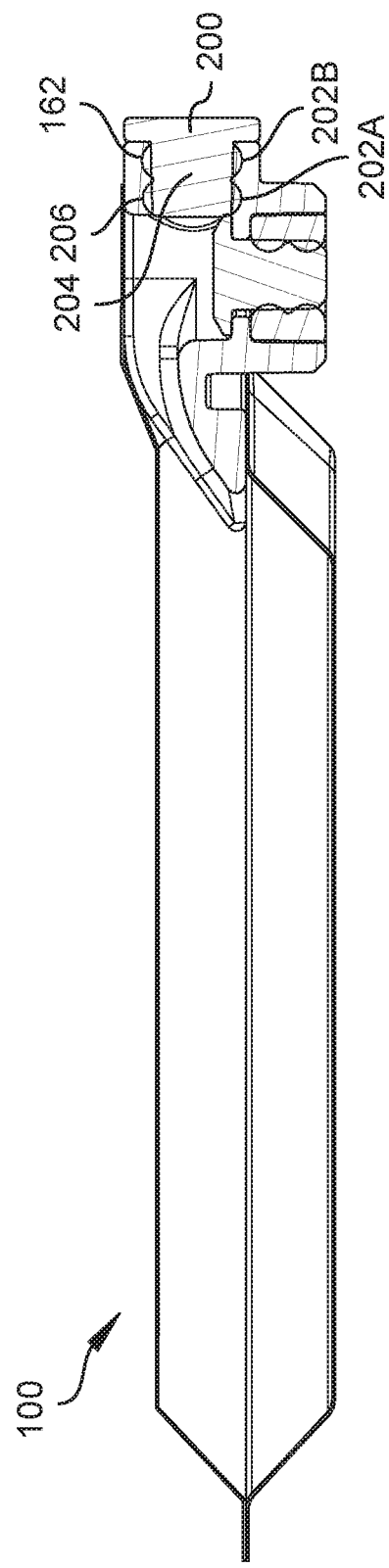

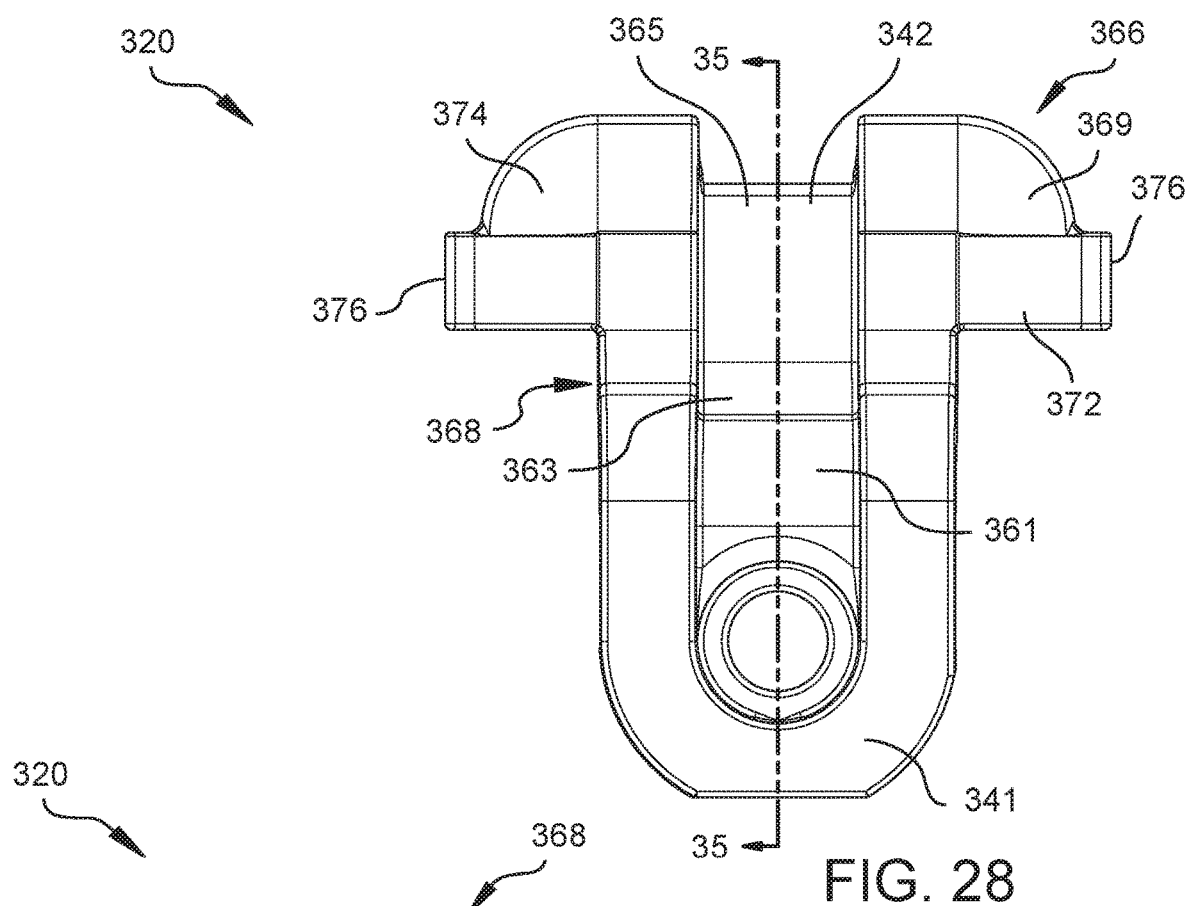
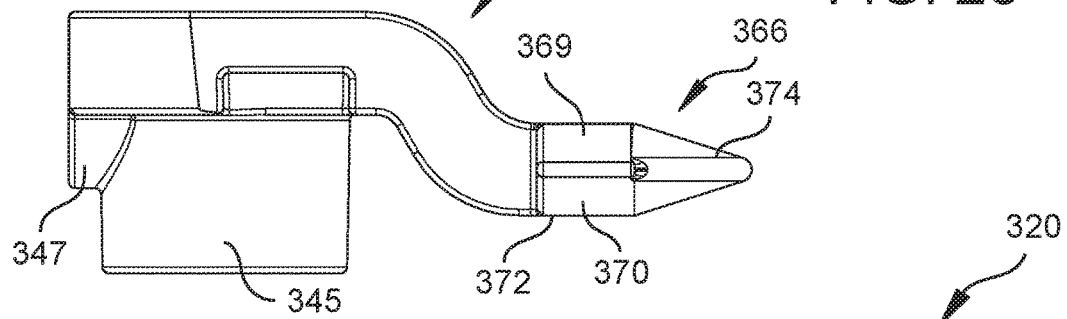
FIG. 29
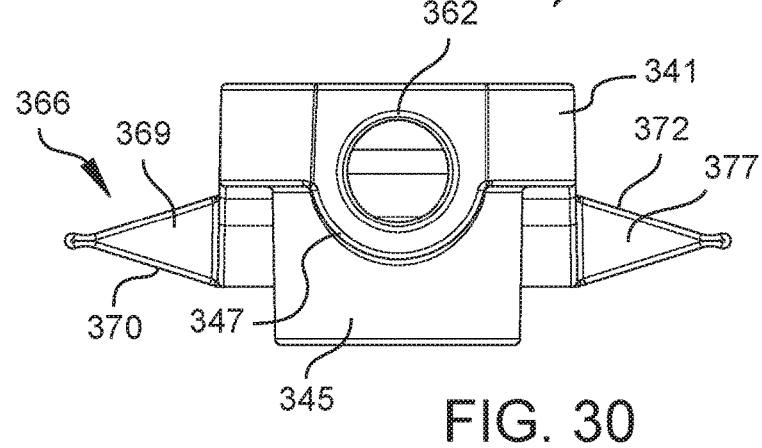

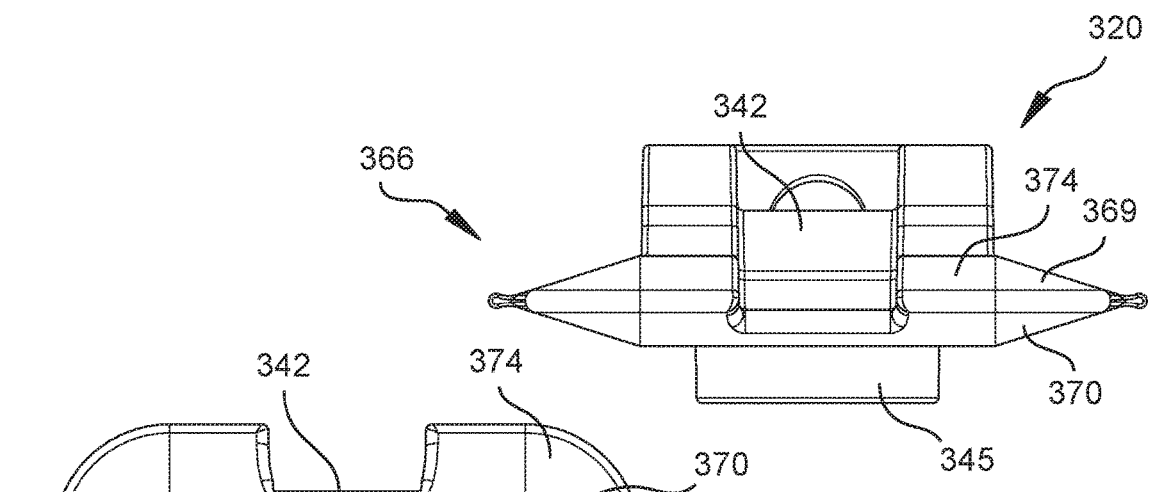
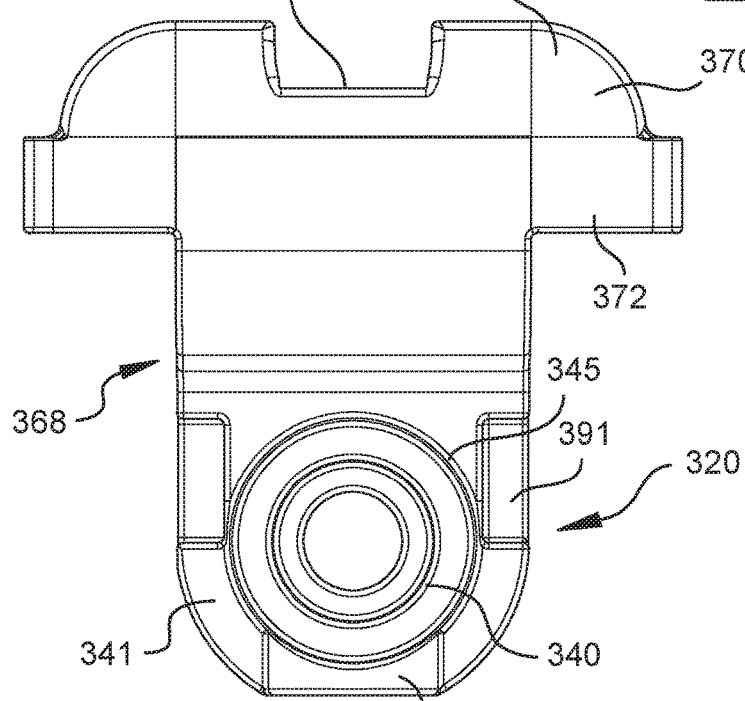
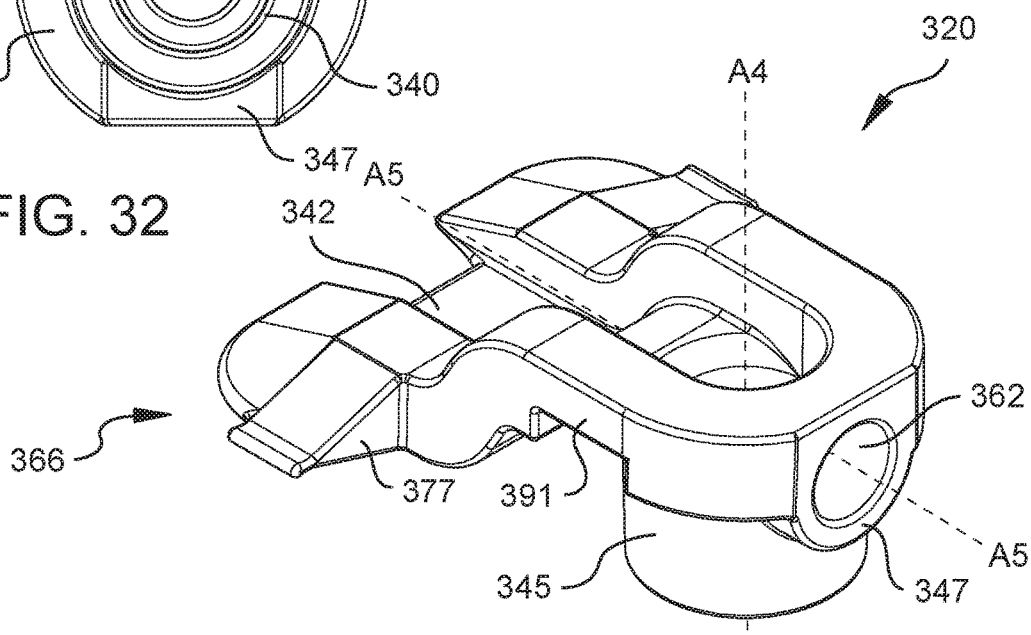

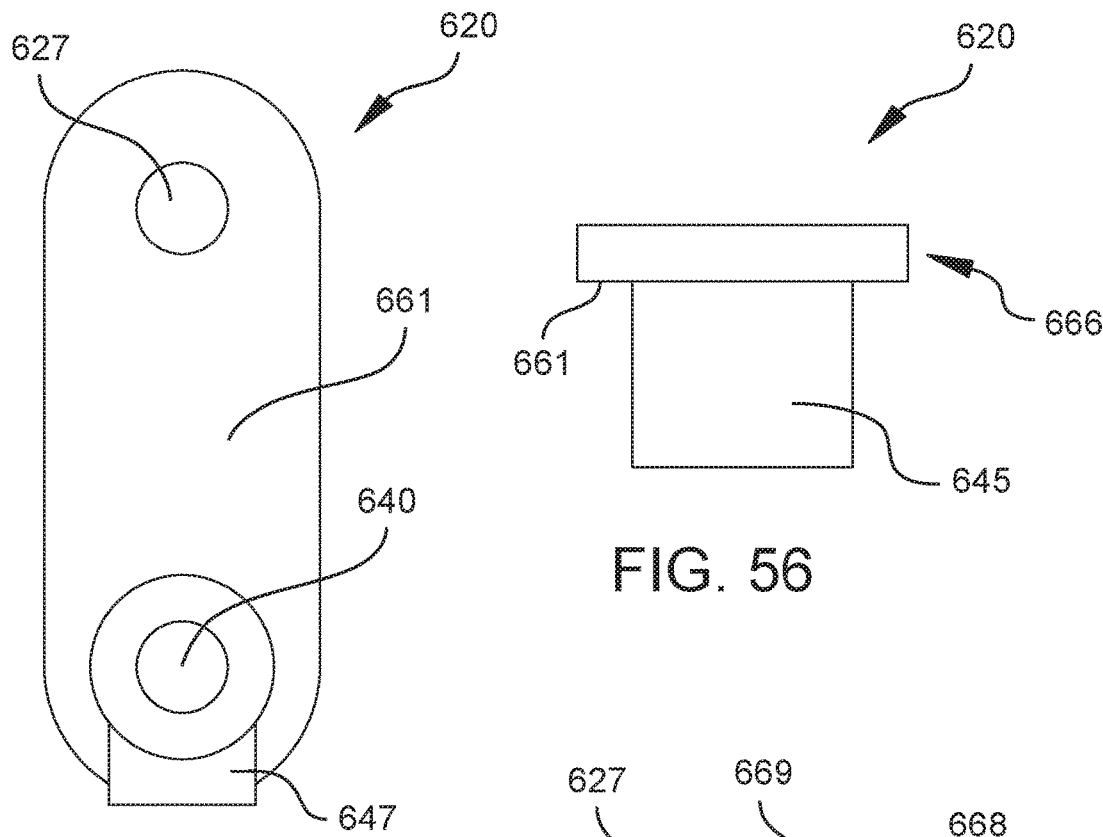
FIG. 55
FIG. 56
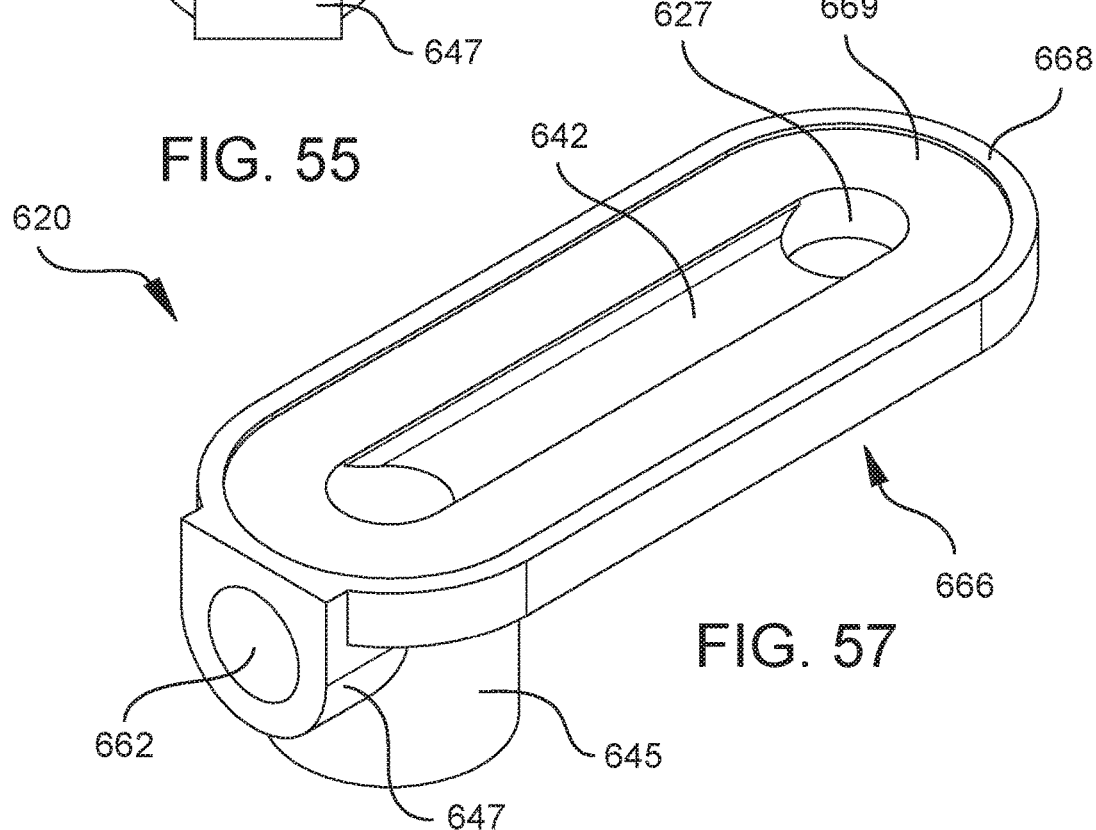
FIG. 57

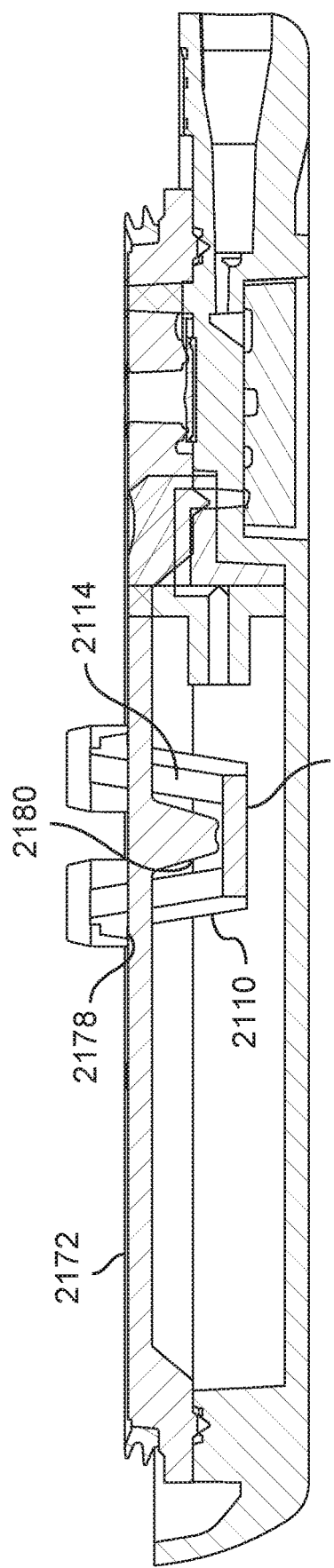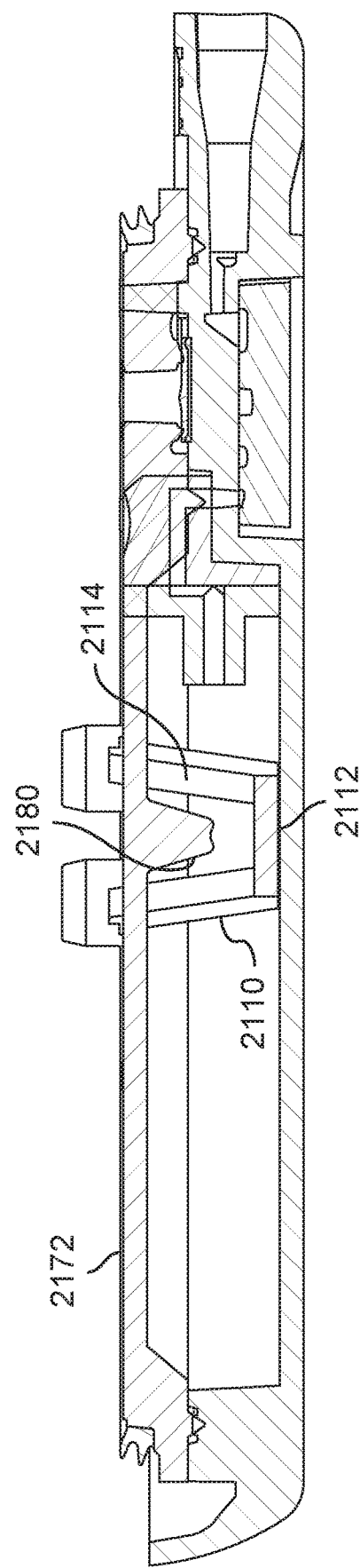

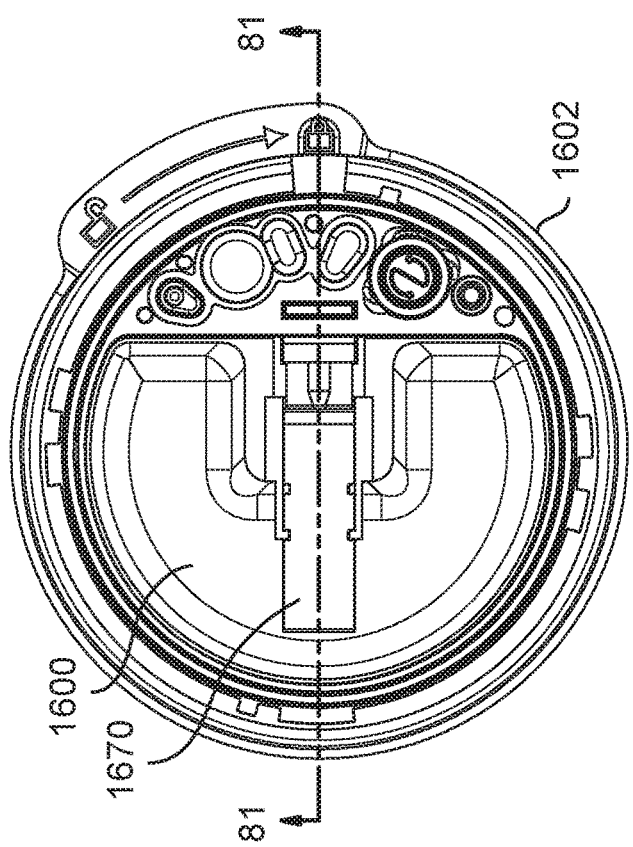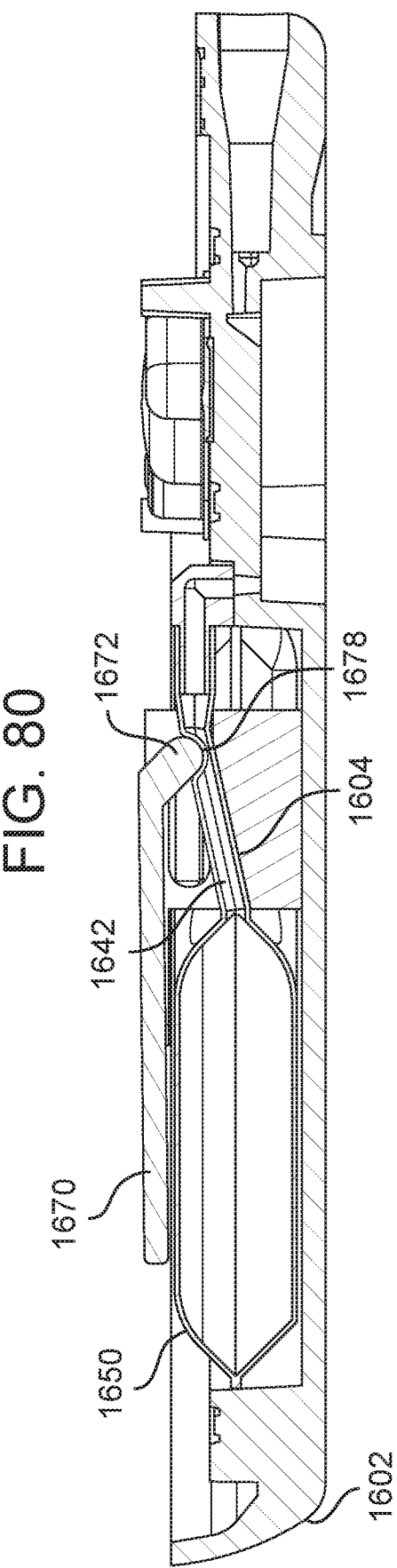

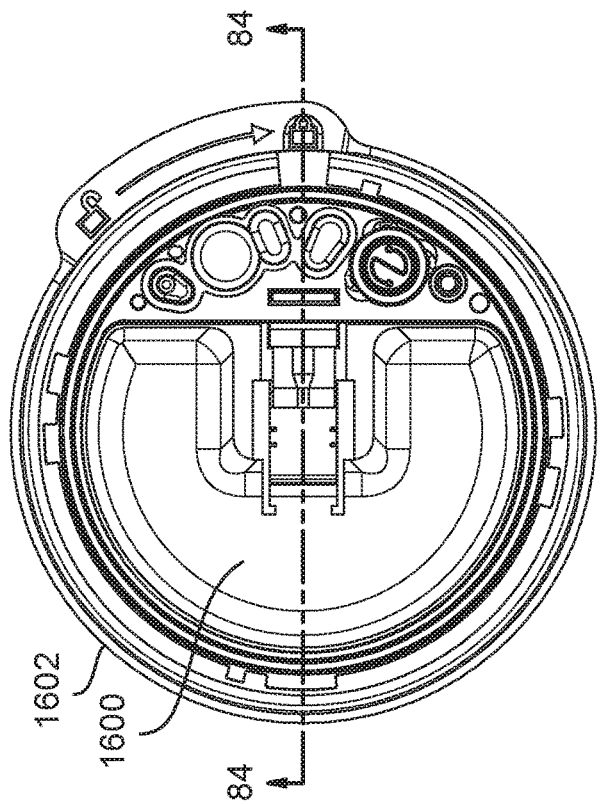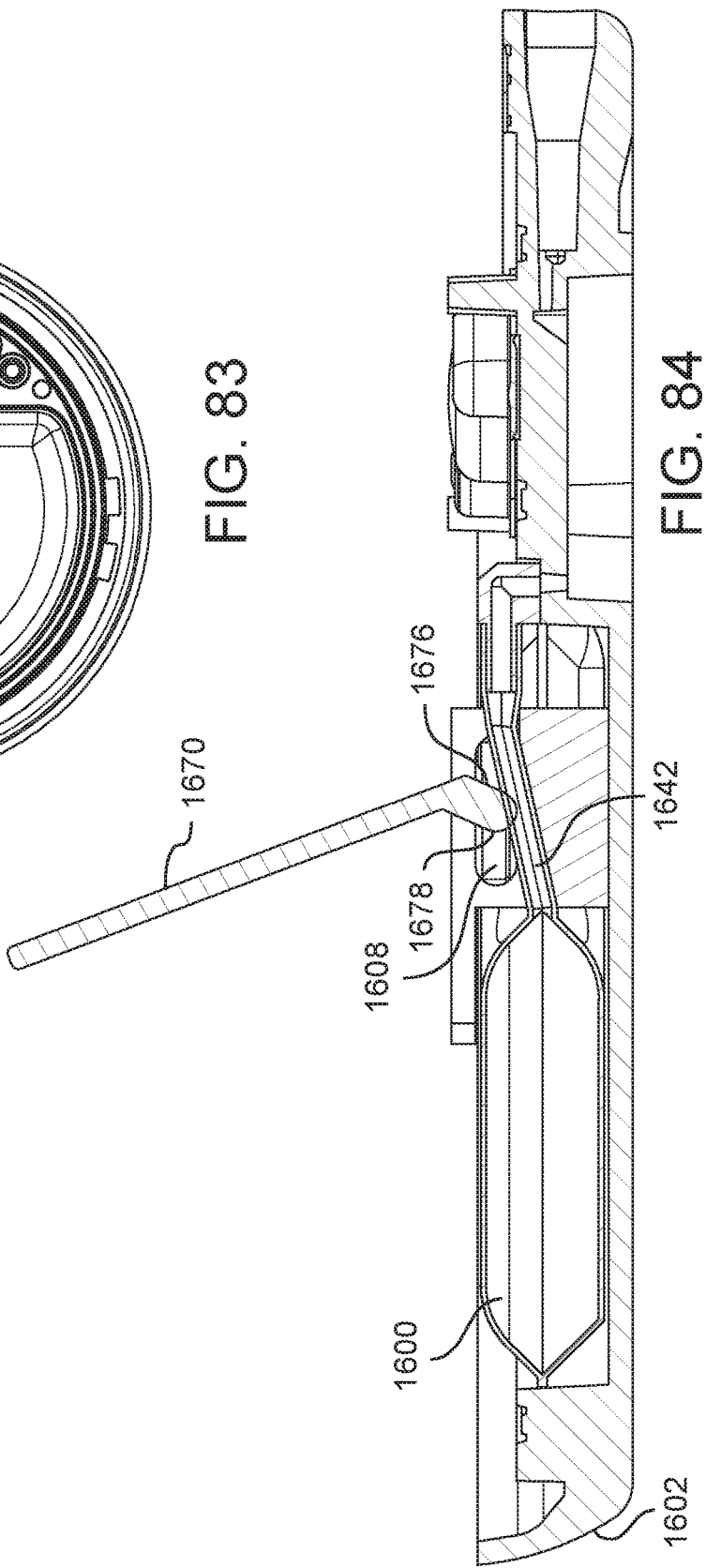

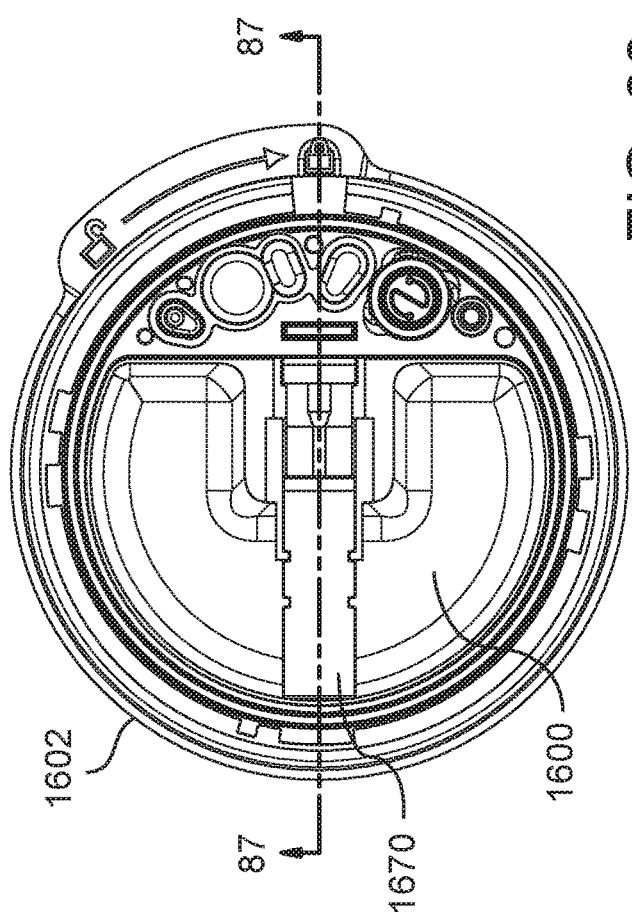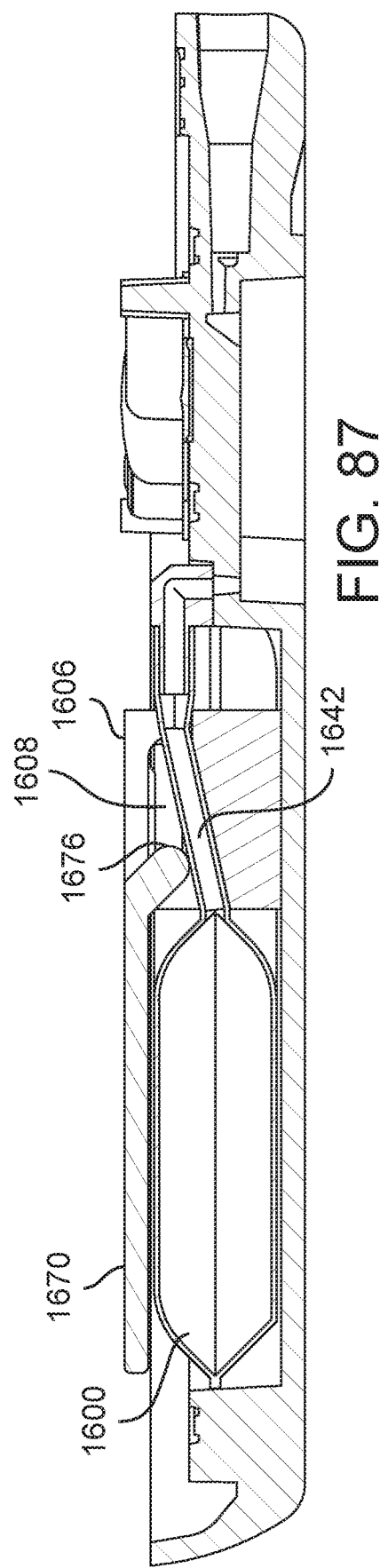

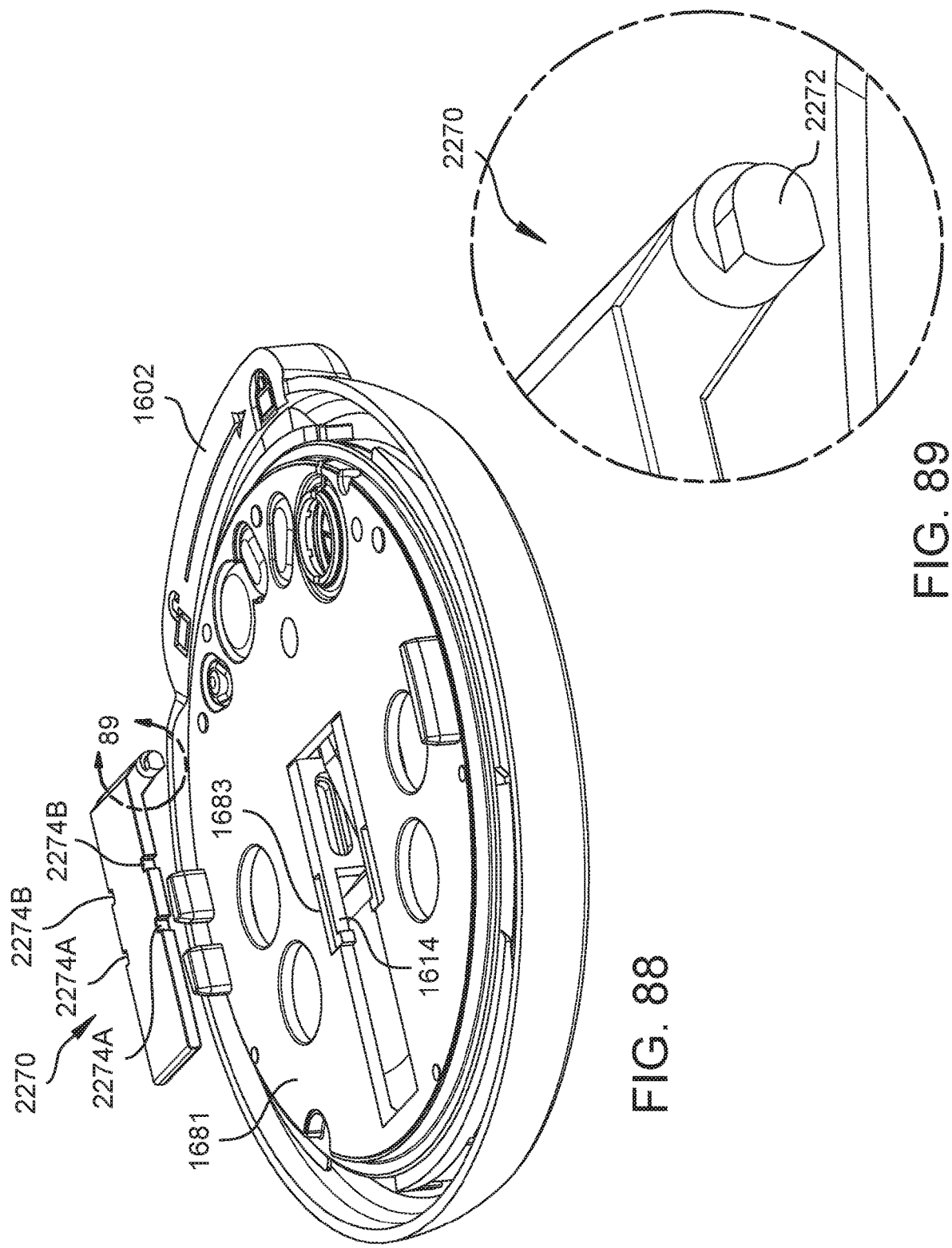

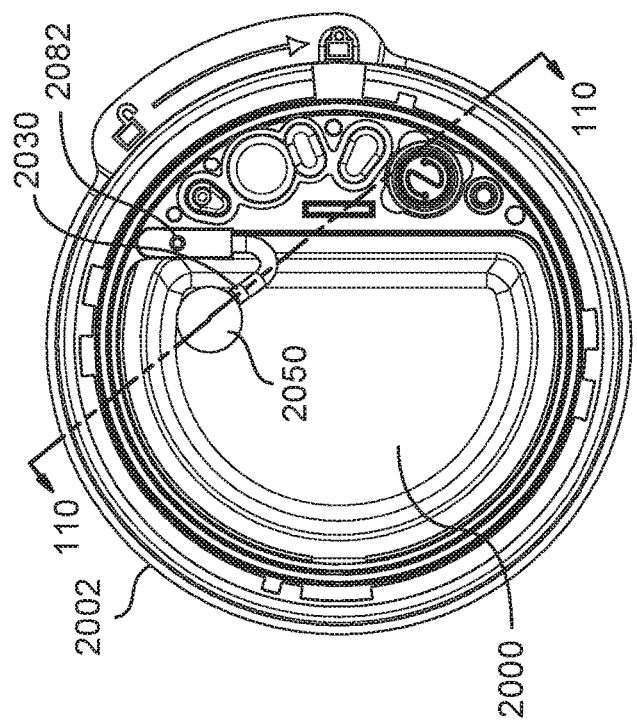
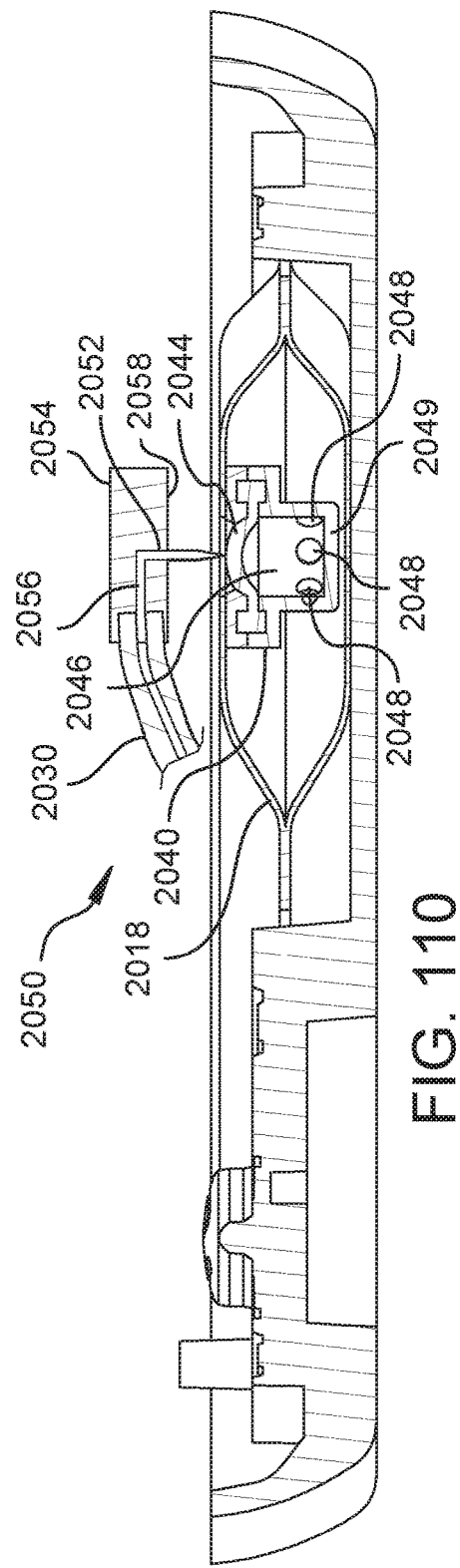

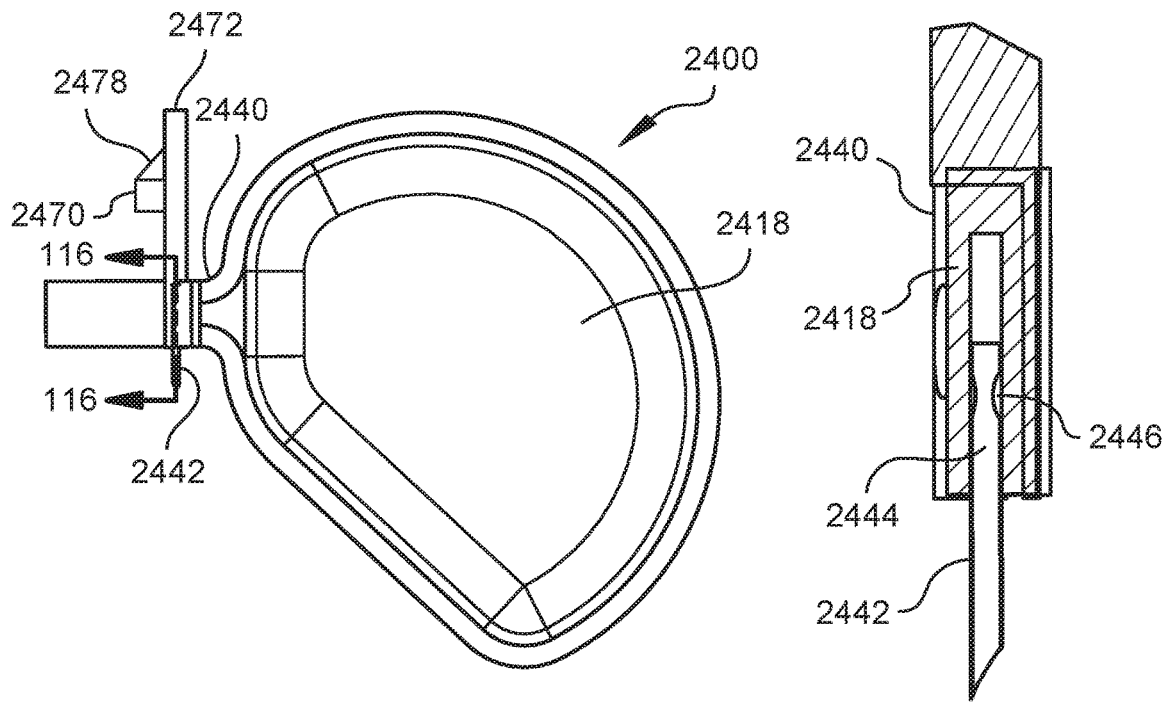
FIG. 113
FIG. 116
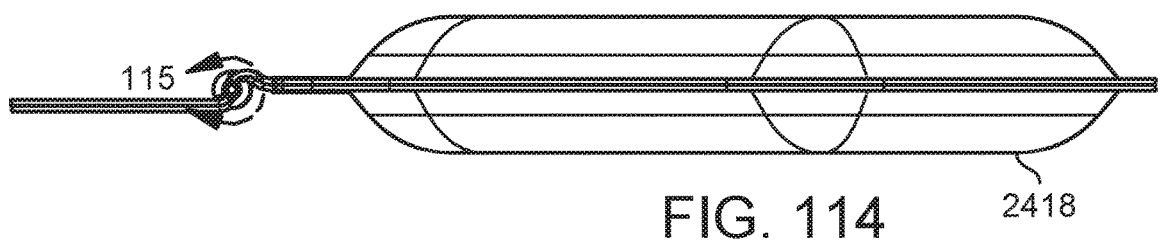
FIG. 114
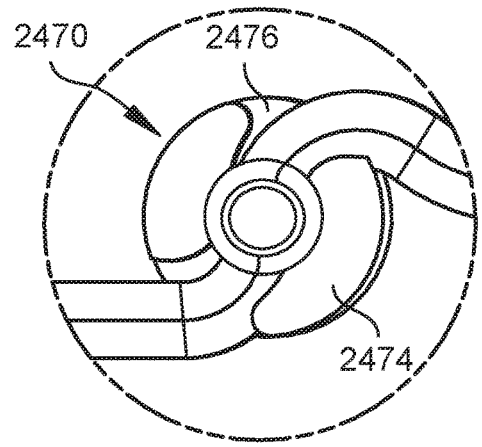
FIG. 115

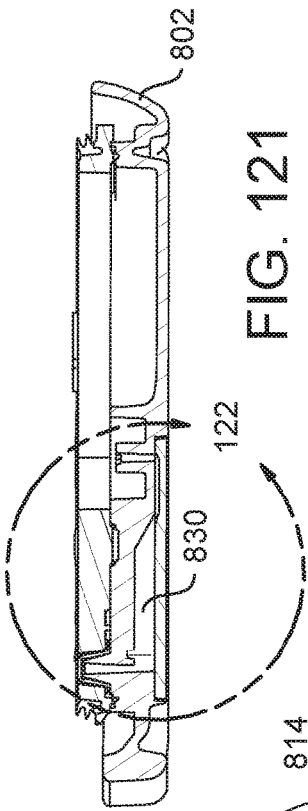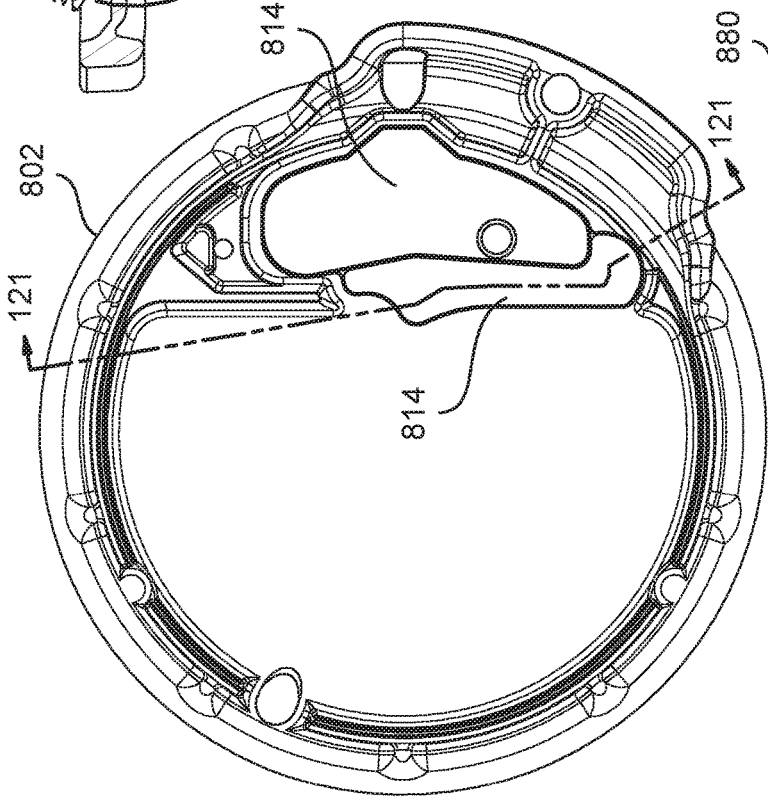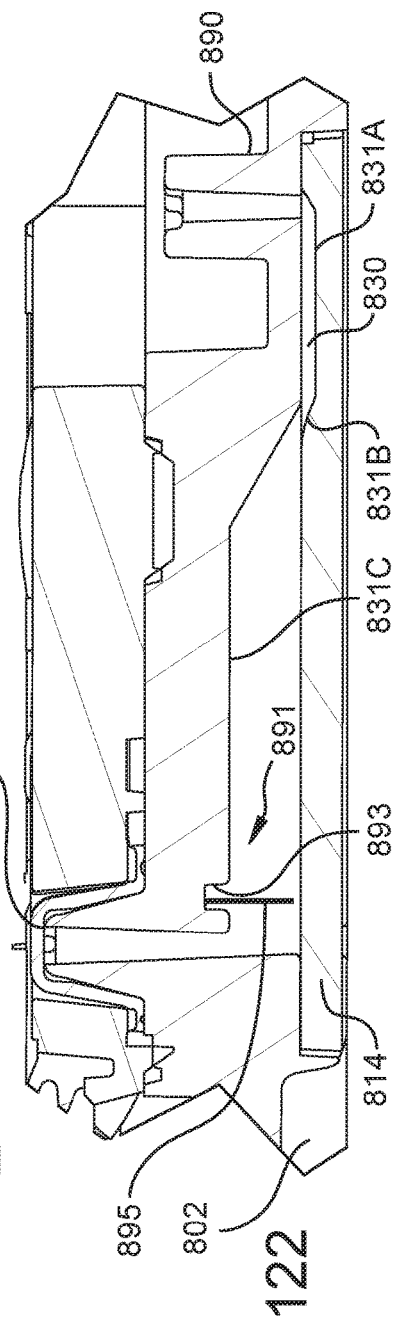

RESERVOIR DEVICES, METHODS AND SYSTEMS

CROSS REFERENCE TO RELATED APPLICATION(S)

The present application is a Non-Provisional application which claims priority from U.S. Provisional Patent Application Ser. No. 62/680,886, filed Jun. 5, 2018 and entitled Reservoir Devices, Methods and Systems, which is hereby incorporated herein by reference in its entirety.

TECHNICAL FIELD

This disclosure relates to containers that may be filled with parenteral medications and other substances.

BACKGROUND INFORMATION

Many potentially valuable medicines or compounds, including biologics, are not orally active due to poor absorption, hepatic metabolism or other pharmacokinetic factors. Additionally, some therapeutic compounds, although they can be orally absorbed, are dosed with a frequency making it difficult or impossible for a patient to maintain the desired schedule using an oral formulation. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight, and cost of these devices is also an ongoing challenge. Additionally, these devices often apply to the skin and pose the challenge of frequent re-location for application.

SUMMARY

In accordance with one aspect of the present invention, a reservoir assembly is disclosed. The reservoir assembly includes a reservoir; a port connector comprising: an inlet extending from an interior volume of the reservoir; an outlet wherein fluid contained in the interior volume of the reservoir exits the reservoir; and a filling port configured wherein the reservoir may be filled with a fluid.

Some embodiments of this aspect of the invention include one or more of the following. Wherein the reservoir is at least partially constructed of a flexible material. Wherein the reservoir is at least partially constructed of a rigid material. Wherein the reservoir is at least partially constructed of a flexible material and is at least partially constructed of a rigid material. Wherein the reservoir comprising a perimeter edge comprising at least one contoured segment. Wherein the reservoir comprising a perimeter edge comprising at least one round segment. Wherein the reservoir comprising a perimeter edge comprising at least one arcuate segment. Wherein at least a portion of the at least one contoured segment is defined by the port connector. Wherein at least a section of the port connector is substantially perpendicular to a top and a bottom side formed by the reservoir. Wherein the port connector further comprising a common fluid channel. Wherein the common fluid channel is an intermediary conduit between the inlet and the outlet. Wherein the common fluid channel is an intermediary conduit between the inlet, the outlet, and the filling port. Wherein fluid exiting the reservoir passes from the inlet, through the common fluid channel, and to the outlet. Wherein the port connector further comprising a flange member. Wherein the inlet is defined by a portion of the flange member. Wherein the assembly further includes a common fluid channel connecting the filling port and the inlet. Wherein the port connector further comprising a pin, wherein the pin blocks the outlet and at least partially extends into the common fluid channel. Wherein the pin is displaceable within the port connector. Wherein the pin selectively seals off fluid communications between the inlet and the outlet. Wherein the reservoir assembly further comprising a stopper removably attached to the filling port. Wherein the pin is displaceable between a first position and a second position, the pin sealing the outlet in the first position, at least a portion of the pin in the common fluid channel in the second position. Wherein the port connector is configured to accept a fill nozzle at a first time and the stopper at a second time.

In accordance with one aspect of the present invention, a reservoir assembly is disclosed. The reservoir assembly includes a reservoir; a port connector coupled to the reservoir; and a pin displaceable between a first position and a second position, the pin sealing the outlet in the first position, at least a portion of the pin in a fluid chamber in the second position, wherein the port is configured to accept a fill nozzle at a first time and a plug member, which fluidically seals the port, at a second time.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other aspects will become more apparent from the following detailed description of the various embodiments of the present disclosure with reference to the drawings wherein:

FIG. 9 is a top down view of one embodiment of a port connector;

FIG. 10 is a side view of the port connector of FIG. 9;

FIG. 11 is a front view of the port connector of FIG. 9;

FIG. 12 is a rear view of the port connector of FIG. 9;

FIG. 13 is a bottom up view of the port connector of FIG. 9;

FIG. 14 is a perspective view of the port connector of FIG. 9;

FIG. 18 is a cross sectional view of one embodiment reservoir assembly prior to filling;

FIG. 19 is a cross sectional view of one embodiment of a reservoir assembly in a filled state;

FIG. 20 is a detailed view of the indicated region of FIG. 19;

FIG. 21A is one embodiment of a pin which may be included in a port connector;

FIG. 21B shows one embodiment of a pin with a frangible which may be included in a port connector;

FIG. 22 is a cross sectional view of one embodiment of a reservoir assembly with a plug disposed in its fill port;

FIG. 28 is a top down view of one embodiment of a port connector;

FIG. 29 is a side view of the port connector of FIG. 28;

FIG. 30 is a front view of the port connector of FIG. 28;

FIG. 31 is a rear view of the port connector of FIG. 28;

FIG. 32 is a bottom up view of the port connector of FIG. 28;

FIG. 33 is a perspective view of the port connector of FIG. 28;

FIG. 55 is a bottom up view of the port connector of FIG. 52;

FIG. 56 is a rear view of the port connector of FIG. 52;

FIG. 57 is a perspective view of the port connector of FIG. 52;

FIG. 77 is a cross sectional view taken at line 77-77 of FIG. 75;

FIG. 78 is the cross sectional view of FIG. 77 with the occluder displaced to a non-occluding position;

FIG. 80 is a top down view of one embodiment of a disposable housing assembly, reservoir assembly, and slide type occluder of FIG. 79;

FIG. 81 is a cross sectional view taken at line 81-81 of FIG. 80;

FIG. 83 is a top down view of an embodiment of a disposable housing assembly, reservoir assembly, and slide type occluder shown in FIG. 82;

FIG. 84 is a cross sectional view taken at line 84-84 of FIG. 83;

FIG. 86 is a top down view of one embodiment of the disposable housing assembly, reservoir assembly, and slide type occluder in FIG. 85;

FIG. 87 is a cross section taken at line 87-87 of FIG. 86;

FIG. 88 is a perspective view of one embodiment of a disposable housing assembly with one embodiment of a slide type occluder exploded away;

FIG. 89 is a detailed view of the indicated region of FIG. 88;

FIG. 109 is a top down view of one embodiment of a disposable housing assembly and reservoir of FIG. 108;

FIG. 110 is a cross sectional view taken at line 110-110 of FIG. 109;

FIG. 113 is a top down view of one embodiment of a reservoir assembly and a rod type occluder;

FIG. 114 is a side view of one embodiment of a reservoir assembly and rod type occluder of FIG. 113;

FIG. 115 is a detailed view of the indicated region of FIG. 114;

FIG. 116 is a cross sectional view taken at line 116-116 of FIG. 113;

FIG. 118 is a perspective view of a bottom portion of the example disposable housing assembly of FIG. 117 with a number of cover plates exploded away;

FIG. 119 shows one embodiment of a disposable housing assembly;

FIG. 120 is a bottom up view of one embodiment of a disposable housing assembly of FIG. 117;

FIG. 121 is a cross sectional view take at line 121-121 of FIG. 120;

FIG. 122 is a detailed view of the indicated region of FIG. 121;

FIG. 123 is a perspective view of an example disposable housing assembly, example reservoir assembly and conduit sub assembly, the conduit sub assembly being exploded apart and away from the disposable housing assembly;

FIG. 124 is a top down view of the example disposable housing assembly, example reservoir assembly and conduit sub assembly of FIG. 123;

FIG. 125 is a cross sectional view taken at line 125-125 of FIG. 124;

FIG. 126 is a perspective view of one embodiment of a conduit sub assembly;

FIG. 127 is a top down view of one embodiment of a conduit sub assembly;

FIG. 128 is a side view of one embodiment of a conduit sub assembly of FIG. 127;

FIG. 129 is a front view of one embodiment of a conduit sub assembly of FIG. 127;

Figure 127:
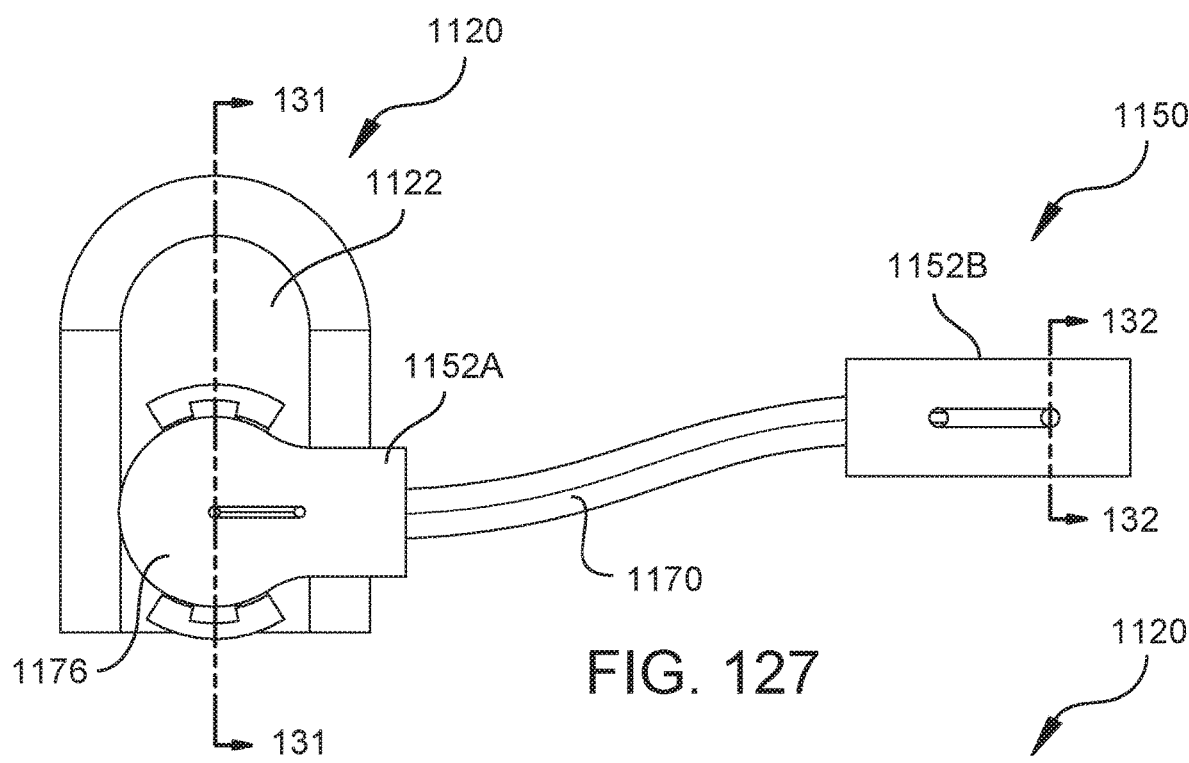
Figure 128:
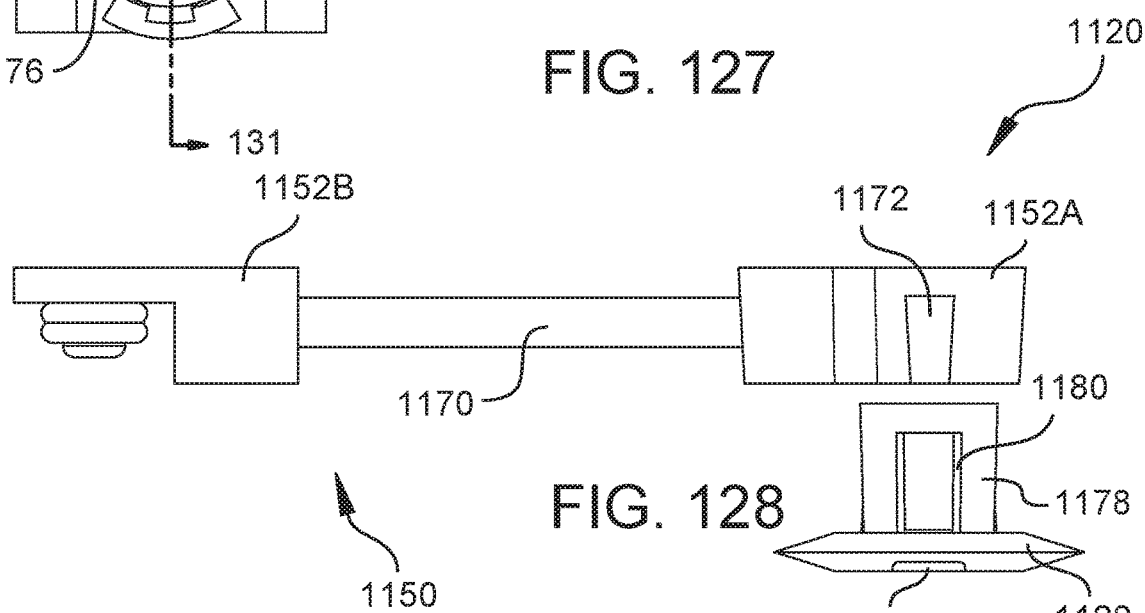
Figure 129:
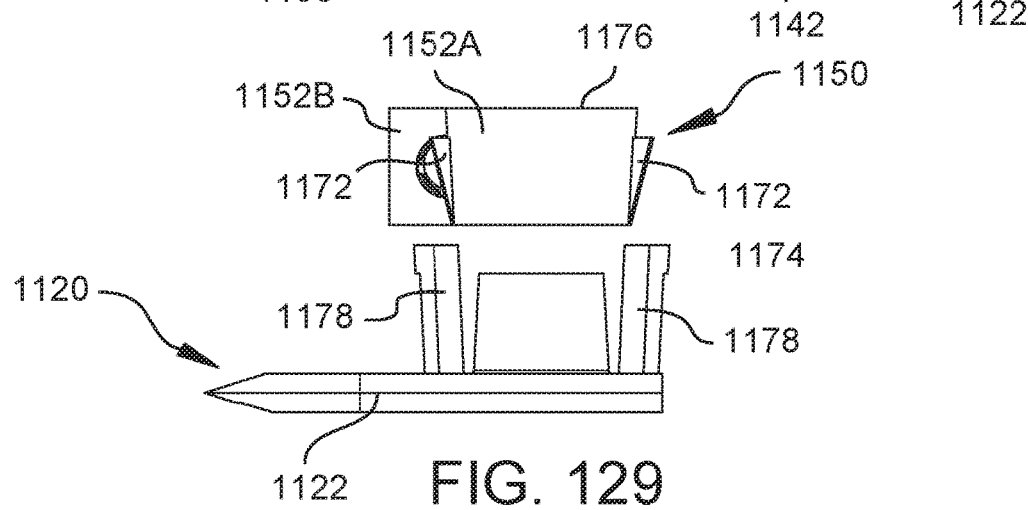
Figure 130:
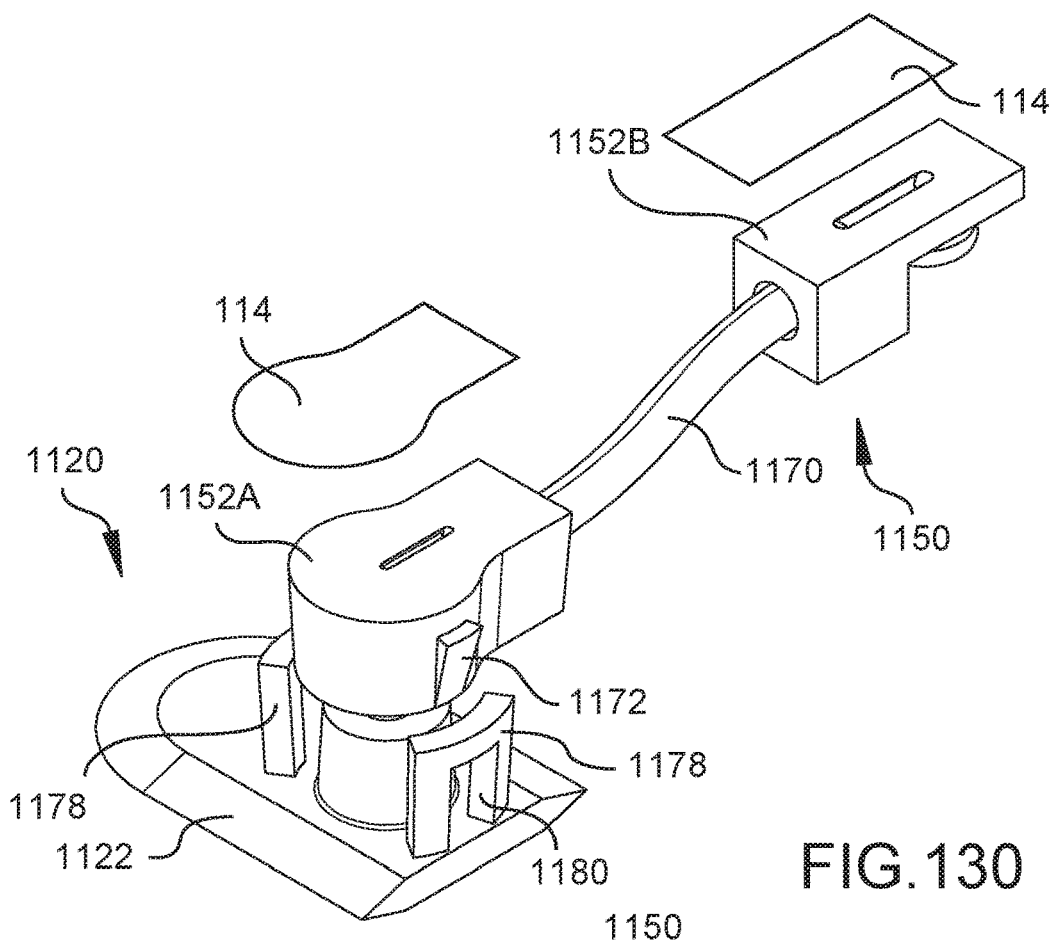
Figure 131:
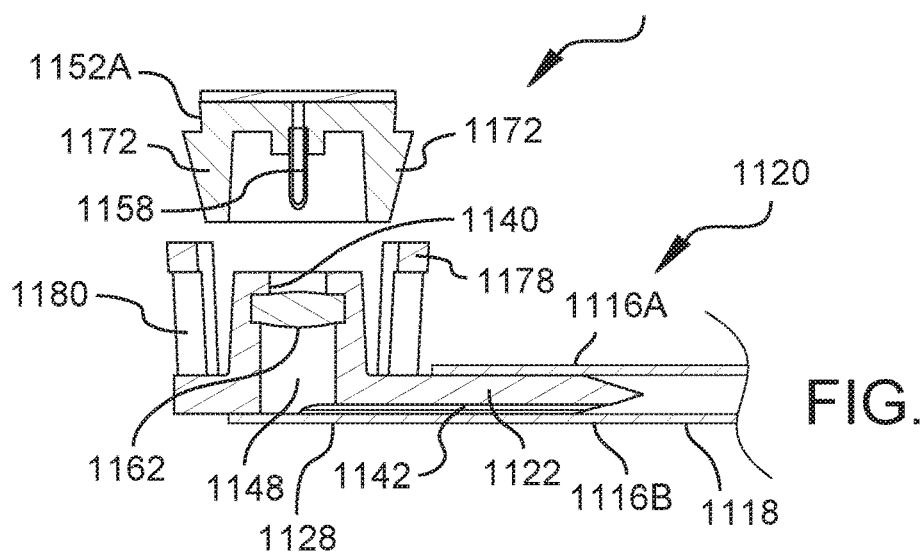

FIG. 130 is a perspective view of one embodiment of a conduit sub assembly of FIG. 127 with cover plates for the conduit sub assembly exploded away from the rest of the conduit sub assembly;

FIG. 131 is a cross section taken at line 131-131 of FIG. 127; and

Figure 132:
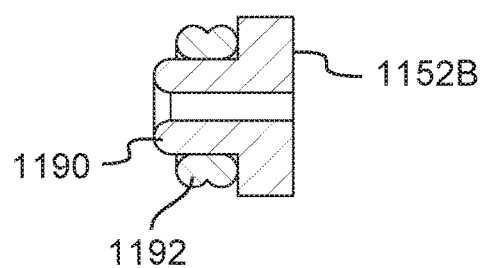

FIG. 132 is a cross section taken at line 132-132 of FIG. 127.

DETAILED DESCRIPTION OF THE EXEMPLARY EMBODIMENTS

Figure 1:
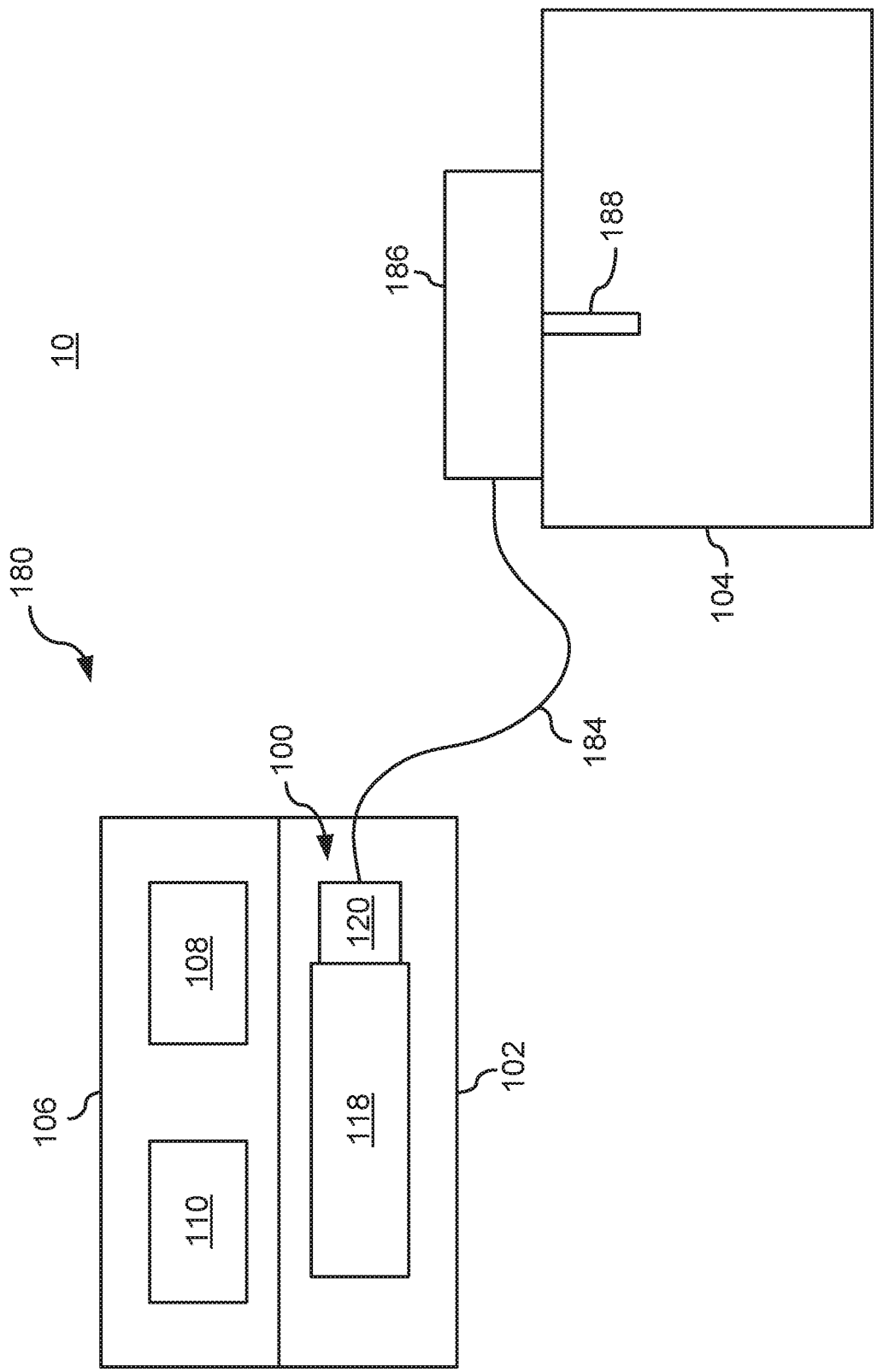
FIG. 1 is a view of an embodiment of a drug delivery system.

Referring to FIG. 1, an exemplary drug delivery system 10 is shown. The example drug delivery system 10 includes a container assembly or reservoir assembly 100 which may be installed within a disposable housing assembly 102. The reservoir assembly 100 may include a container or reservoir 118 and a port connector 120. The disposable housing assembly 102 may be coupled to a reusable housing assembly 106 having controller 108 and a mechanical actuation assembly 110 which may be controlled to selectively dispense fluid from the reservoir assembly 100. As shown, a container assembly 100 may be used in conjunction with an infusion device or infusion base 186 of a drug delivery system 10. The infusion device 186 may be configured to be inserted into a patient to provide a fluid pathway from the reservoir assembly 100 into the patient's skin 104 (e.g. to the subcutaneous layer). To facilitate establishment of a fluid pathway into the patient's skin 104, the infusion device may include a needle or cannula 188. The infusion device 186 may be fluidly connected to a length of tubing 184 and/or to an infusion pump or delivery device 180. A port connector 120 may couple the reservoir assembly 100 directly or indirectly to the tubing 184 or infusion device 186 in certain embodiments.

The various components described in relation to FIG. 1 may be, but are not limited to, those shown and described in one or more of the following: U.S. patent application Ser. No. 13/788,260, filed Mar. 7, 2013 and entitled Infusion Pump Assembly, now U.S. Publication No. US-2014-0107579, published Apr. 17, 2014; U.S. Pat. No. 8,491,570, issued Jul. 23, 2013 and entitled Infusion Pump Assembly; U.S. Pat. No. 8,414,522, issued Apr. 9, 2013 and entitled Fluid Delivery Systems and Methods; U.S. Pat. No. 8,262,616, issued Sep. 11, 2012 and entitled Infusion Pump Assembly; U.S. Pat. No. 7,306,578, issued Dec. 11, 2007 and entitled Loading Mechanism for Infusion Pump; U.S. Provisional Application No. 62/597,246, filed Dec. 11, 2017 and entitled Infusion Pump Assembly and U.S. Publication No. 2015/0281863, published Oct. 5, 2017 and entitled Infusion Set and Inserter Assembly; U.S. application Ser. No. 15/961,238, filed Apr. 24, 2018 and entitled Apparatus, System and Method for Fluid Delivery; and U.S. Pat. No. 9,617,020, issued Apr. 11, 2017 and entitled Apparatus, System and Method for Fluid Delivery, all of which are hereby incorporated herein by reference in their entireties. The systems and methods, including the disposable housing assemblies, reservoirs, filling aids, charging systems, control systems, etc. described in any of the above-referenced applications and patents may also be used in conjunction with the various embodiments described herein, though the embodiments described herein are not limited to use therewith.

Figure 2:
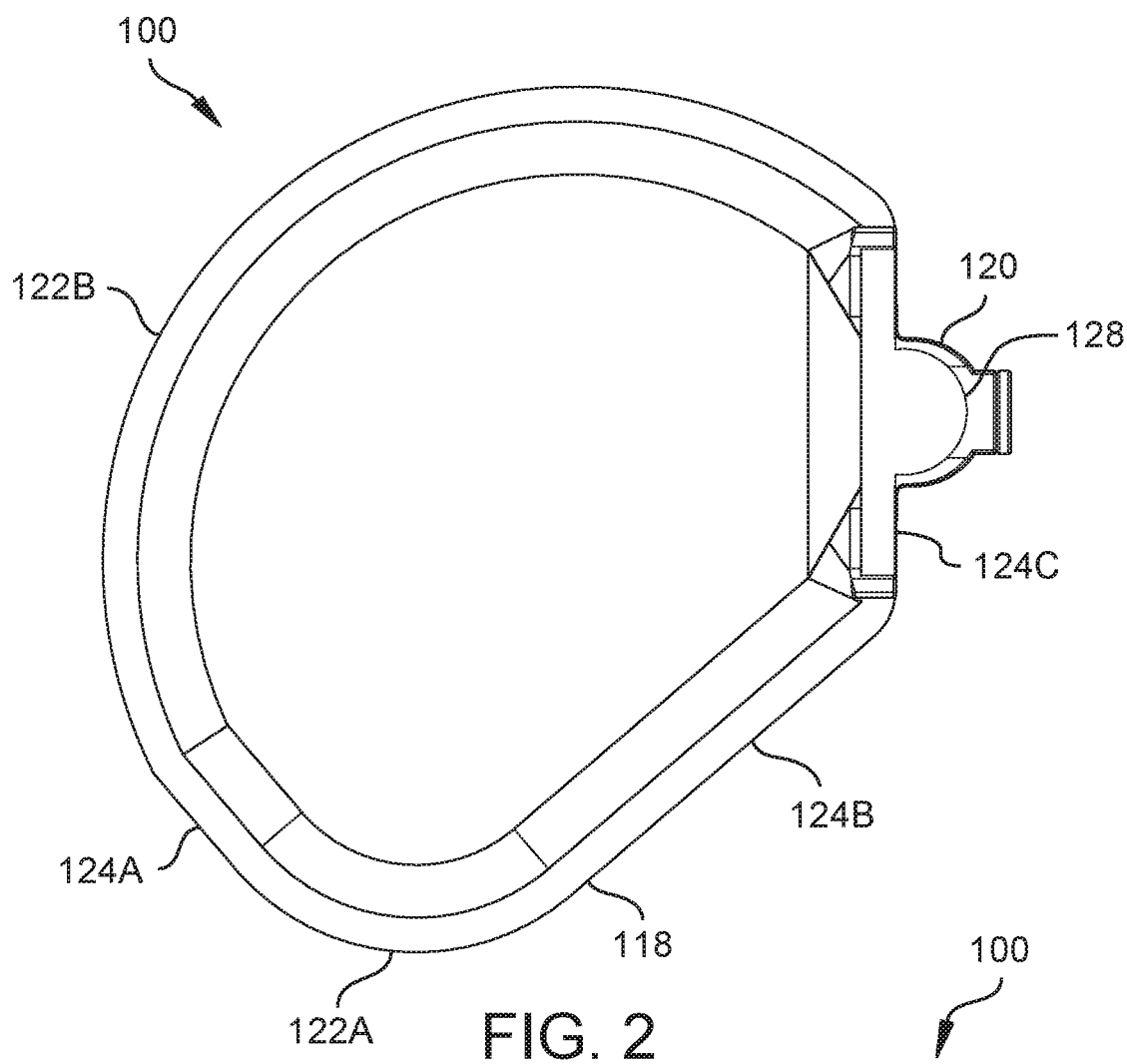
FIG. 2 is a top down view of an embodiment of a reservoir assembly.
Figure 3:
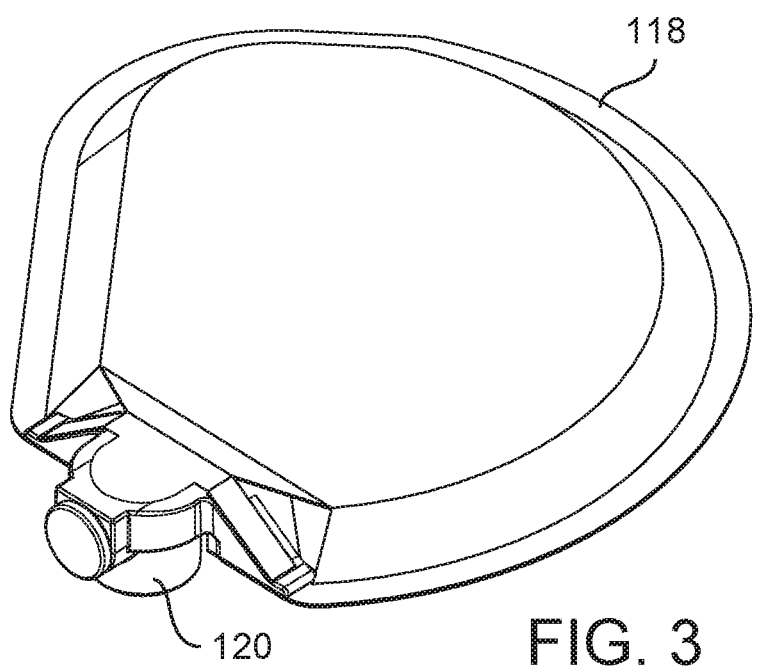
FIG. 3 is a perspective view of the embodiment of a reservoir assembly of FIG. 2.
Figure 4:
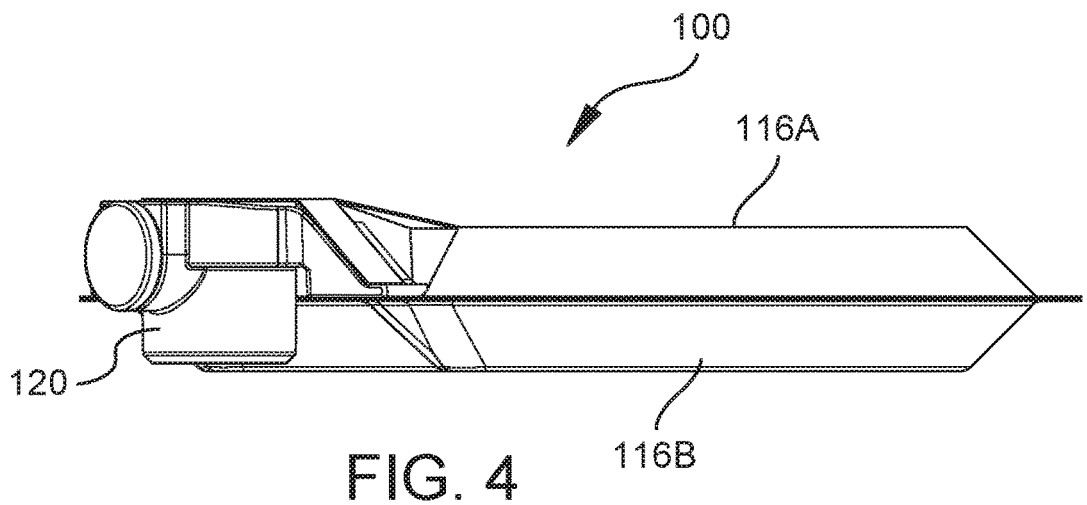
FIG. 4 is a side view of the embodiment of a reservoir assembly of FIG. 2.
Figure 5:
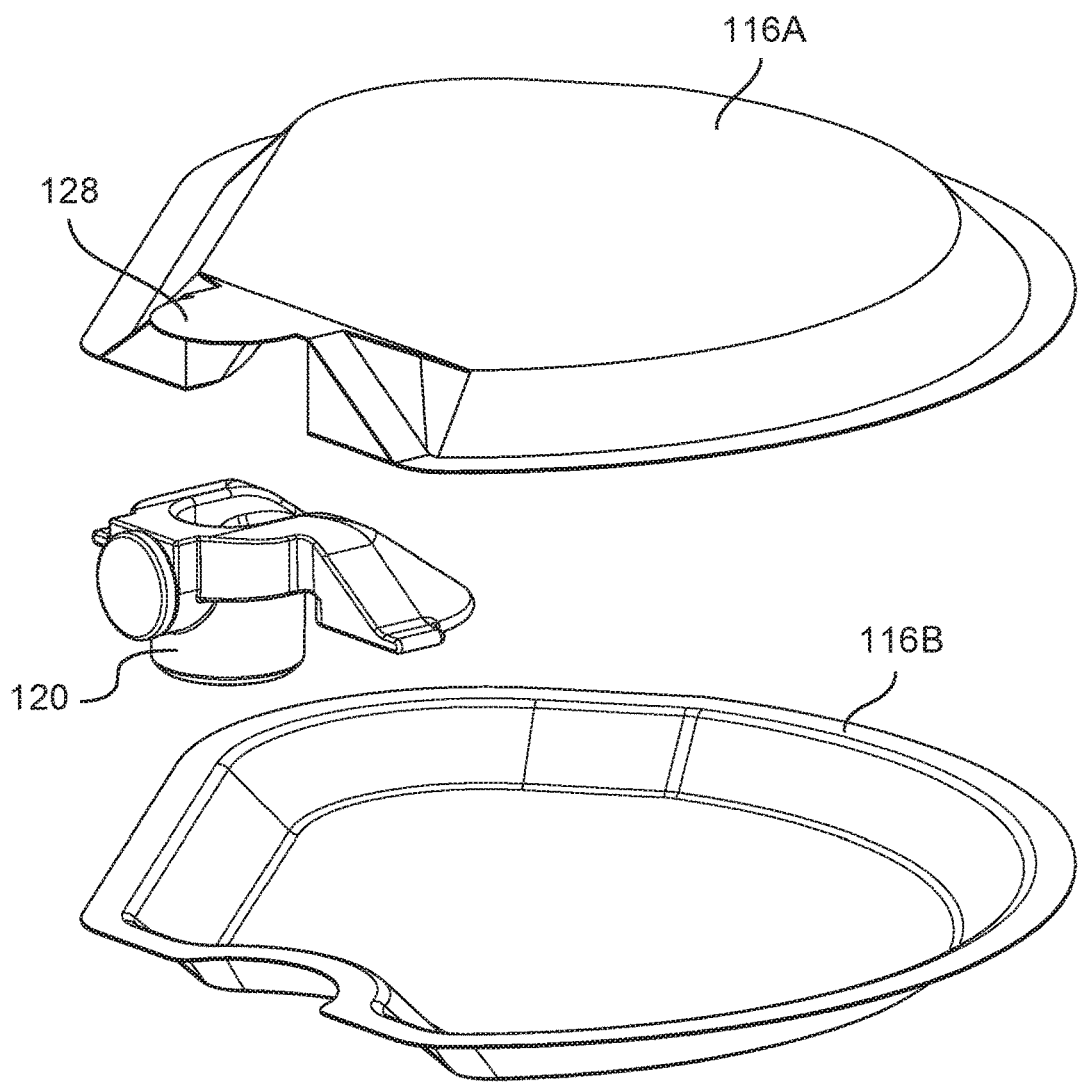
FIG. 5 is an exploded view of the embodiment of the reservoir assembly of FIG. 2.

Referring now also to FIGS. 2-4, an example reservoir assembly 100 is shown. An exploded view of the reservoir 100 is depicted in FIG. 5. Referring primarily to FIGS. 2-4, the reservoir assembly 100 includes a reservoir 118 and a port connector 120. A reservoir 118 may be entirely or at least partial constructed of a flexible material. In other embodiments, a reservoir 118 may be rigid or include one or more rigid portions. Any of the materials described in any of the applications or patents incorporated herein by reference, or combinations thereof may be used to construct the reservoir 118 or other reservoirs described herein, however, the reservoirs described herein are not limited to those materials.

As shown, the reservoir assembly 100 includes a number sides. The perimeter edge of the example reservoir assembly 100 includes a number of contoured, round, or arcuate segments 122A, B and a number of substantially flat segments 124A-C. Some the segments may be defined by the reservoir 118. At least a portion of at least one of the segments may be defined by the port connector 120. Though the port connector 120 is shown forming a flat segment 124C (the portion of the port connector extending away from a reservoir is not considered part of the perimeter edge) of the reservoir assembly 100 perimeter, the port connector 120 (and other port connectors described herein) may also be shaped so as to form at least a portion of a rounded segment of the reservoir assembly 100 perimeter. The port connector 120 may define a portion of the perimeter of the reservoir assembly 100 that is less than 25% of the perimeter. In certain embodiments, less than 20% or 15% (e.g. between 15-10% or about 13% in this example embodiment) of the reservoir assembly 100 perimeter may be defined by the port connector 120. The portion of the port connector 120 external to the reservoir 118 extends away from the reservoir 118 in a manner substantially perpendicular to the segment in which it is located. In other embodiments, the port connector 120 (and other port connectors described herein) may extend away from the segment in which it is located at an acute angle. The shape of the reservoir assembly 100 and/or number, length, and arrangement of flat or round segments 124A-C, 122A, B, may be chosen to allow the reservoir assembly 100 to fit into a reservoir cavity or bay 126 included in a housing assembly 102 (see, e.g. FIGS. 6-7).

As best shown in FIG. 5, a reservoir 118 may be made from a plurality of pieces of material depending on the embodiment. Alternatively, a reservoir 118 may be made from a single piece of material which may, for example, be folded over upon itself. The example reservoir 118 includes two portions 116A, B which are joined around the port connector 120 during manufacture of the reservoir assembly 100. The portions 116A, B may be joined to one another and around the port connector 120 via any suitable type of bonding process. In certain embodiments, the reservoir assembly 100 may be heat bonded or ultrasonically welded together. As shown, at least one of the portions 116A, B of the reservoir 118 may include a tab, flange, or other protuberance 128. When the reservoir assembly 100 is assembled, the protuberance 128 may extend over and be sealed against a portion of the port connector 120. For example, the protuberance 128 may seal over an opening of the port connector 120 which allows for introduction of components into the port connector 120 during assembly. When assembly is complete the port connector 120 may include a portion which is disposed within the interior volume of the reservoir 118 and a portion exterior to the reservoir 118 extending away from the reservoir 118. Other reservoir assemblies described herein may be of similar construction.

Referring now also to FIGS. 2-4, when the reservoir assembly 100 has been assembled, the reservoir 118 may form a first side and an opposing second side of the reservoir assembly 100. Another side of the reservoir assembly 100 may be formed by the port connector 120 along a portion of the periphery of the reservoir assembly 100. The side or face formed by the port connector 120 may be rigid and may be at a non-parallel angle (e.g. substantially perpendicular) to the top and bottom sides formed by the reservoir 118. Other reservoir assemblies described herein may be similarly shaped.

Figure 6:
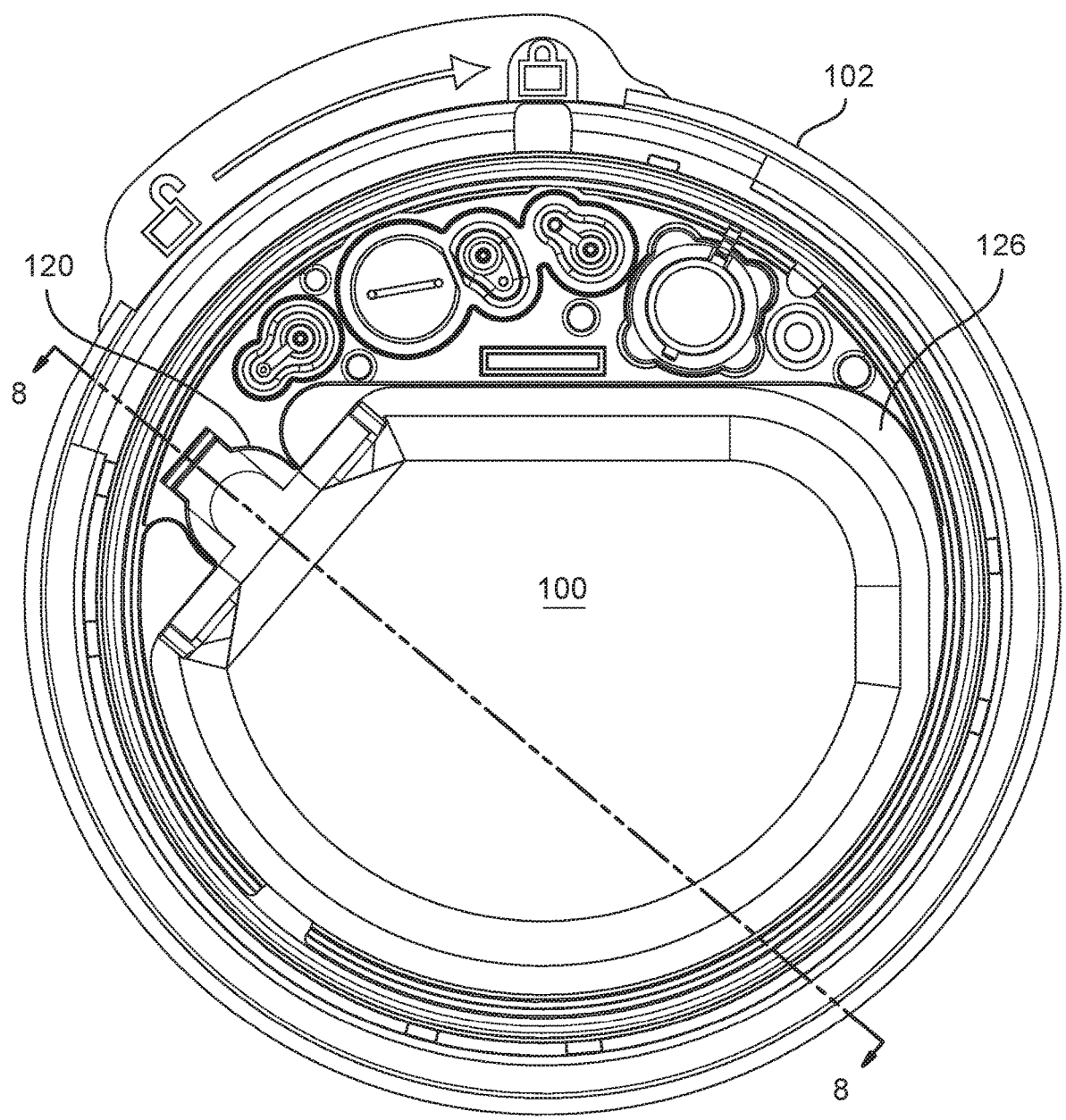
FIG. 6 is a top down view of the embodiment of the reservoir assembly of FIG. 2 installed in an embodiment of a disposable housing assembly.
Figure 7:
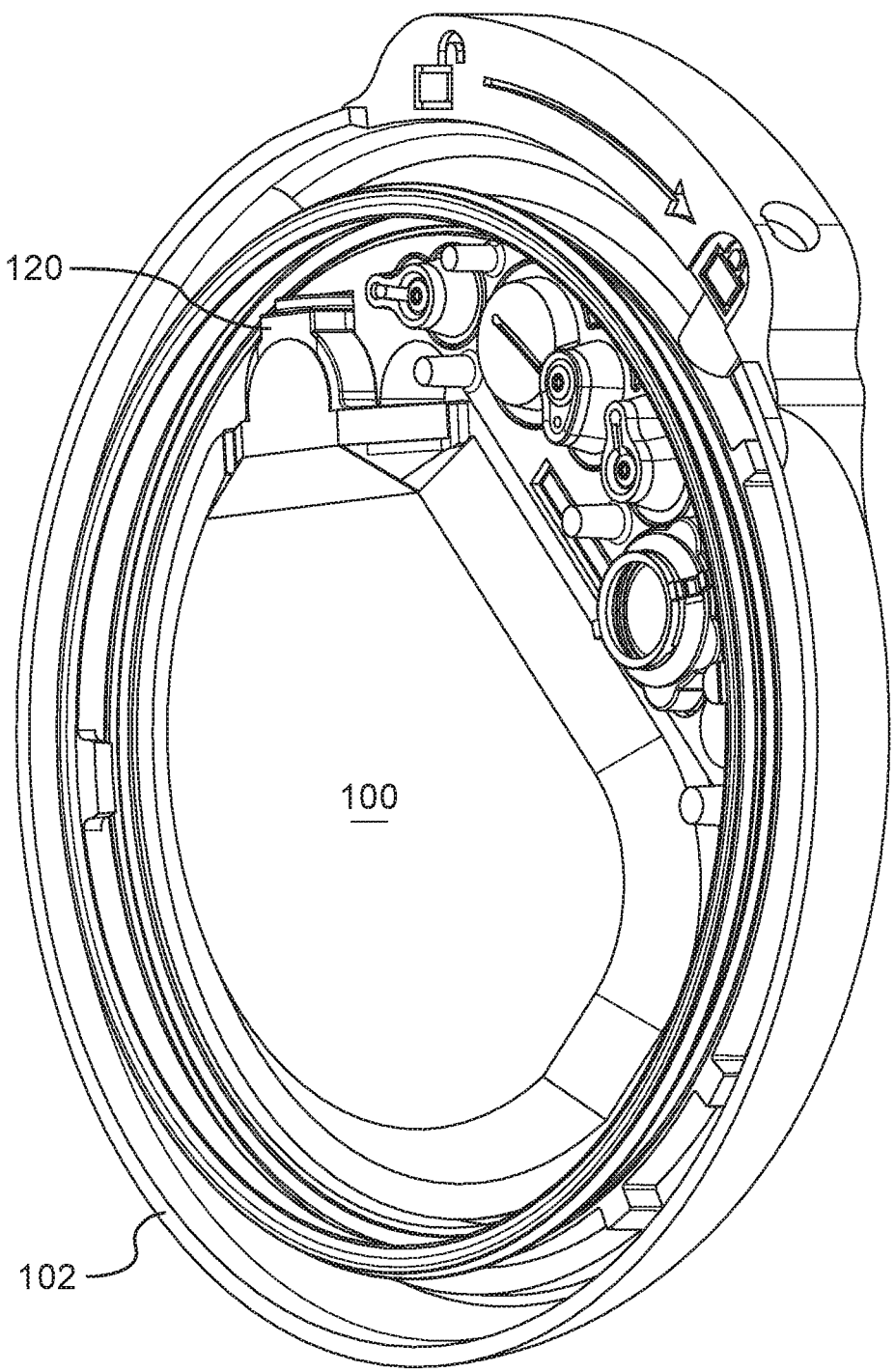
FIG. 7 is a perspective view of the embodiment of the reservoir assembly of FIG. 2 installed in one embodiment of a disposable housing assembly.
Figure 8:
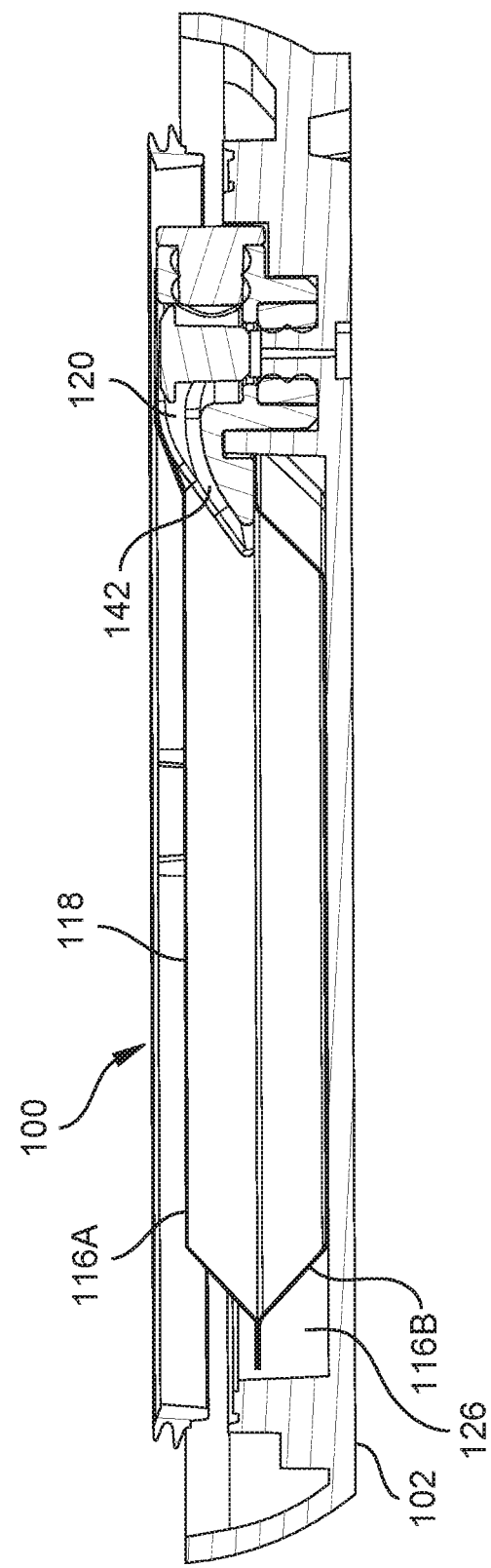
FIG. 8 is a cross sectional view taken at line 8-8 of FIG. 6.
Figure 15:
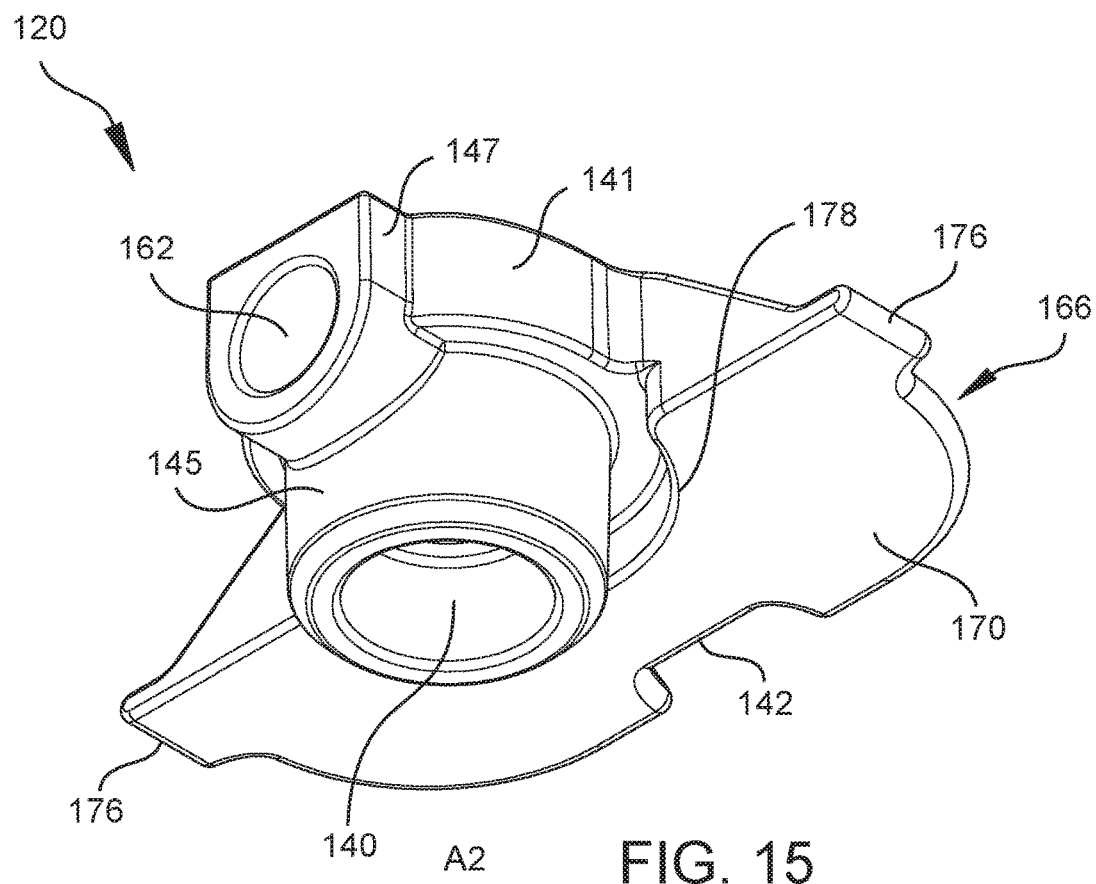
FIG. 15 is a perspective view of the port connector of FIG. 9.
Figure 16:
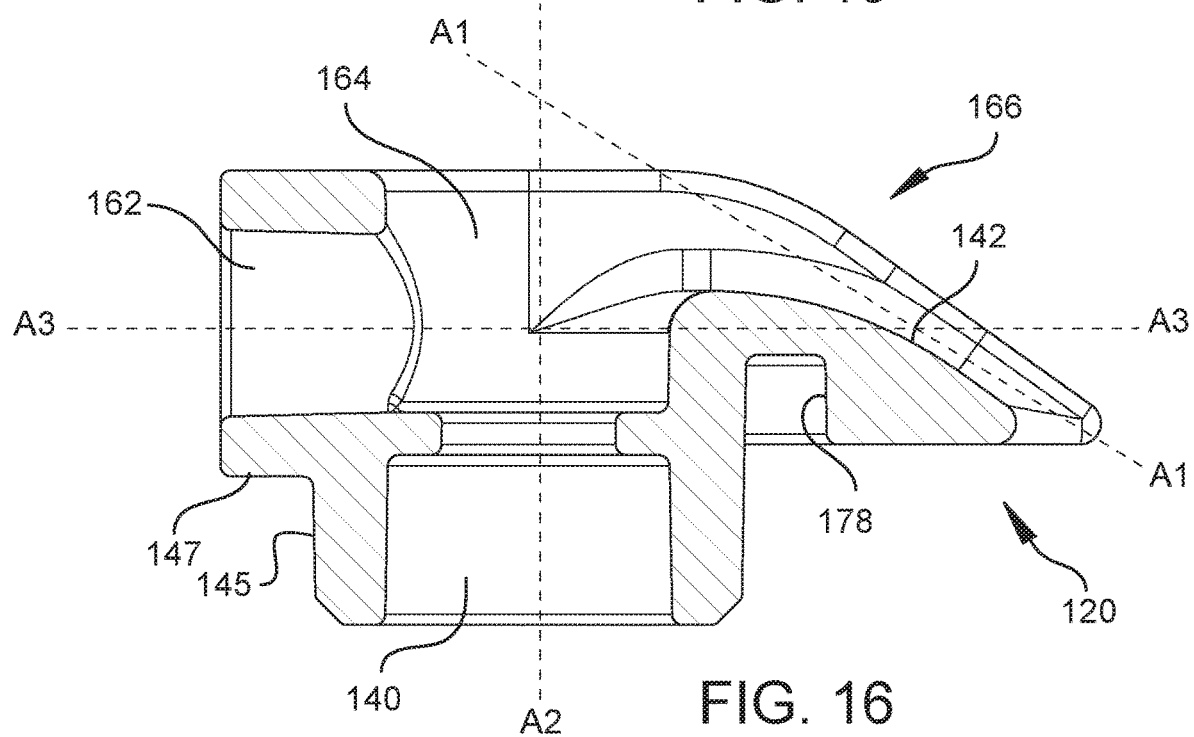
FIG. 16 is a cross sectional view taken at line 16-16 of FIG. 9.
Figure 17A:
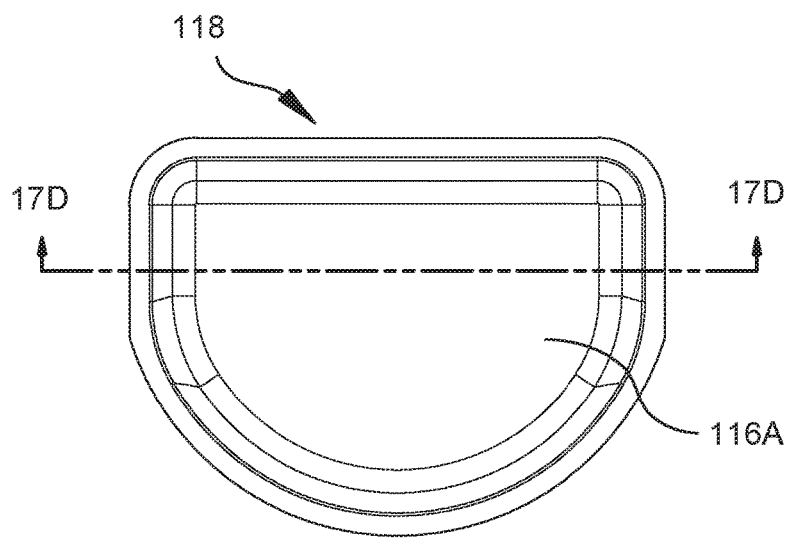
FIGS. 17A-E are various views of one embodiment of a reservoir which has been preformed into a nested configuration.
Figure 17B:
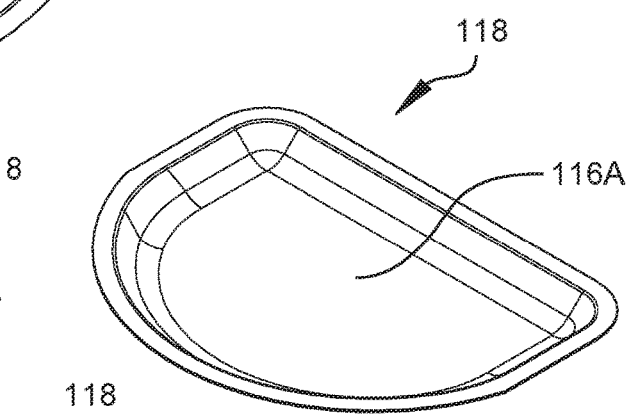
Figure 17C:
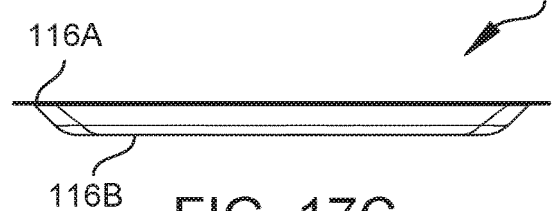
Figure 17D:
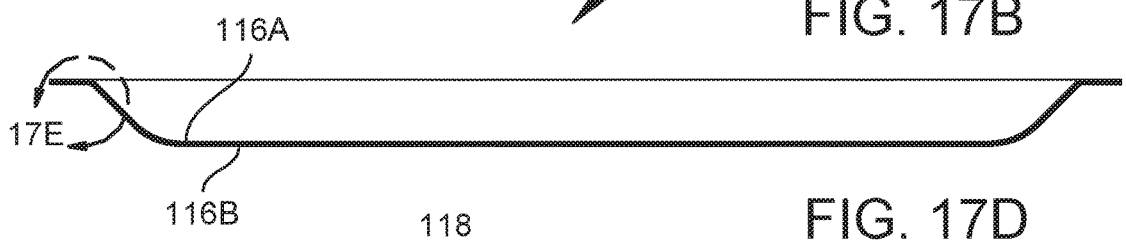
Figure 17E:
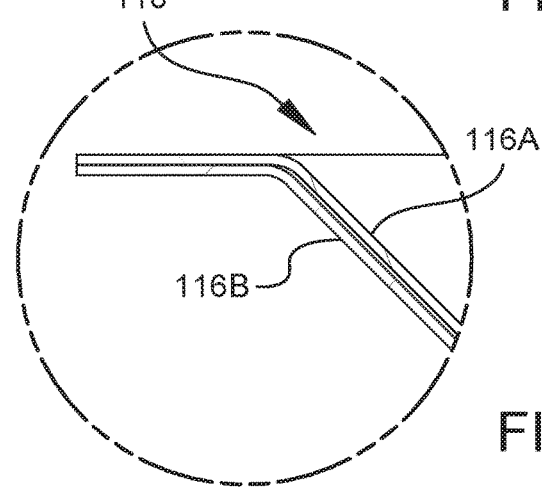

The example reservoir assembly 100 is shown installed within an exemplary disposable housing assembly 102 in FIGS. 6-7. When installed in the disposable housing assembly 102, the port connector 120 may cooperate with a port interface structure to establish a sealed fluid communication channel between the reservoir assembly 100 and various fluid pathways within the disposable housing assembly 102. In some embodiments, a port interface may interact with the port connector 120 as described in any one or more of the application and patents incorporated herein by reference. Such an embodiment is depicted in FIG. 8, a cross-sectional view taken at line 8-8 of FIG. 6. In various embodiments, the port connector 120 may cooperate with a needle instead of a port interface structure as described in any of the applications and/or patents incorporated herein by reference.

Referring now also to FIGS. 9-16, a number of views illustrating the example port connector 120 of FIGS. 2-8 are depicted. As shown, the example port connector 120 includes an inlet 142 which extends from the interior volume of the reservoir assembly 118 (see, e.g. FIG. 8). The port connector 120 also includes a delivery port or outlet 140 through which fluid contained in interior volume of the reservoir assembly 100 may exit the reservoir assembly 100. A filling port 162 may also be included in the port connector 120. The filling port 162 may allow for the reservoir assembly 100 to be filled with a fluid such as insulin or another medicament.

In the example embodiment, the inlet 142, outlet 140, and filling port 162 are all in communication with a common fluid channel or chamber 164 (best shown in FIG. 16) included in the port connector 120. The common fluid channel 164 may serve as an intermediary conduit between at least two or potentially all three of the inlet 142, outlet 140, and filling port 162. In the example embodiment, fluid entering the filling port 162 may pass from the filling port 162 to the common fluid channel 164 and then onto the inlet 142 before reaching the interior volume of the reservoir assembly 100. Fluid exiting the reservoir assembly 100 may pass from the inlet 142, through the common fluid channel 164, and then to the outlet 140.

In the example embodiment, the inlet 142 extends substantially along an axial direction defined by axis A1. The outlet extends substantially along an axial direction defined by axis A2. The filling port 162 extends substantially along an axial direction defined by axis A3. The port connector 120 is substantially symmetric about its vertical medial plane (a plane parallel to, or depending on the embodiment containing, axis A2).

In various embodiments, axis A2 may be substantially perpendicular to axis A3. Axis A1 may be at an acute angle with respect to both axes A2 and A3. These axes A1-A3 may be oriented within the same plane. A portion of the common fluid channel 164 may also be disposed within the plane of axes A1-A3. In some embodiments, all of the axes A1-A3 may intersect at or near a single point. In other embodiments, two of the axes A1-A3 may intersect the other of the axes at separate points. Such an arrangement allows the port connector 120 to be made in a small form factor with fluid pathways of the inlet 142, outlet 140, and filling port 162 still being relatively large in cross-sectional area. In the example embodiment, the width (between projections 176) of the port connector 120 is about five times the diameter of the outlet 140.

In other embodiments, not all of the axes A1-A3 may be oriented along the same plane. In certain embodiments, only two of the axes A1-A3 may intersect. The other axis A1-A3 may be in a skew orientation. In still other embodiments, none of the axes A1-A3 may intersect. In such embodiments, each of the axes A1-A3 may pass through the interior volume of the common fluid channel 164 or extend tangential to a wall defining the common fluid channel 164. One or more of the axes A1-A3 may also be oriented to pass external to the interior volume of the common fluid channel 164, but close enough that the fluid pathway formed by that axis' respective inlet 142, outlet 140, or filling port 162 communicates with the common fluid channel 164. The arrangements of axes described above may also be used in any of the other embodiments of port connectors described herein.

Still referring also to FIGS. 9-16, in some embodiments, a wall 145 surrounding axis A2 may be included and may extend substantially parallel to the direction of axis A2. The wall 145 may serve to define the outlet 140 as well as at least a portion of the common fluid channel 164. The wall 145 may be annular and may include a thicker head portion 141 on the end of the wall 145 opposite the outlet 140. The head portion 141 may provide a larger surface on which to couple or bond protuberance 128 (see, e.g. FIG. 5) of the reservoir 118. The filling port 162 may extend through the wall 145 and to the common fluid channel 164. In some embodiments, a second wall 147 surrounding axis A3 may project from the wall 145 and may extend along the direction of axis A3. The second wall 147 may define a portion of the filling port 162.

As shown, the example port connector 120 also includes a flange member 166. The flange member 166 may extend in a direction outward from or lateral to axis A2 and may extend from or near the top end (the end opposing outlet 140) of the port connector 120. The flange member 166 may serve as a coupling structure which provides surfaces onto which the reservoir 118 may be bonded or welded during assembly of a reservoir assembly 100. The inlet 142 may be defined in a portion of the flange member 166 as well. In the example embodiment, the inlet 142 is open on one side and may be defined as a trough which is recessed into a top face 168 of the flange member 166. In alternative embodiments, the inlet 142 may be a completely enclosed flow conduit which is located entirely within the flange member 166. Other inlets described herein may be similarly formed.

Portions of a flange member 166 may be angled or contoured. In the example embodiment, the top face 168 of the flange member 166 includes a number of contours. At a first portion 172 of the flange member 166 which extends in a direction substantially perpendicular to axis A2, the top face 168 of the flange member 166 is contoured or angled toward the bottom face 170 of the flange member 166. The first portion 172 becomes thinner as distance from the axis A2 increases. A second portion 174 of the example flange member 166 which extends from the first portion 172 in a direction substantially parallel to axis A3 may also be contoured or angled toward the bottom face 170. The second portion 174 also generally becomes thinner as distance from axis A2 increases. Two projections 176 are also included at the ends of the first portion 172 located most distal to axis A2. The projections 176 may serve to provide excess material which may melt and help to form a heat seal as a reservoir is bonded to the port connector 120.

A flange member 166 may also include a portion having a stepped feature 178. In the example embodiment, a stepped feature 178 (best shown in FIGS. 11, 13, 14, 16) is included in the bottom face 170 of the flange member 166. This stepped feature 178 may serve to accept a projecting feature of a disposable housing assembly 102 and aid in placement of reservoir assembly 100 into the disposable housing assembly 102. In the example embodiment, the bottom face 170 of the flange member 166 is otherwise substantially flat or planar.

Still referring also to FIGS. 9-16, the angle of the top face 168 of the first portion 172 of the flange member 166 relative to the bottom face 170 may be chosen to be relatively gentle. The angle may, for example, be less than or equal to 45°, 40°, 35°, or 30° depending on the embodiment. In the example embodiment, the angle is about 35°. Having a gentler angle may facilitate joining of the reservoir 118 material(s) to the port connector 120 during assembly. Once the reservoir 118 material is joined to the port connector 120, a front face 177 of the flange member 166 may form one of the exterior walls defining the interior volume of the reservoir assembly 100 (see, e.g. FIG. 3).

The angle of the top face 170 of the second portion 174 of the flange member 166 with respect to the bottom face may also be relatively gentle. The angle may be similar to those described in the preceding paragraph. In some embodiments, the angle of the top face 170 of first and second portion 172, 174 with respect to the bottom face 170 may be the same or substantially the same. As fluid contained in the reservoir assembly 100 is depleted during use, the reservoir 118 material may collapse. The angle of top face 170 of the second portion 174 with respect to the bottom face 170 may aid in directing the collapse of the reservoir material 118. Specifically, the angle may help to direct collapse such that any bunching, folding, crinkling, etc. of the reservoir 118 material is avoided. In return, this may help to prevent trapping of valuable fluid within pockets in the reservoir assembly 100 when the reservoir assembly 100 is in a collapsed state.

Referring now also to FIGS. 17A-E, the portions 116A, B of the reservoir 118 may be made in a preformed shape which aids in preventing bunching and trapping of fluid in the reservoir assembly 100 as it is depleted. Other reservoirs described herein may be similarly preformed. As shown, the portions 116A, B may be performed so as to closely nest together when the reservoir assembly 100 is in an empty state. In specific embodiments, an inside portion 116A of the reservoir 118 may be preformed to nest inside an outside portion 116B of the reservoir 118. These portions 116A, B may then be bonded together and attached to a port connector 120 as described elsewhere herein. Such a nested configuration may allow the portions 116A, B to more naturally collapse into an empty state with minimal bunching and pocketing of fluid.

Though the preformed shape of portion 116A in the example embodiment mimics the shape of portion 116B, other embodiments may include portions 116A, B including additional preformed features. In some embodiments, one or both of the portions 116A, B may be preformed to have a section which mimics the shape of a part of the port connector 120 to which the portions 116A, B are to be attached. In such embodiments, the rest of the portions 116A, B may be preformed to closely nest together as shown in FIGS. 17A-E.

Referring now primarily to FIGS. 18-22, once the reservoir 118 material is attached to the port connector 120, the reservoir assembly 100 may be filled with fluid and sealed for storage. As shown in FIG. 18, a sectional view of the example reservoir assembly 100 taken through the medial plane of the port connector 120, the reservoir assembly 100 may begin with the reservoir 118 in a collapsed state. The filling port 162 may be open such that a fluid pathway exists between the filling port 162 and the inlet 142.

A pin 150 (best shown in FIGS. 20 and 21A) may be included in port connector 120 and may block the outlet 140 and extend at least partially into the common fluid channel 146. The pin 150 may include a head 151. The pin 150 may be displaceable within the port connector 120 and may cooperate with a shoulder 152 and various seals 154, 156 included in the port connector 120 to selectively seal off fluid communication between the inlet 142 and outlet 140. The pin 150 is depicted in a sealing position in FIG. 18. As shown, the pin 150 is blocking the fluid pathway between the inlet 142 and outlet 140. A number of pin 150, shoulder 152, and seal 154, 156 variations which may be used in any combination with the embodiments of port connectors 120 described herein are disclosed in any one or more of the applications and/or patents incorporated herein by reference. Actuation of a pin is also described in any one or more of the applications and/or patents incorporated herein by reference, and pins described in the present disclosure may be actuated in the same or similar fashion.

As shown in FIGS. 19 and 20, a dispenser 190 may be introduced to filling port 162. In the example embodiment, the dispenser 190 includes a nozzle at its outlet. The filling port 162 may include one or more sealing member (e.g. o-rings) to form a seal around the dispenser 190 when the dispenser 190. The filling port 162 may also include a stop surface which may limit the depth to which the dispenser 190 projects into the port connector 120. Once the dispenser 190 is in place in the port connector 120, fluid may be dispensed into the reservoir assembly 100 until the reservoir assembly has been filled to a predetermined amount (e.g. to capacity). In some embodiments, during a filling operation, the dispenser 190 may also be arranged to apply a vacuum to the reservoir assembly 100 through the fill port 162 and the fill port 162 may double as a vacuum port. This may help to limit the amount of air present in the reservoir assembly 100 after filling.

It is preferred that the pin 150 (shown in isolation in FIG. 21A) is held in a substantially static position while a filling operation is occurring. This may help to ensure that leaking of fluid does not occur as the reservoir assembly 100 is filled from the dispenser 100. If vacuum is applied to the reservoir assembly 100 before filling, this may also help to prevent the pin 150 from displacing under vacuum. In certain embodiments, the act of introducing the dispenser 190 into the connector assembly 120 may serve to immobilize the pin 150. The act of withdrawing the dispenser 190 may automatically cause the pin 150 to regain its ability to displace within the port connector 120.

As shown in the example embodiment, to ensure that the pin 150 is immobile during a filling operation, cooperating features on the dispenser 190 and pin 150 may enter an engaged state. In the engaged state, the pin 150 may be fixed relative to the dispenser 190. Any variety of cooperating features may be used. In the example embodiment, and as best shown in FIGS. 20 and 21A, the pin 150 may include a head 151 of slightly larger diameter than the body 153 of the pin 150. The head 151 may include an interference feature 155 along its edge. In the example embodiment, the head 151 has a chamfered edge. Alternatively, the edge could include a step, fillet, slot, projection, orifice, etc. The interference feature 155 may engage with a second complimentary interference feature 195 located on the dispenser 190. When engaged, a mechanical interference may be established which inhibits displacement of the pin 150. This allows for the pin 150 to be held statically in the port connector 120 with requiring any additional fixturing.

Though the dispenser 190 in the example embodiment engages with a feature included in the edge of the pin 150 head 151, the dispenser 190 may form a mechanical interference that prevents pin 150 displacement in other manners. For example, a portion of the dispenser 190 may extend over at least a portion of a top face 157 of the head 151.

Referring now also to FIG. 21B, in other embodiments, the pin 150 may be held into position in other manners as well. For example, the pin 150 may be connected to a frangible 181. The frangible 181 may extend outside of the port connector 120 such that the frangible may be held or otherwise captured while the filling process occurs. This may keep the pin 150 from displacing within the port connector 120. Once the frangible 181 is no longer needed it may be broken off of the pin 150 leaving substantially only the pin 150 behind in the port connector 120. Any suitable frangible may be used 181. As shown, the frangible is connected to the pin 150 via a frangible bridge 183. This frangible bridge 183 may be readily breakable with little force to remove the frangible 181 from the pin 150.

As fluid is expelled from the dispenser 190 into the reservoir assembly 100, it may pass through the common fluid channel 164 and inlet 142 before reaching the interior volume of reservoir 118. The inlet 142 of the port connector 120 may be formed such that the reservoir assembly 100 may be rapidly filled. In certain examples, the inlet 142 may facilitate filling of the reservoir assembly 100 in 1-2 seconds (e.g. 1.5 seconds) or less. The cross-sectional area of the flow path formed by the inlet may be chosen to accommodate a predetermined flow rate of fluid into the reservoir 118. The cross-sectional area of the inlet 142 may be greater than or equal to a cross-sectional area of the dispenser 190 outlet. In certain embodiments, the cross-sectional area of the inlet 142 may be about 1-4 times that of the dispenser 190 outlet.

Referring now also to FIG. 22, once the reservoir assembly 100 has been filled the filling port 162 may be blocked off. In the example embodiment, a plug member or stopper 200 may be placed into the filling port 162. The filling port 162 may include one or more sealing member(s) 202A, 202B which help to establish a seal around the stopper 200. The sealing members 202A, B may be constructed of a compliant material such as an elastomer and may be provided in the form of o-rings in some embodiments. In alternative embodiments, the stopper or plug member 200 may include the at least one sealing member 202A, B. In such embodiments, the sealing members 202A, B may be formed as bumps, ribs, or ridges along the exterior face of the stopper 200. In some embodiments, the stopper 200 itself may be constructed of a compliant elastomer or other suitable gasketing material. In such embodiments, a robust seal may be formed by compression of the stopper 200 material against the walls of the filling port 162 and sealing members 202A, B may be optional.

In some embodiments, an end 204 of the stopper 200 disposed in the port connector 120 may include a barb, latch, or other catch feature (not shown) which aids in retaining the stopper 200 within the filling port 162. This feature may be bent, deflected, or compressed inward toward the axis A3 of the filling port 162 during insertion of the stopper 200. Once fully installed, the feature may restore outward such that it overhangs the interior surface 206 of wall 145 helping to prevent removal of the stopper 200.

Figure 23:
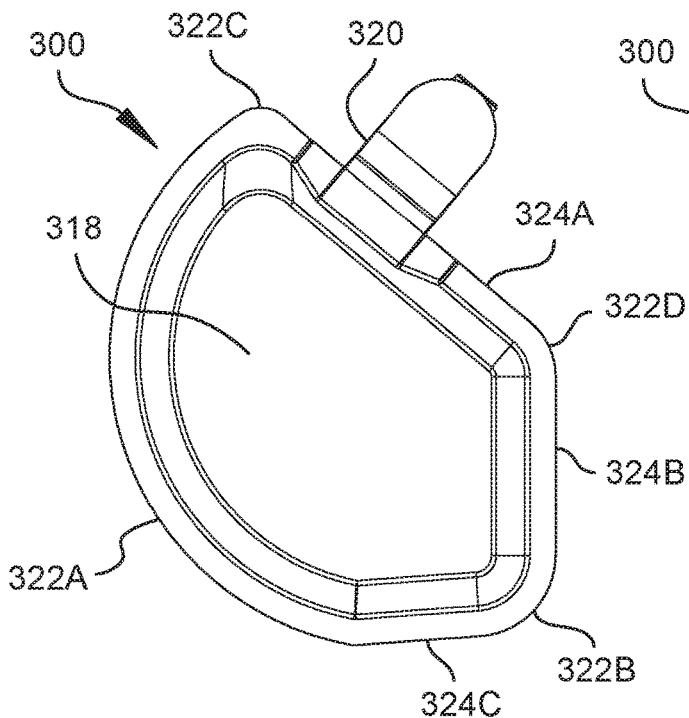
FIG. 23 is a top down view of one embodiment of a reservoir assembly.
Figure 24:
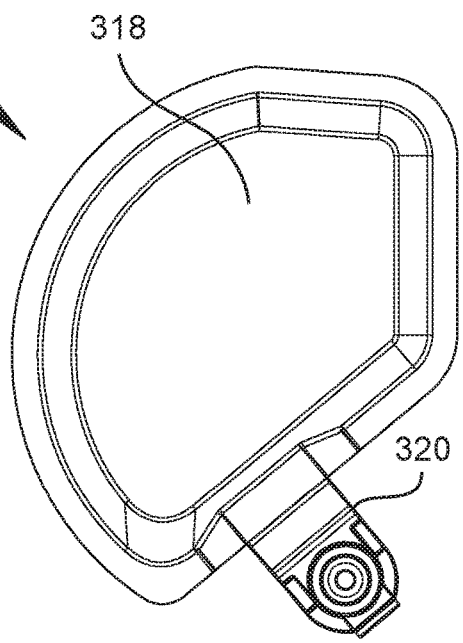
FIG. 24 is a bottom up view of one embodiment of a reservoir assembly of FIG. 23.
Figure 25:
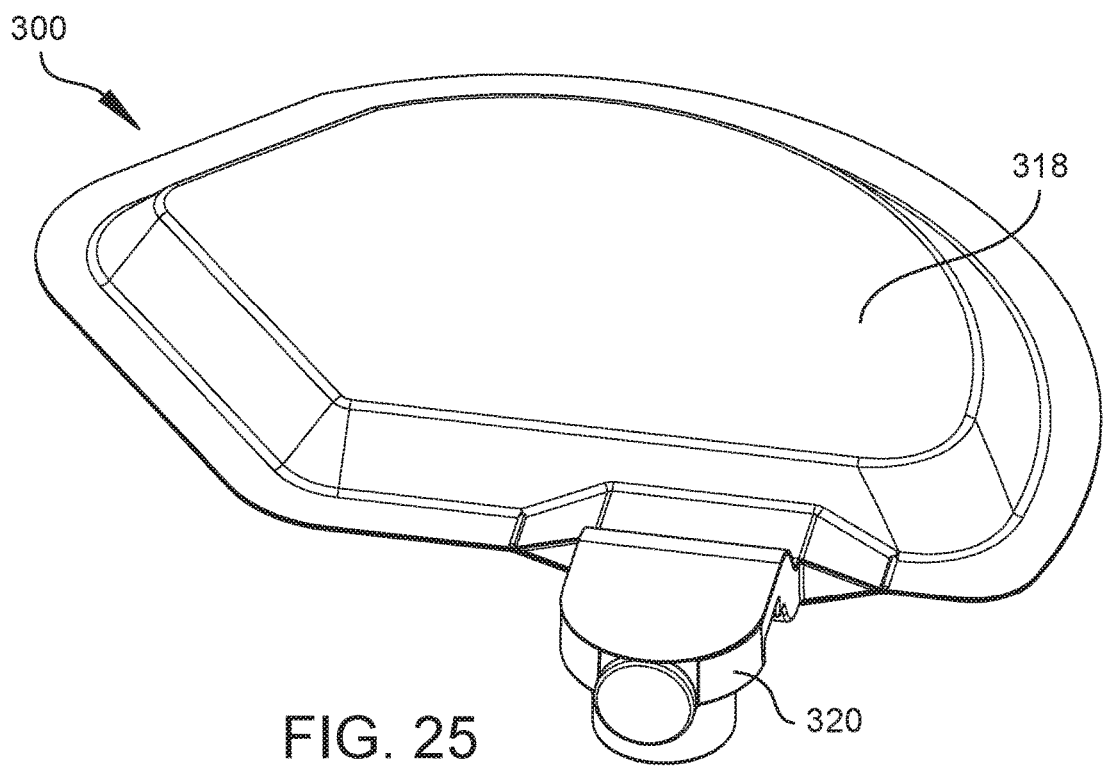
FIG. 25 is a perspective view of the reservoir assembly of FIG. 23.

Referring now also to FIGS. 23-25 another example reservoir assembly 300 is depicted. The example reservoir assembly 300 includes a reservoir 318 and a port connector 320. The perimeter edge of the example reservoir assembly 300 includes a number of contoured, round, or arcuate segments 322A-D and a number of substantially flat segments 324A-C. Some the segments may be defined by the reservoir 318. At least a portion of at least one of the segments may be defined by the port connector 320. In the example, the port connector 320 is shown forming a portion of flat segment 324A. The port connector 320 may be centered in the segment of which it forms a part. In the example embodiment, the port connector 320 is disposed offset from the center of the segment in which it is included. The portion of the example port connector 320 external to the reservoir 318 extends perpendicular to the segment in which it is located, though other angles are also possible. The port connector 320 may define a portion of the perimeter of the reservoir assembly 300 that is less than 25% of the perimeter. In certain embodiments, less than 20% or 15% of the reservoir assembly 300 perimeter may be defined by the port connector 320.

Figure 26:
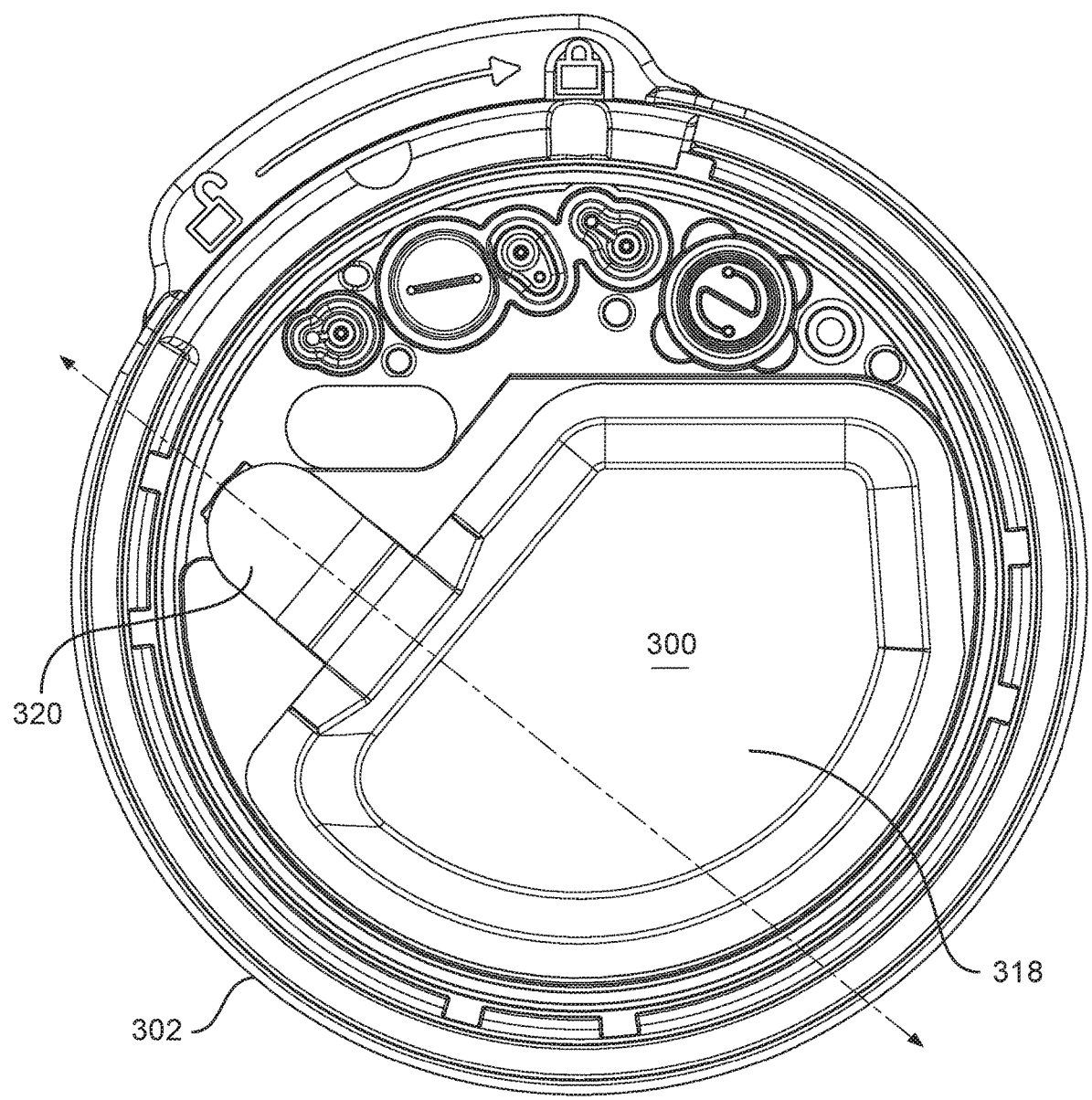
FIG. 26 is a top down view of the reservoir assembly of FIG. 23 installed in one embodiment of a disposable housing assembly.
Figure 27:
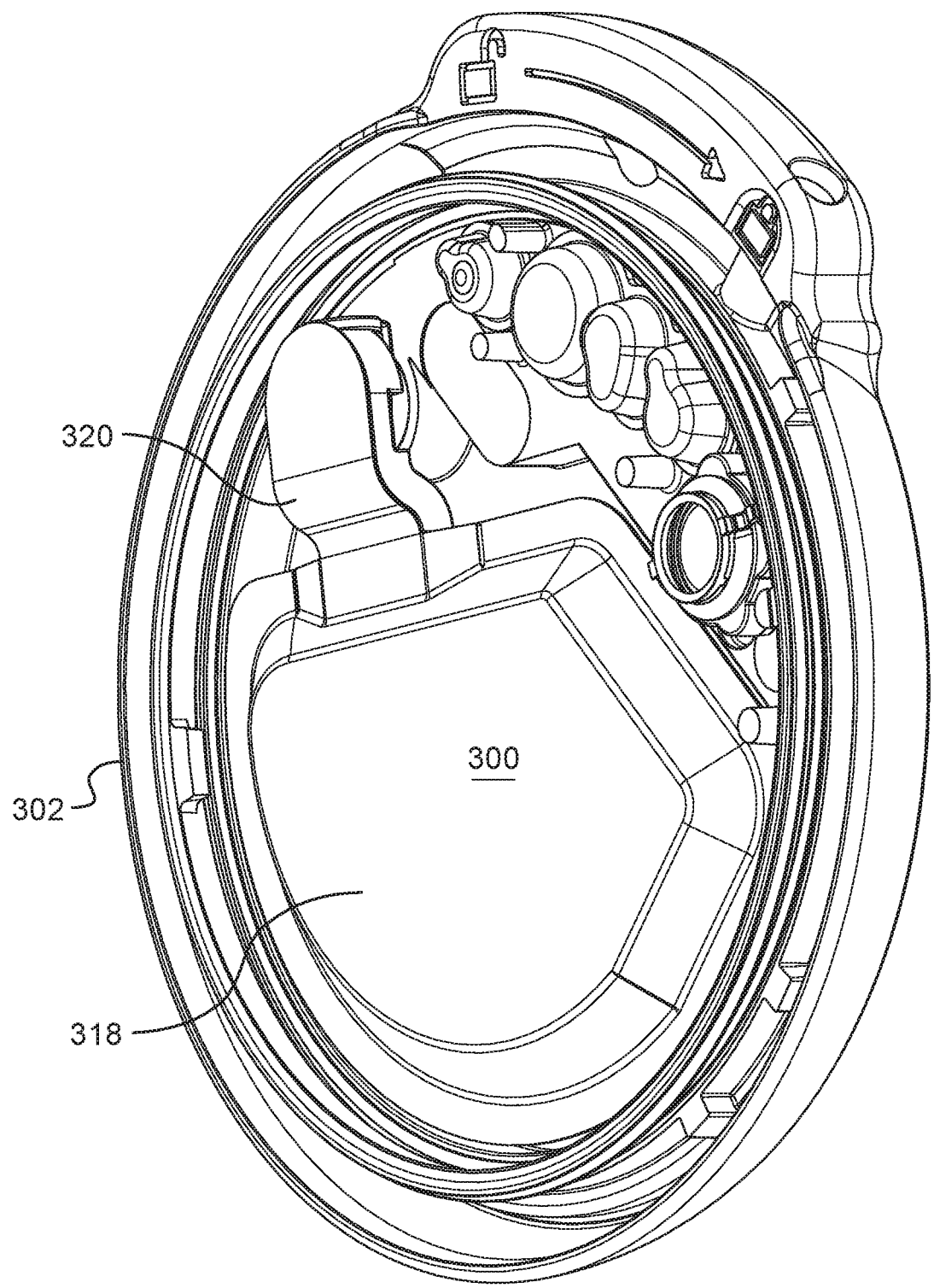
FIG. 27 is a perspective view of the reservoir assembly of FIG. 23 installed in one embodiment of a disposable housing assembly.

The example reservoir assembly 300 is shown installed within an exemplary disposable housing assembly 302 in FIGS. 26-27. When installed in the disposable housing assembly 302, the port connector 320 may cooperate with a port interface structure to establish a sealed fluid communication channel between the reservoir assembly 300 and various fluid pathways within the disposable housing assembly 302. This interaction may be as described elsewhere in the specification although a needle type connection may also be formed in alternative embodiments.

As shown, the port connector 320 extends a greater distance away from the reservoir 318 than the port connector 120 depicted in FIGS. 6-7. To accommodate this, the reservoir 318 may be constructed to have a smaller footprint. The reservoir 318 may be smaller in volume than the reservoir assembly depicted in FIGS. 6-7. Alternatively, a height dimension of the reservoir 318 may be increased to allow for the reservoir assembly 300 to hold a volume comparable to of the reservoir assembly 100 shown in FIGS. 6-7.

Referring now also to FIGS. 28-35, a number of views illustrating the example port connector 320 of FIGS. 23-27 are depicted. As shown, the example port connector 320 includes an inlet 342 which extends from the interior volume of the reservoir assembly 318. The port connector 320 also includes a delivery port or outlet 340 through which fluid contained in interior volume of the reservoir assembly 300 may exit the reservoir assembly 300. A filling port 362 may also be included in the port connector 320. The filling port 362 may allow for the reservoir assembly 300 to be filled with a fluid such as insulin or another medicament.

In the example embodiment, the inlet 342, outlet 340, and filling port 362 are all in communication with a common fluid channel or chamber 364 (best shown in FIG. 35) included in the connection port 320. The common fluid channel 364 may act similarly to as described in relation to FIGS. 9-16.

In the example embodiment, the port connector 320 is substantially symmetric about is medial plane. The outlet 340 extends substantially along an axial direction defined by axis A4. The filling port 362 extends substantially along an axial direction defined by axis A5. The inlet 342 includes a number of segments. A first section 361 of the inlet 342 which directly communicates with the common fluid channel 364 extends substantially straight and in a direction generally parallel to axis A5 of the filling port 362. An intermediate section 363 of the inlet 342 follows a curving path. A third section 365 of the inlet 342 extends substantially straight and along a direction generally parallel to the first section 361. The intermediate section 363 may follow a path that resembles a sigmoidal curve. In other embodiments, the intermediate section may be relatively straight, but oriented at an angle with respect to the first section 361 and second section 365. In certain embodiments the angle may be between 140-90°, 130-100°, or 120-110° (e.g. 120°).

In various embodiments, axis A4 may be substantially perpendicular to axis A5 and the first portion 361 of the inlet 342. The first portion 361 of the inlet 342 and the axes A4-A5 may be oriented within the same plane. A portion of the common fluid channel 164 may also be disposed within this plane. In some embodiments, the direction the first section 361 extends may be coaxial with axis A5. In other embodiments, axis A5 and the direction of extension of the first portion 361 may be parallel but not coaxial. As with port connector 120 described earlier, such an arrangement allows the port connector 320 to be made in a small form factor with fluid pathways of the inlet 342, outlet 340, and filling port 362 still being relatively large in cross-sectional area. In the example embodiment, the width (between projections 376) of the port connector 320 is about six to seven times the diameter of the outlet 140. In alternative embodiments, the first portion 361 of the inlet 342 may extend in a direction similar to those described in relation to axis A1 of FIGS. 9-16.

Still referring also to FIGS. 28-35, in some embodiments, a wall 345 surrounding axis A4 may be included and may extend substantially parallel to the direction of axis A4. The wall 345 may serve to define the outlet 340 as well as at least a portion of the common fluid channel 364. The wall 345 may be annular and may include a thicker head portion 341 on the end of the wall 345 opposite the outlet 340. The head portion 341 may provide a larger surface on which to attach or couple protuberance 328 of the reservoir 318. The filling port 362 may extend through the wall 345 and to the common fluid channel 364. In some embodiments, a second wall 347 surrounding axis A5 may project from the wall 345 and may extend along the direction of axis A4. The second wall 347 may define a portion of the filling port 362.

As shown, the example port connector 320 also includes a flange member 366. The flange member 366 may be coupled to wall 345 via a bridge member 368. The bridge member 368 is coupled to the top end (the end opposing outlet 340) of the port connector 320. The bridge member 368 may extend in a curved or angled path away from the wall 345. This path may mimic the path taken by the intermediate portion 363 of the inlet 342. In the example embodiment, the bridge member 368 follows a curved path of sigmoidal shape. Excluding the recessed region where the intermediate portion 363 of the inlet 342 is formed, the bridge member 368 may be of substantially uniform thickness. In other embodiments, the bridge member 368 may thin or thicken (continuously or in stepwise fashion) as distance from the wall 345 increases.

Figure 34:
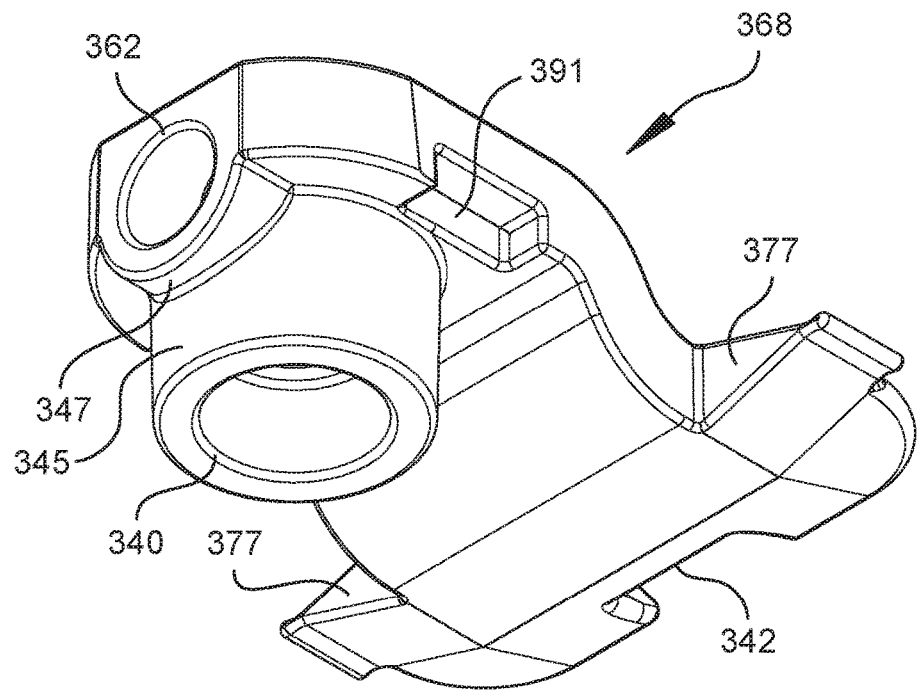
FIG. 34 is a perspective view of the port connector of FIG. 28.
Figure 35:
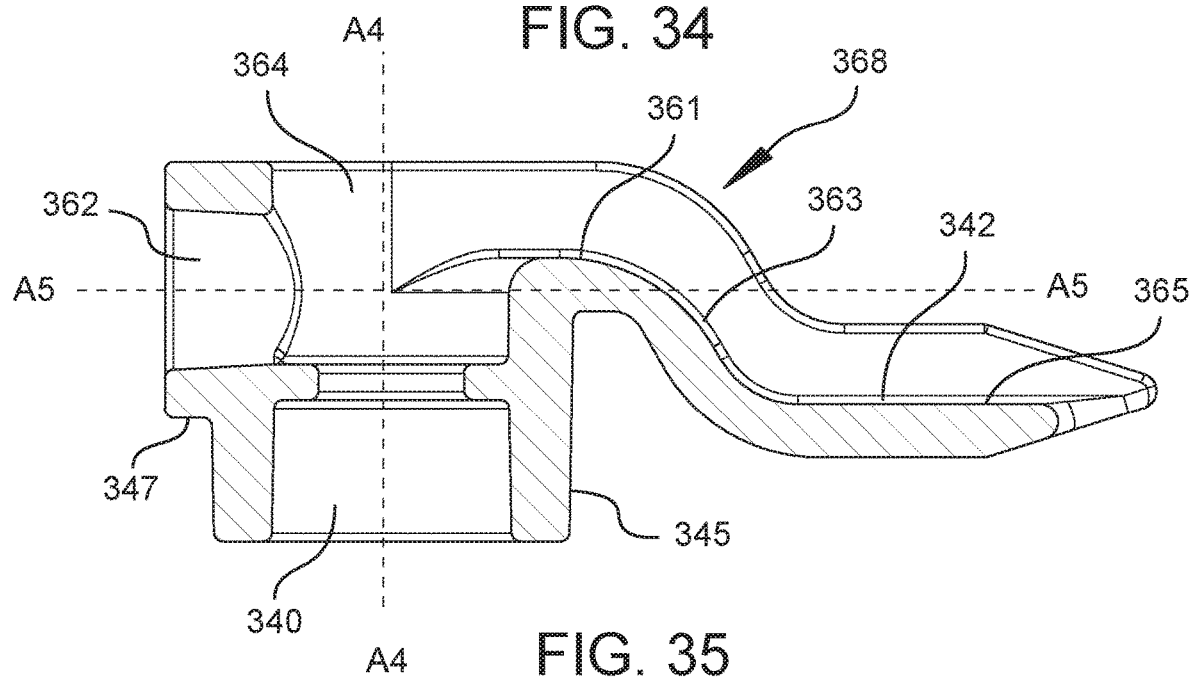
FIG. 35 is a cross sectional view taken at line 35-35 of FIG. 28.
Figures 36, 37:
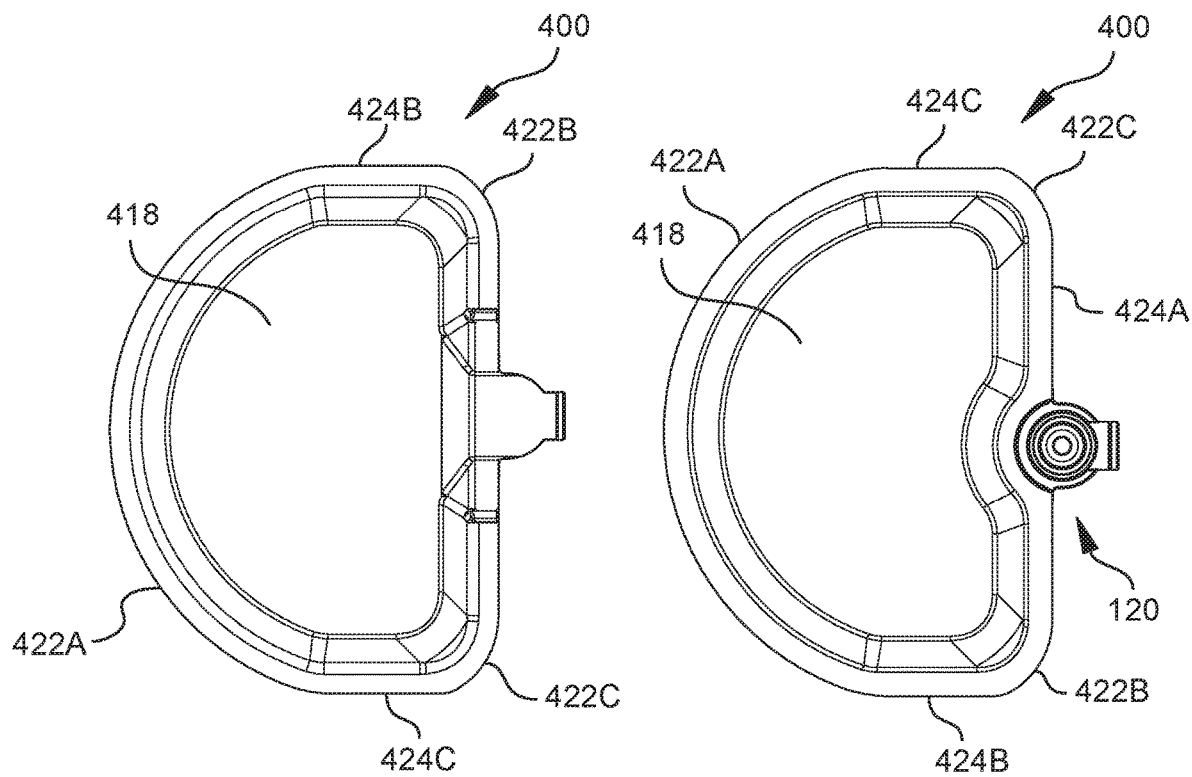
FIG. 36 is a top down view of one embodiment of a reservoir assembly.
FIG. 37 is a bottom up view of the reservoir assembly of FIG. 36.
Figure 38:
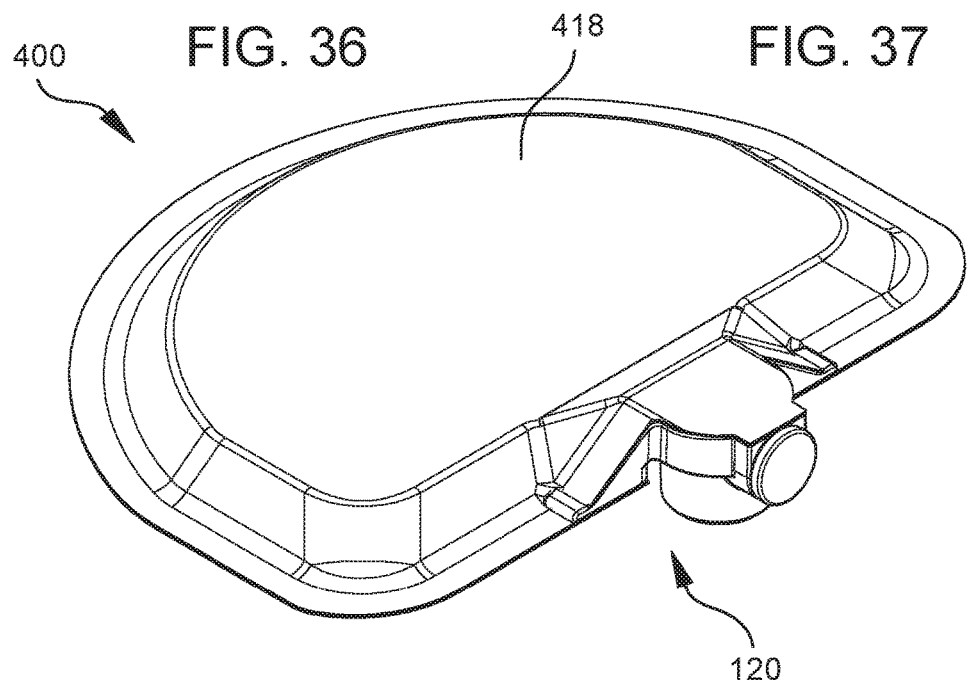
FIG. 38 is a perspective view of the reservoir assembly of FIG. 36.

In certain embodiments, and as best shown in FIG. 34, the head portion 341 may include recessed notches 391. The recessed notches may flank the wall 345 and be recessed into the underside of head portion 341. Each of the notches 391 may receive a snap fit projection of a cover member (see, e.g. 1772 of FIG. 92) for the disposable housing assembly 302 (see, e.g. FIG. 27). This may help to hold the cover member in place on the disposable housing assembly. The stepped feature 178 of the port connector 120 shown in FIGS. 9-16 may be similarly engaged by a snap fit projection of a cover member in certain embodiments.

The flange member 366 may project from the bridge member 368 in a direction leading away from axis A4. In the example embodiment, the flange member 366 projects from the bridge member 368 in a direction substantially perpendicular to axis A4. The flange member 366 may serve as a coupling structure which provides surfaces onto which the reservoir 318 may be bonded or welded during assembly of a reservoir assembly 300. The third section 365 of the inlet 342 may be defined in a portion of the flange member 366 as well.

Portions of a flange member 366 may be angled or contoured. In the example embodiment, the top face 369 and bottom face 370 of the flange member 366 include a number of contours. At a first portion 372 of the flange member 366 which extends in a direction substantially perpendicular to axis A4 and axis A5, the flange member 366 may include top and bottom faces 369, 370 contoured or angled toward the horizontal (parallel to a plane including axis A5) medial plane of the flange member 366 (best shown in FIG. 30). The first portion 372 becomes thinner as distance from the axis A5 increases in the example embodiment. A second portion 374 of the example flange member 366 which extends from the first portion 372 in a direction substantially parallel to axis A4 may also be contoured or angled toward the horizontal medial plane (best shown in FIG. 29) of the flange member 366. The second portion 374 also generally becomes thinner as distance from axis A4 increases. Two projections 376 are also included at the ends of the first portion 372 located most distal to axis A5.

Still referring also to FIGS. 28-35, the angle of the top face 369 and bottom face 370 of first portion 372 of the flange member 366 relative to its horizontal medial plane may be chosen to be relatively gentle. The angle of the top face 369 and bottom face 370 with respect to the horizontal medial plane of the flange member 366 may be equal, though this may differ in other embodiments. The angle may, for example, be less than or equal to 30°, 25°, 20°, or 15° depending on the embodiment. In the example embodiment, the angle is about 18°. Having a gentler angle may facilitate joining of the reservoir 118 material(s) to the port connector 120 during assembly. Angling both the top face 369 and bottom face 370 with respect to the horizontal medial plane allows the sheets 316A, 316B of the reservoir 318 to require smaller individual bend angles when the sheets 316A, B are joined together. This may help to optimize the manufacturability of the reservoir assembly 300. The projections 376 may also provide extra material which may help to facilitate this joining. Once the reservoir 318 material is joined to the port connector 320, a front face 377 of the flange member 366 may form part of one of the exterior walls defining the interior volume of the reservoir assembly 300 (see, e.g. FIG. 25).

The angle of the top face 369 bottom face 370 of the second portion 374 of the flange member 366 with respect horizontal medial plane of the flange member 366 may also be relatively gentle. The angles may be similar to or the same as those described in the preceding paragraph. As fluid contained in the reservoir assembly 300 is depleted during use, the reservoir 318 material may collapse. The angles of the top and bottom faces 369, 370 of the second portion 174 with respect to the horizontal medial plane may aid in directing the collapse of the reservoir material 318. Specifically, the gentle angle may help to direct collapse such that any bunching, folding, crinkling, etc. of the reservoir 318 material is avoided. In return, this may help to prevent trapping of valuable fluid within pockets in the reservoir assembly 300 when the reservoir assembly 300 is in a collapsed state.

Figure 40:
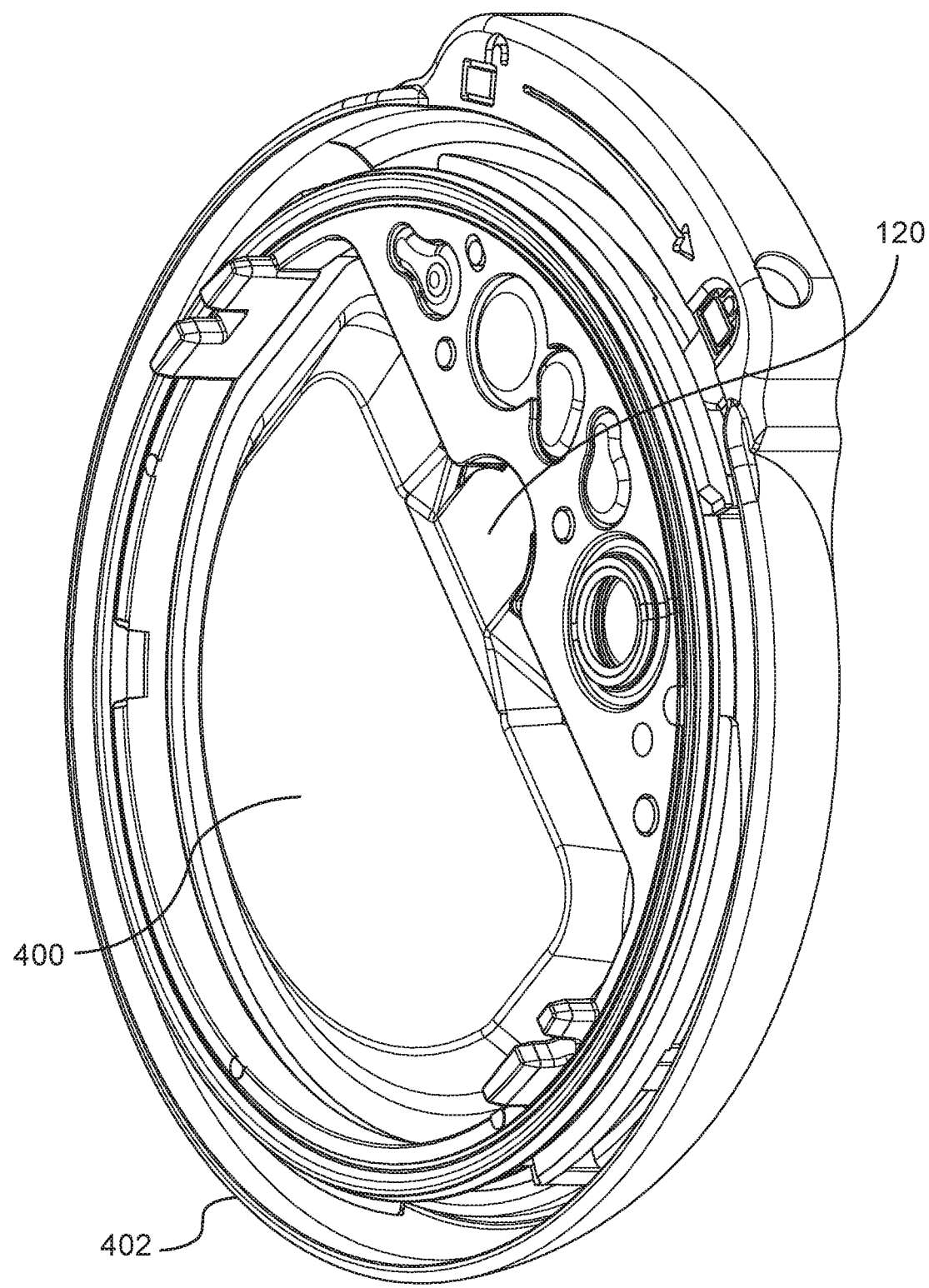
FIG. 40 is a perspective view of the reservoir assembly of FIG. 36 installed in an example disposable housing assembly.
Figure 41:
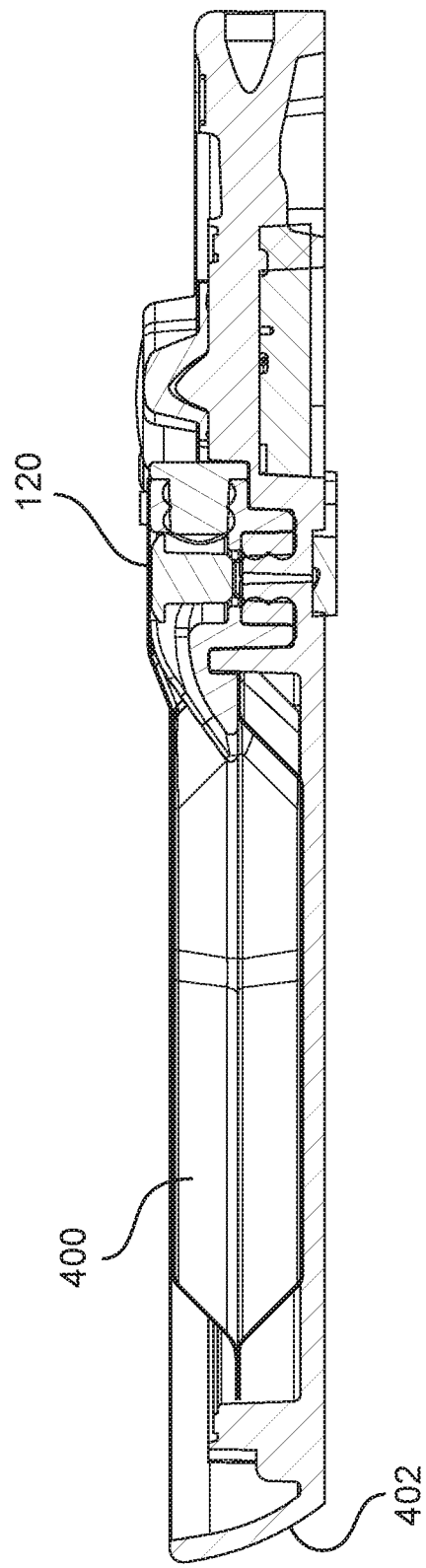
FIG. 41 is a cross section taken at line 41-41 of FIG. 36.
Figures 42, 43:
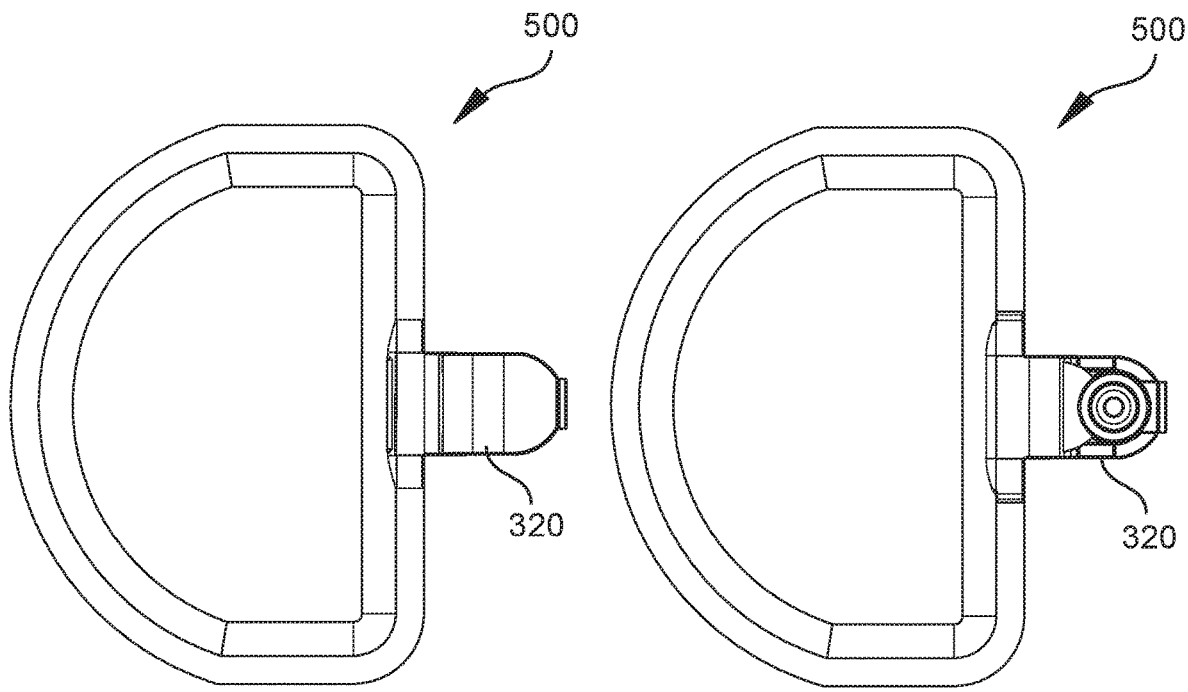
FIG. 42 is a top down view of one embodiment of a reservoir assembly.
FIG. 43 is a bottom up view of the reservoir assembly of FIG. 42.
Figure 44:
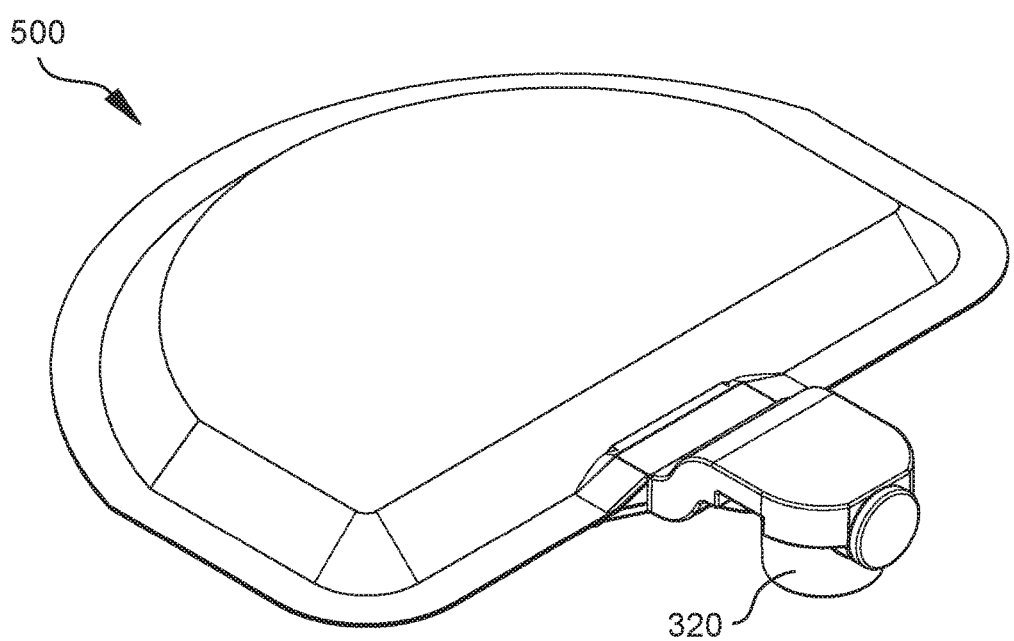
FIG. 44 is a perspective view of the reservoir assembly of FIG. 44.
Figures 45, 46:
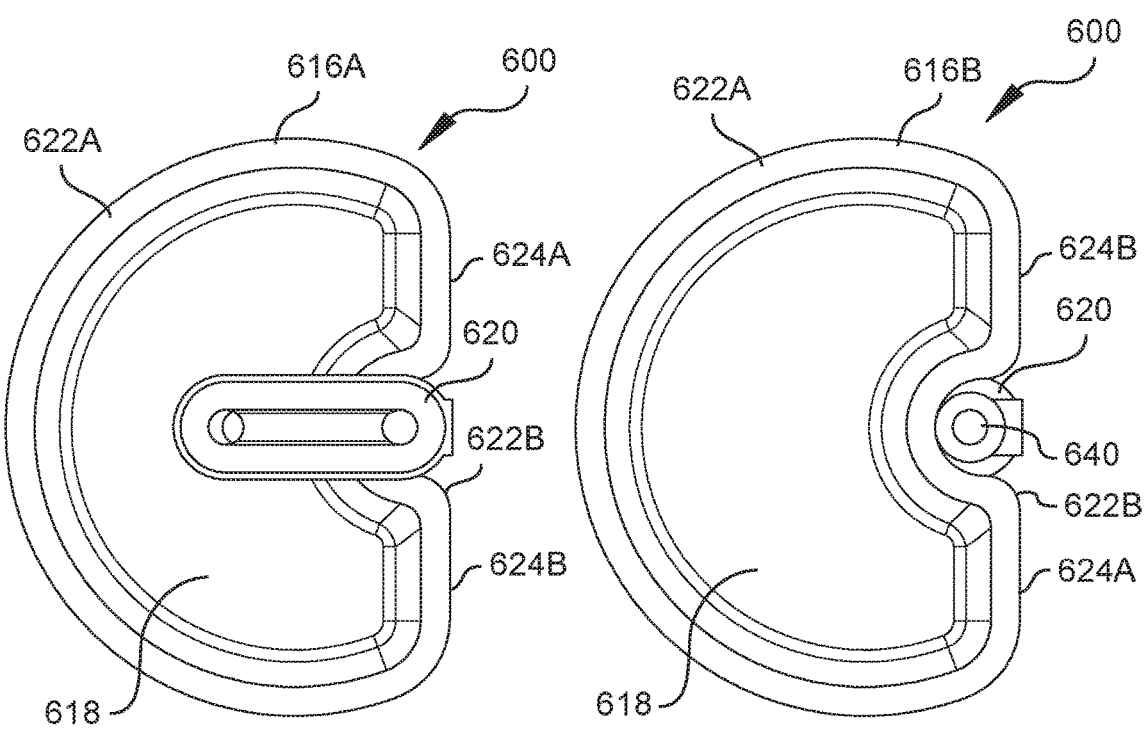
FIG. 45 is a top down view of one embodiment of a reservoir assembly.
FIG. 46 is a bottom up view of the reservoir assembly of FIG. 45.
Figure 47:
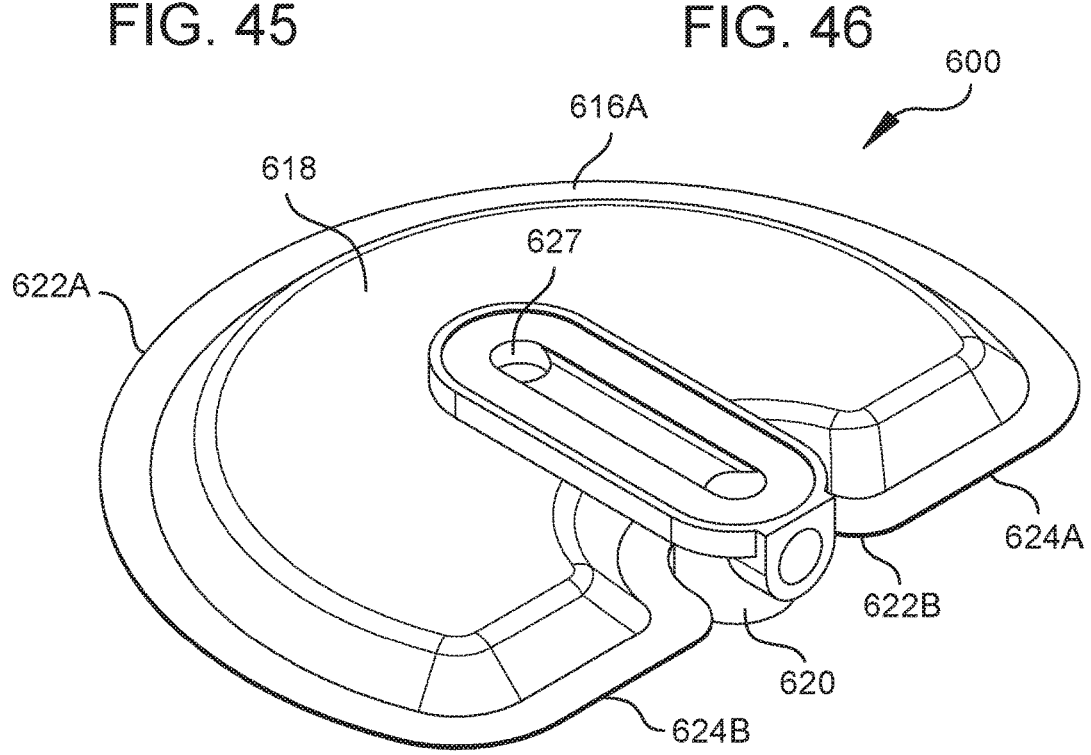
FIG. 47 is a perspective view of the reservoir assembly of FIG. 45.

Referring now also to FIGS. 36-41 an example reservoir assembly 400 is depicted. The example reservoir assembly 400 includes the port connector 120 described in relation to FIGS. 9-16. The perimeter edge of the example reservoir assembly 100 includes a number of contoured, round, or arcuate segments 422A-C and a number of substantially flat segments 424A-C. In the example embodiment, segments 422A, 424B, 424C, 422B, 422C form a "C" like shape perimeter edge. Flat segment 424A extends in a direction perpendicular to flat segments 424B, C and closes off the open end of the "C" like shape. As a result, the exemplary reservoir assembly 400 has a "D" shaped footprint. The edge defined by segment 422A may be an arc which is or is nearly semi-circular (about 160° arc in the example). Arcuate segments 422B, C are swept over a relatively small radius such that the span of flat segment 424A extends about 70%-85% (e.g. 75% or more) of the distance separating flat segments 424B, C. Another "D" shaped reservoir assembly 500 including port connector 320 (see, e.g., FIGS. 28-35) is depicted in FIGS. 42-44. This reservoir assembly 500 may be constructed as described or similar to the reservoir assembly 400.

Still referring primarily to the exemplary reservoir assembly 400 of FIGS. 36-41, some of the segments 422A-C, 424A-C may be defined entirely by the reservoir 418. A portion of flat segment 424A is defined the port connector 120. About 20-15% of the reservoir assembly 400 perimeter is defined by the port connector 120 in the example embodiment. The portion of the port connector 120 external to the reservoir 418 extends away from the reservoir 418 in a manner substantially perpendicular to the segment in which it is located. The port connector 120 extends from an off center position in flat segment 424A, though the port connector 120 may be centrally located in the flat segment 424A in other embodiments (see, e.g., port connector 320 in FIGS. 42-44). With the exception of the placement of port connector 120, the reservoir assembly 400 is symmetrical about its medial plane.

Figure 39:
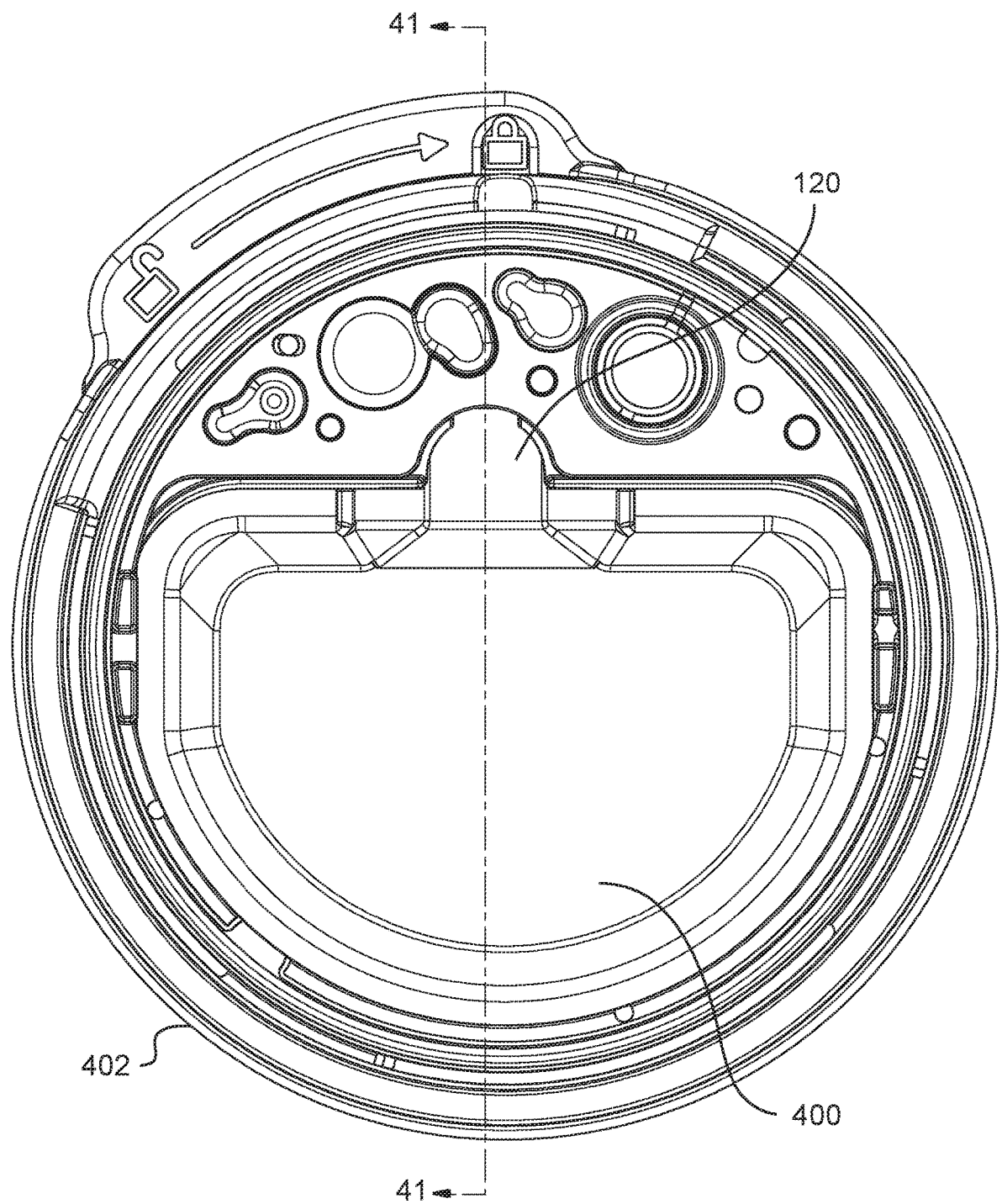
FIG. 39 is a top down view of the reservoir assembly of FIG. 36 installed in an example disposable housing assembly.

The example reservoir assembly 400 is shown installed within an exemplary disposable housing assembly 402 in FIGS. 39-40. When installed in the disposable housing assembly 402, the port connector 120 may cooperate with a port interface structure to establish a sealed fluid communication channel between the reservoir assembly 400 and various fluid pathways within the disposable housing assembly 402. This interaction may be as described elsewhere in the specification and is shown in FIG. 41, a cross-sectional view taken at line 41-41 of FIG. 39. In alternative embodiments, a needle may facilitate fluid connection between the reservoir assembly and the various fluid pathways of the disposable housing assembly 402.

Referring now also to FIGS. 45-51 another example reservoir assembly 600 is depicted. The example reservoir assembly 600 includes a reservoir 618 and a port connector 620. As shown, the reservoir assembly 600 includes a number sides. The perimeter edge of the example reservoir assembly 600 includes a number of contoured, round, or arcuate segments 622A, B and a number of substantially flat segments 624A, B. In the example embodiments, the reservoir 618 is "C" like in shape. The portion of the port connector 620 defining the outlet 640 is disposed in the open end or region of the "C" like shape of the reservoir 618. The port connector 620 is oriented at an angle which is substantially perpendicular to flat segments 624A, 624B of the reservoir 618.

In the example, the interior volume of the reservoir 618 is completely defined by the sheets 616A, B of the reservoir 618. The port connector 620 does not define part of an edge wall of the interior volume of the reservoir 618. The port connector 620 is located entirely external to the reservoir 618. In the example embodiment, the port connector 620 is coupled to an exterior face (e.g. top face) of the reservoir 618. By locating the port connector 620 externally to the reservoir 618, the reservoir 618 may be more free to collapse in a manner where any bunching, folding, crinkling, etc. of the reservoir 618 material is mitigated. In return, this may help to prevent trapping of valuable fluid within pockets in the reservoir assembly 600 when the reservoir assembly 600 is in a collapsed state.

Figure 48:
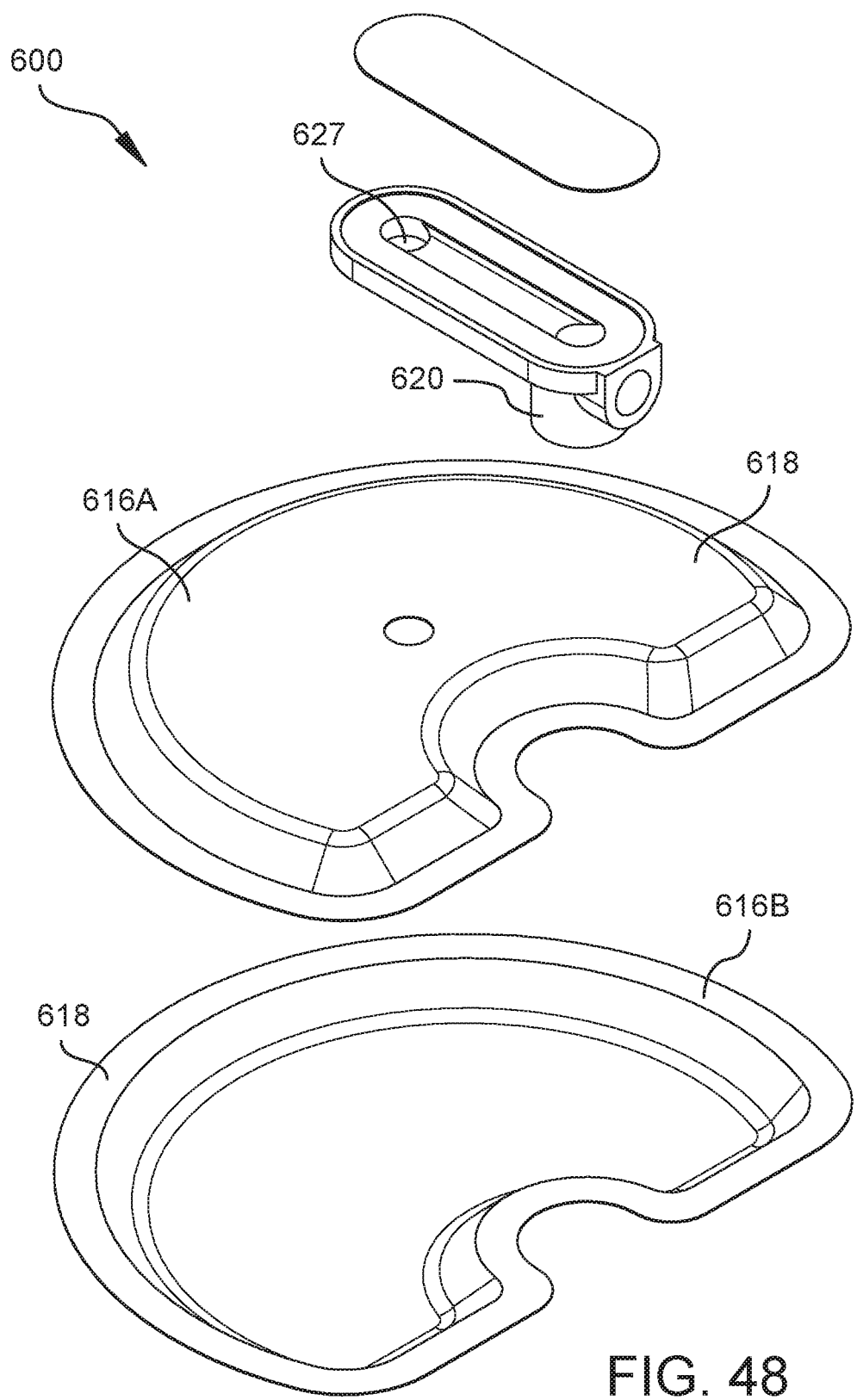
FIG. 48 is an exploded view of the reservoir assembly of FIG. 45.

Referring now also to FIG. 48, the reservoir assembly 600 is shown in an exploded view. As shown, the reservoir 618 face to which the port connector 620 is coupled may include an orifice or pass-through 619. This orifice 619 may be created via a cutting or material removal process (e.g. a mechanical process such as via punch or drill). Alternatively, the orifice 619 may be created during formation of the sheet 616A in which it is included. The port connector 620 may include a reservoir access channel 627 which may align with the axis of the pass-through. Once aligned, the port connector 620 may be attached to the reservoir 618 via any suitable process such as heat bonding or ultrasonic welding.

As shown, a cover plate 623 may also be included. The cover plate 623 may couple to the rest of the port connector 620 body and form a seal over one or more fluid channel in the port connector 620. In the example embodiment, the cover plate 623 may be coupled to a top face of the port connector 620 to seal the inlet 642, reservoir access channel 627 and common fluid channel 646 from the surrounding environment. The cover plate 623 may, in some embodiments, be clear and coupled to the rest of the port connector 620 via a laser weld. At least the area of the port connector 620 to which the cover plate is attached may be made of a black material to facilitate laser welding of the cover plate 623.

Figure 49:
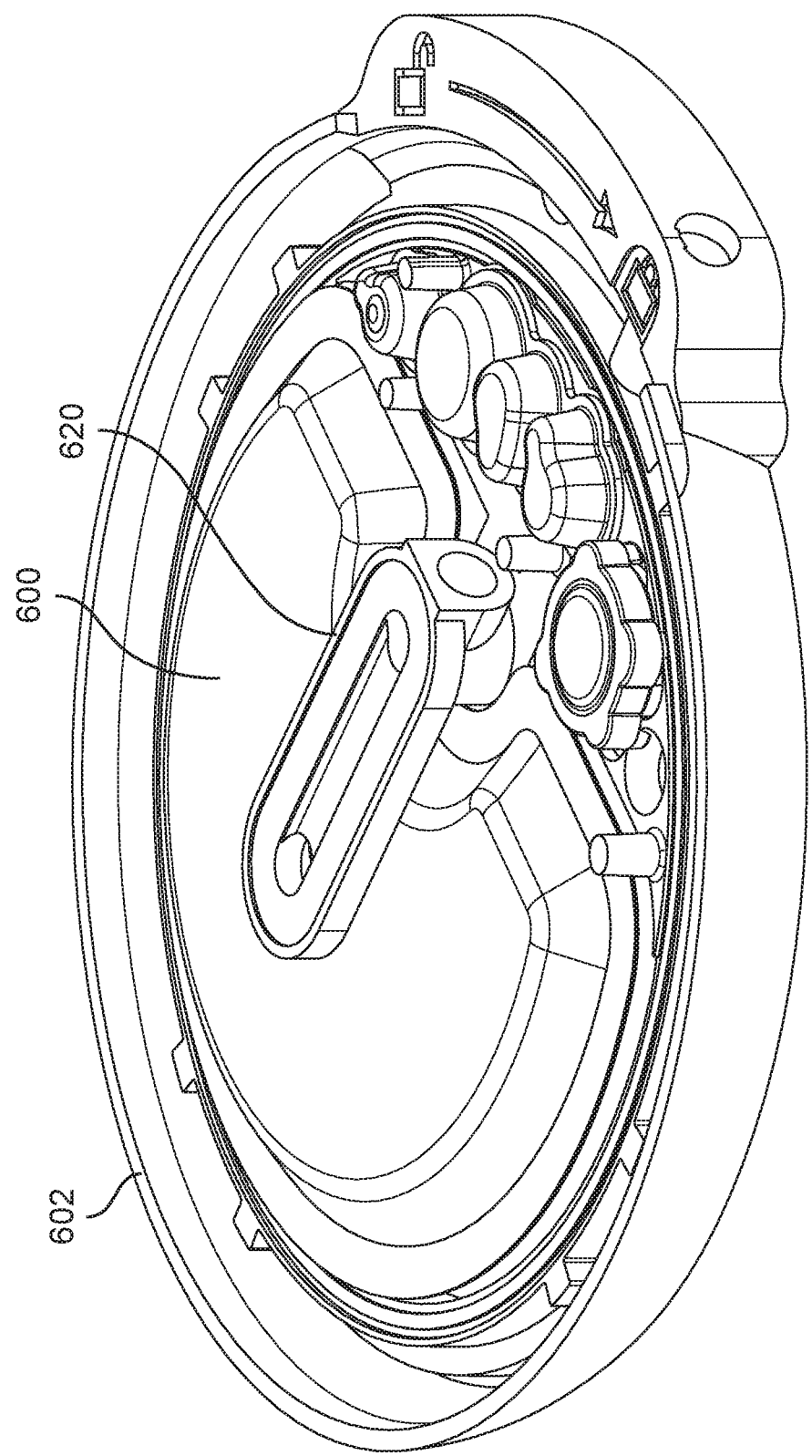
FIG. 49 is a perspective view of the reservoir assembly of FIG. 45 installed in an embodiment of a disposable housing assembly.
Figure 50:
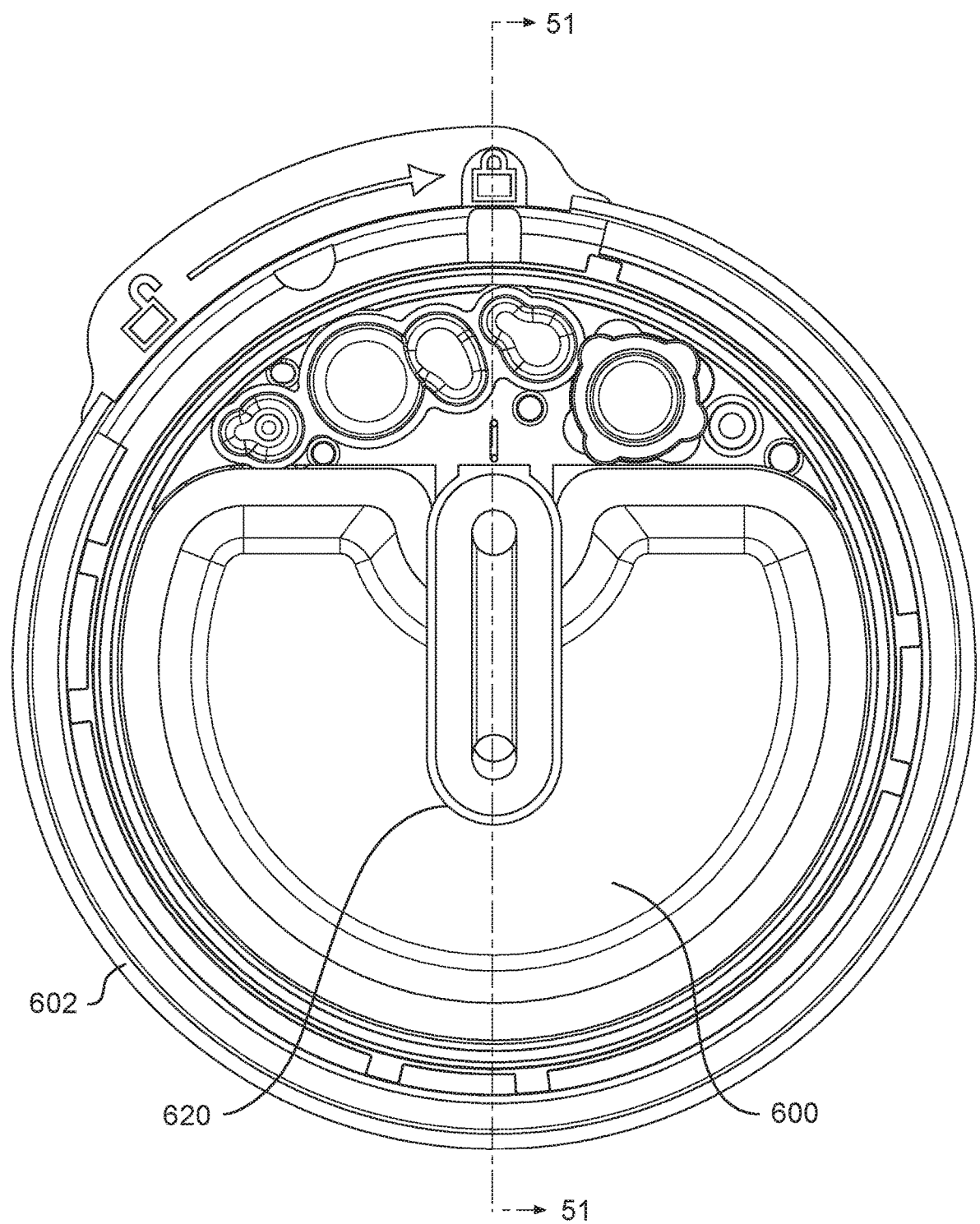
FIG. 50 is a top down view of the reservoir assembly of FIG. 45 installed in an embodiments of a disposable housing assembly.
Figure 51:
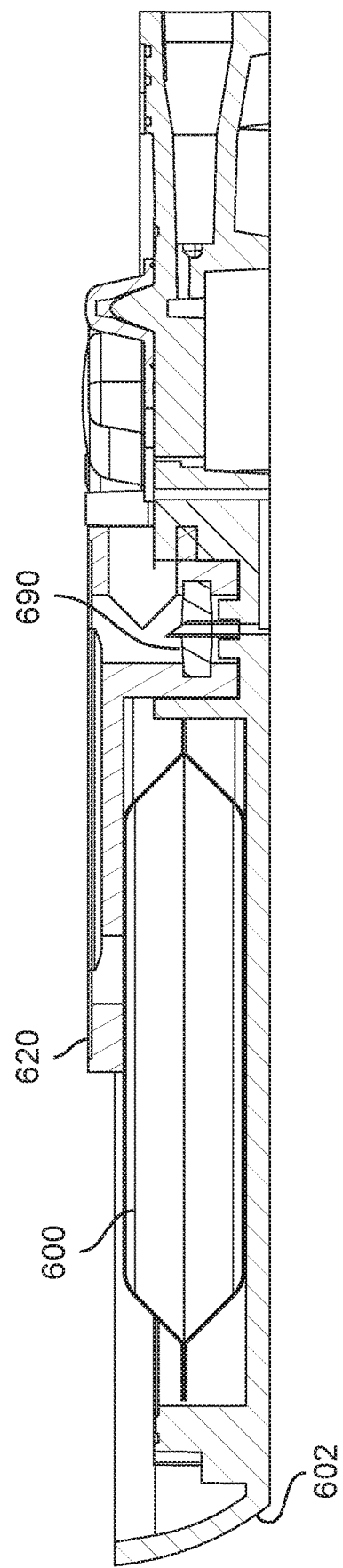
FIG. 51 is a cross sectional view taken at line 51-51 of FIG. 50.
Figure 52:
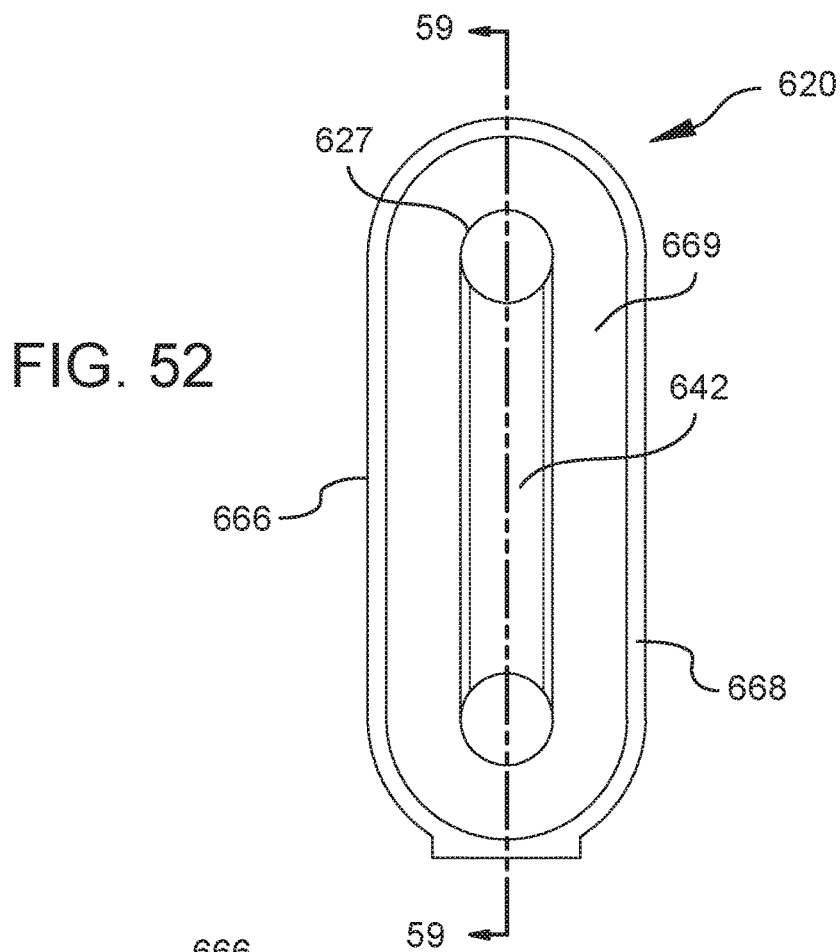
FIG. 52 is a top down view of an embodiment of a port connector.
Figure 53:
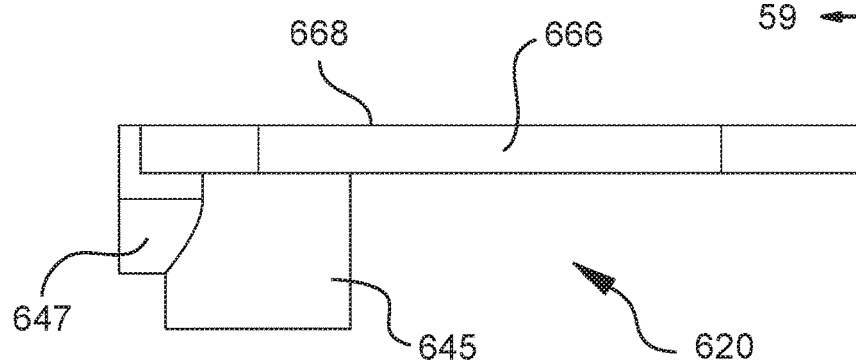
FIG. 53 is a side view of the port connector of FIG. 52.
Figure 54:
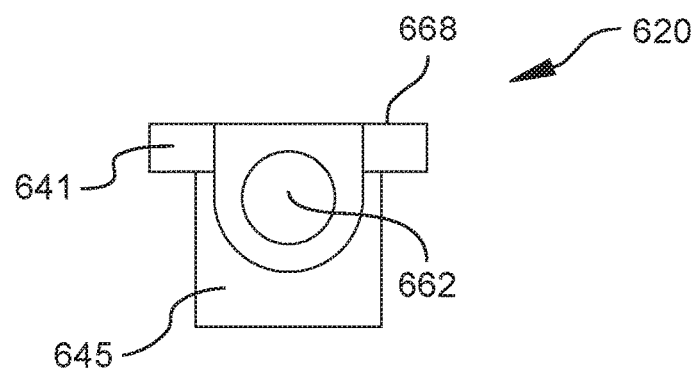
FIG. 54 is a front view of the port connector of FIG. 52.
Figure 58:
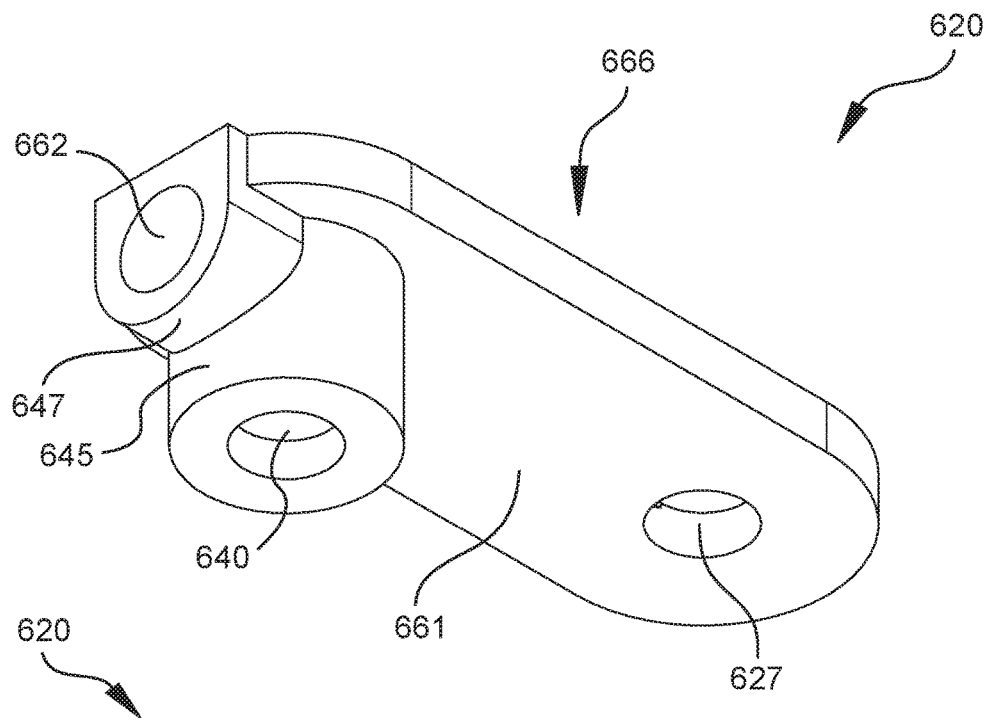
FIG. 58 is a perspective view of the port connector of FIG. 52.
Figure 59:
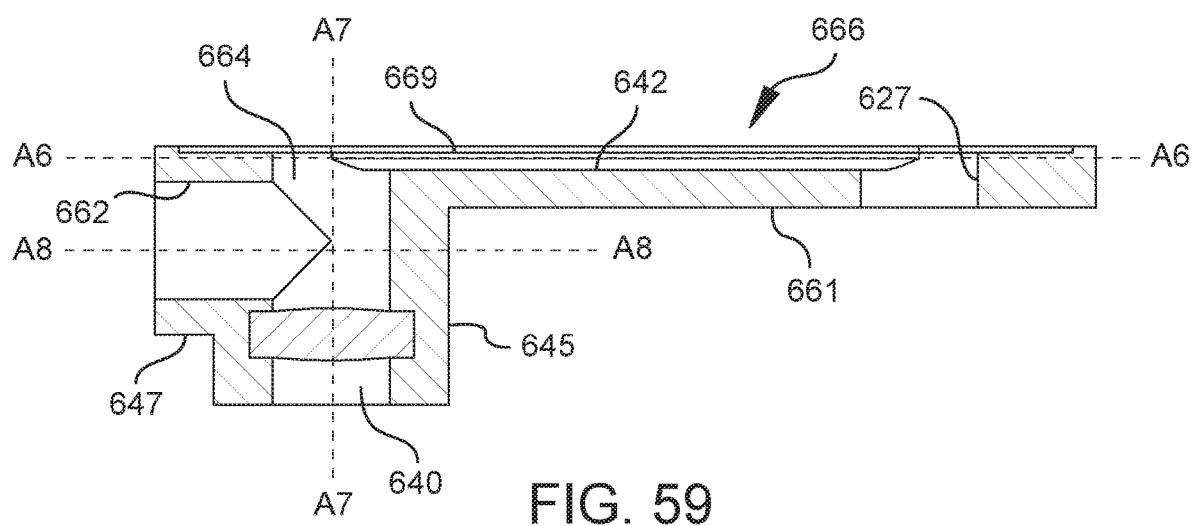
FIG. 59 is a cross sectional view taken at line 59-59 of FIG. 52.
Figure 60:
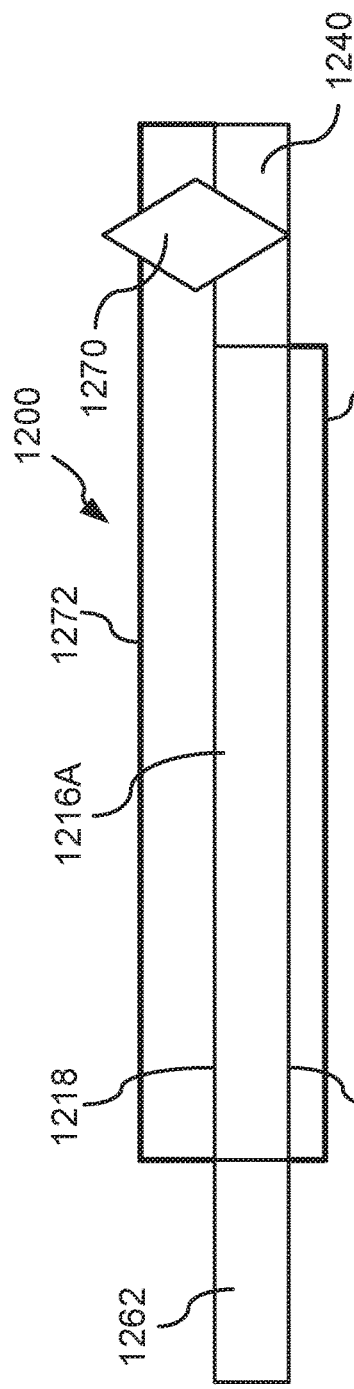
FIG. 60 is a view of one embodiment of a reservoir assembly in an unfilled state installed in a disposable housing assembly.

The example reservoir assembly 600 is shown installed within an exemplary disposable housing assembly 602 in FIGS. 49-50. When installed in the disposable housing assembly 602, the port connector 620 may cooperate with a port interface structure to establish a sealed fluid communication channel between the reservoir assembly 600 and various fluid pathways within the disposable housing assembly 602. Alternatively, the port connector 620, may interface with a needle. An embodiment including such a needle 690 is depicted in FIG. 51, a cross-sectional view taken at line 51-51 of FIG. 49.

Referring now also to FIGS. 52-59, a number of views illustrating the example port connector 620 of FIGS. 45-51 are depicted. The cover plate 623 (see FIG. 51) is not depicted so as not to obscure certain features of the illustrations. As shown, the example port connector 620 includes an inlet 642 which is in communication with the reservoir access channel 627. The port connector 620 also includes a delivery port or outlet 640 through which fluid contained in interior volume of the reservoir assembly 600 may exit the reservoir assembly 600. A filling port 662 may also be included in the port connector 620. The filling port 662 may allow for the reservoir assembly 600 to be filled with a fluid such as insulin or another medicament.

In the example embodiment, the inlet 642, outlet 640, and filling port 662 are all in communication with a common fluid channel or chamber 664 (best shown in FIG. 59) included in the connection port 620. Each of the inlet 642, outlet 640, and filling port 662 are in communication with the common fluid channel 664 in the example embodiment. Fluid traveling between any of the inlet 642, outlet 640, and filling port 662 may pass through the common fluid channel 664 en route to its destination.

In the example embodiment, the inlet 642 extends substantially along an axial direction defined by axis A6. The outlet 640 extends substantially along an axial direction defined by axis A7. The filling port 662 extends substantially along an axial direction defined by axis A8. The port connector 620 is substantially symmetric about its vertical (a plane parallel to, or depending on the embodiment containing, axis A7) medial plane.

In various embodiments, axis A7 may be substantially perpendicular to axis A8 and A6. These axes A6-A8 may be oriented within the same plane. A portion of the common fluid channel 664 may also be disposed within the plane of axes A6-A8. Axis A6 may be substantially parallel but not coaxial to axis A8. Such an arrangement allows the port connector 620 to be made in a small form factor with fluid pathways of the inlet 642, outlet 640, and filling port 662 being relatively large in cross-sectional area. In the example embodiment, the width (in a direction perpendicular to axis A6 and A7) of the port connector 620 is about three times the diameter of the outlet 640.

Still referring also to FIGS. 52-59, in some embodiments, a wall 645 surrounding axis A7 may be included and may extend substantially parallel to the direction of axis A7. The wall 645 may serve to define the outlet 640 as well as at least a portion of the common fluid channel 664. The wall 645 may be annular and may include a thicker head portion 641 on the end of the wall 645 opposite the outlet 640. The filling port 662 may extend through the wall 645 and to the common fluid channel 664. In some embodiments, a second wall 647 surrounding axis A8 may project from the wall 645 and may extend along the direction of axis A8. The second wall 647 may define a portion of the filling port 662.

As shown, the example port connector 620 also includes a branch member 666. The branch member 666 may extend in the direction of axis A8 and may be disposed at or near the top end (the end opposing outlet 640) of the port connector 620. A face of the branch member 666 may serve as a coupling structure which provides a surface or surfaces onto which the reservoir 618 may be bonded or welded during assembly of a reservoir assembly 600. In the example embodiment, the port connector 620 includes a coupling surface 661 which is disposed on the underside of the example branch member 666. In the example embodiment, the coupling surface 661 is substantially planar. This may help to allow the reservoir 618 to collapse optimally with minimal trapping of fluid pockets.

The inlet 642 may be defined in a portion of the branch member 666 as well. In the example embodiment, the inlet 642 is open on one side and may defined as a trough which is recessed into a top face 668 of the branch member 666. A second recess 669 may also be recessed into the top face 668 of the branch member 666. The second recess 669 may be positioned to surround or encircle the inlet 642 may be recessed to a lesser depth. Referring now also to FIG. 51, the second recess 669 may be sized to accept the cover plate 623. The second recess 669 may recessed to a depth which is sufficient to cause the top of the cover plate 623 to be even with or nearly even with the top face 669 of the branch member 666.

Referring now also to FIGS. 60-65, in certain embodiments, a port connector like those described elsewhere herein may not be included. Alternatively, a port connector may be included, however, a fill port in the port connector may be absent. In such embodiments, a reservoir assembly 1200 may include a filling extension 1262. The filling extension 1262 may be attached to a portion of the reservoir 1218 or may be an integral part of the reservoir 1218. The fill extension 1262 may, for example, be constructed from an extension of the flexible sheeting 1216A, B from which the reservoir 1218 is made. An outlet portion 1240 may also be included. The outlet portion 1240 may be attached to the reservoir 1218 (e.g. included in a port connector) or may be an integral part of the reservoir 1218. The outlet portion 1240 may, for example, be constructed from an extension of the sheeting 1216A, B from which the reservoir 1218 is made. A reservoir assembly 1200 may also include an occluder 1270. Any variety of occluder 1270 may be used and may pinch, clamp, crimp, crush, kink or otherwise prevent flow through the outlet portion 1240. Prior to use, the occluder 1270 may be actuated from an occluding state to an open state manually by the user. This may open a fluid flow path through the outlet 1240. Alternatively, an actuator may interact with the occluder 1270 and serve to transition the occluder from the occluding state to the open state when actuated. The occluder 1270 may be, but is not limited to, any of those described herein. Depending on the embodiment, the occluder 1270 may interact or engage with a cover member 1272 (shown in FIG. 60), to maintain, lock, or latch the occluder 1270 in an occluding state. This interaction may be interrupted either manually or via actuation of an actuator to bring the occluder 1270 into an open state. The occluder 1270 may interact or engage with a cover member 1272 to maintain, lock, or latch the occluder 1270 in an open state.

Figure 61:
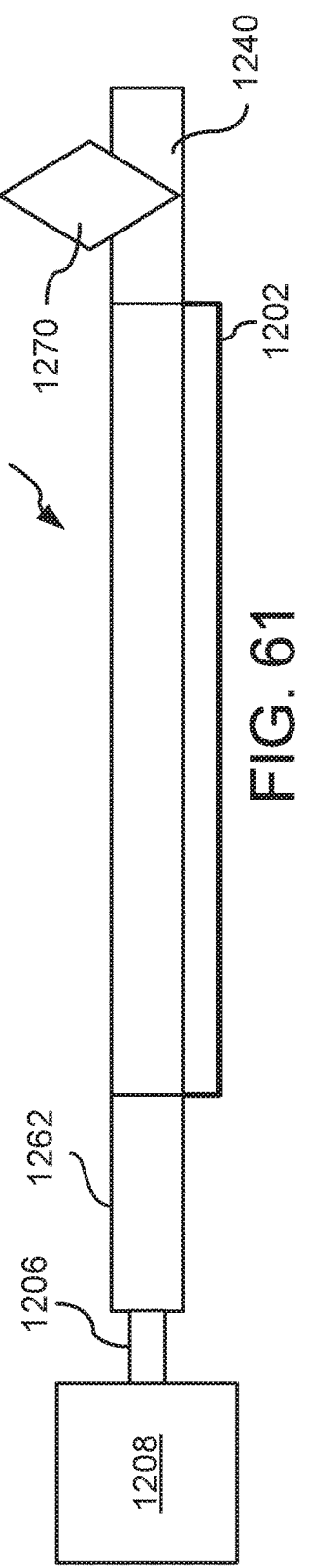
FIG. 61 is a view of one embodiment of a reservoir assembly in an unfilled state installed in an embodiment of a disposable housing assembly and in communication with an embodiment of a filling assembly.

Referring now also to FIG. 61, the reservoir assembly 1200 may be manufactured in an empty state. As shown, the reservoir assembly 1200 may be pre-assembled into the disposable housing assembly 1202 in an empty state. The outlet portion 1240 of the reservoir assembly 1200 may be coupled to the various fluid pathways (described elsewhere herein and in any one or more of the applications and/or patents incorporated herein by reference) of the disposable housing assembly 1202. The occluder 1270 may be in an occluding state and disrupt fluid communication between the interior volume of the reservoir assembly 1200 and the rest of the disposable housing assembly 1202. The reservoir assembly 1200 may be brought into communication with a source reservoir 1208 via a filling assembly 1206. A nozzle or similar fitting of the filling assembly 1206 may, for example, be introduced to the fill extension 1262. The fill assembly 1206 may then dispense fluid from the source reservoir 1208 into the reservoir 1218. As the occluder 1270 is in the occluding state, fluid may be prevented from exiting the reservoir 1218 via the outlet portion 1240.

Figure 62:
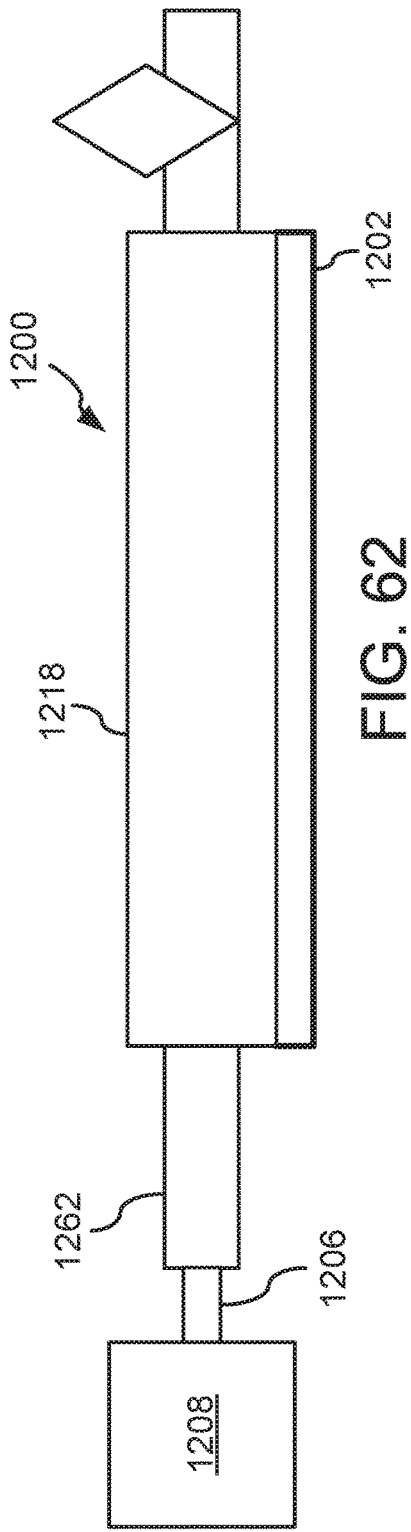
FIG. 62 is a view of one embodiment of a reservoir assembly in a filled state installed in one embodiment of a disposable housing assembly.
Figure 63:
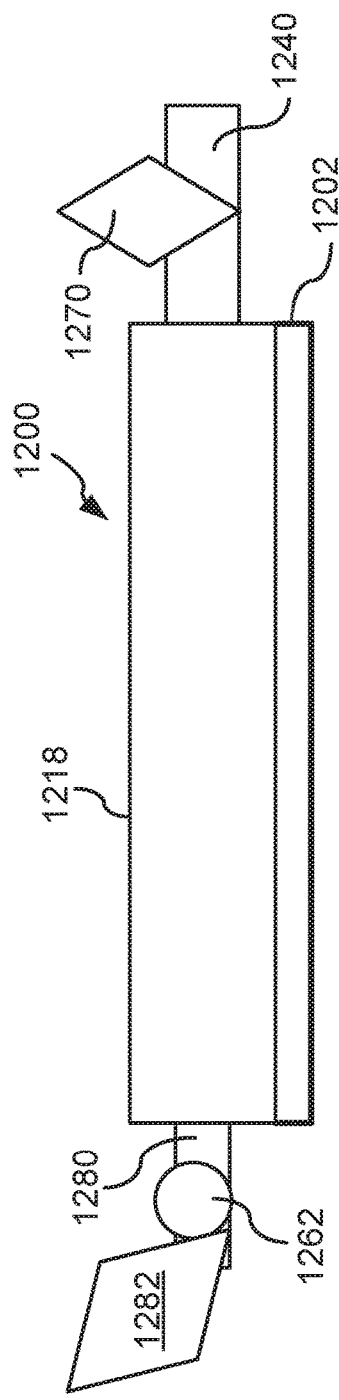
FIG. 63 is a view of one embodiment of a reservoir assembly in one embodiment of a disposable housing assembly with one embodiment of a fluid displacement tool and sealing assembly.

After an appropriate or predefined amount of fluid is dispensed, the reservoir 1218 may be in a filled state as depicted in FIG. 62. The filling assembly 1206 may be withdrawn and the fill extension 1262 may then be sealed closed. Depending on the fluid contained in the reservoir 1218, it may be desirable to displace fluid into the reservoir 1218 from the fill extension 1262 before creating a seal. Referring primarily to FIG. 63 a fluid displacement tool 1280 may be used to displace fluid from the fill extension 1262 into the reservoir 1218. The fluid displacement tool 1280 may be a squeegee, roller(s), sweeping arm(s), peristaltic type mechanism, etc. which may be dragged or otherwise actuated from the open, distal end of the fill extension 1262 toward the reservoir 1218. The amount of fluid displaced from the fill extension 1262 into the reservoir 1218 during this operation may substantially bring the reservoir 1218 to its maximum capacity. Alternatively, the fluid displacement tool 1280 may be displaced in the opposite direction from a point proximal to the reservoir 1218 toward the distal, open end of the fill extension 1262. Fluid may then be displaced out of the fill extension 1262 into a collection reservoir (not shown).

Figure 64:
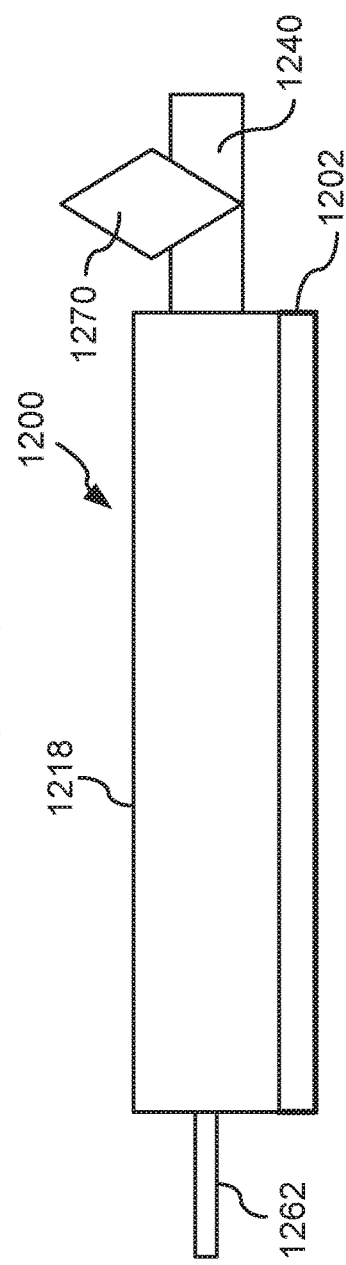
FIG. 64 is a view of one embodiment of a reservoir assembly in one embodiment of a disposable housing assembly in a filled and sealed state.
Figure 65:
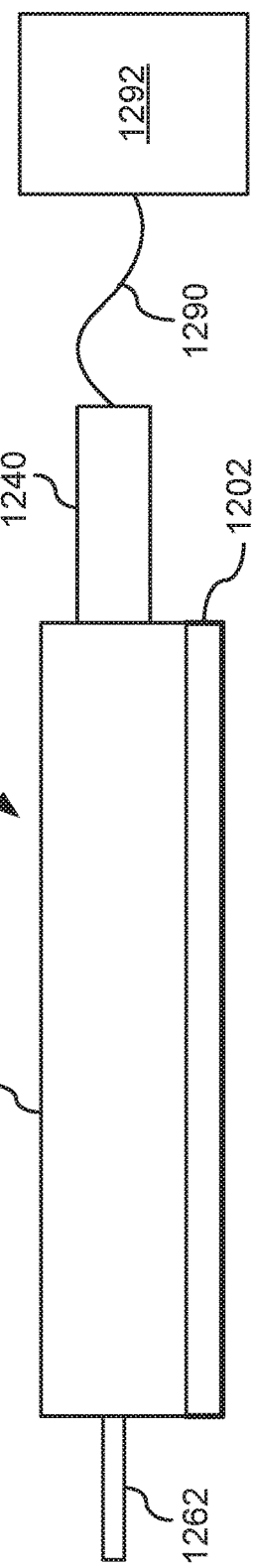
FIG. 65 is a view of one embodiment of a reservoir assembly where an occluder has been removed and the reservoir is in fluid communication with a user/patient.

Referring also to FIG. 63, after fluid has been displaced from the fill extension 1262 into the reservoir 1218, a seal may be formed to close to the fluid pathway through the fill extension to the interior volume of the reservoir 1218. A sealing assembly 1282 may interact with the fill extension 1262 to generate the seal. The walls of a fluid pathway in the fill extension 1262 may be displaced into contact with one another and bonded together to seal the fill extension closed. A sealed fill extension 1262 is shown in FIG. 64. In certain embodiments, a heat stake may be made to seal the fill extension 1262. In such examples, a portion of the fluid displacement tool 1280 may be kept in place at a location proximal to the reservoir 1218 while the seal is formed. Thus the fluid displacement tool 1280 may act as a heat barrier which helps to prevent heat from the sealing process from being transferred to the fluid which was filled into the reservoir 1218. The fluid displacement tool 1280 may also include a heat sink or be actively cooled to aid in its role as a heat barrier. At least a portion of the fluid displacement tool 1280 may be made of a material which acts as a thermal insulator.

After sealing, the reservoir assembly 1200 may be stored, optionally already installed within a disposable housing assembly 1202, until use. When ready for use, and referring now primarily to FIG. 65, the reservoir assembly 1200 may be installed in a disposable housing assembly 1202, if not already installed. An infusion set 1290 may be coupled to the disposable housing assembly 1202 (if not already coupled). The occluder 1270 may be removed or actuated from the occluding state to a flow permitting state. The infusion set 1290 may be primed and coupled to a patient 1292. Fluid may then be selectively dispensed from the reservoir assembly 1200 to provide therapy for the patient 1292.

Figure 66:
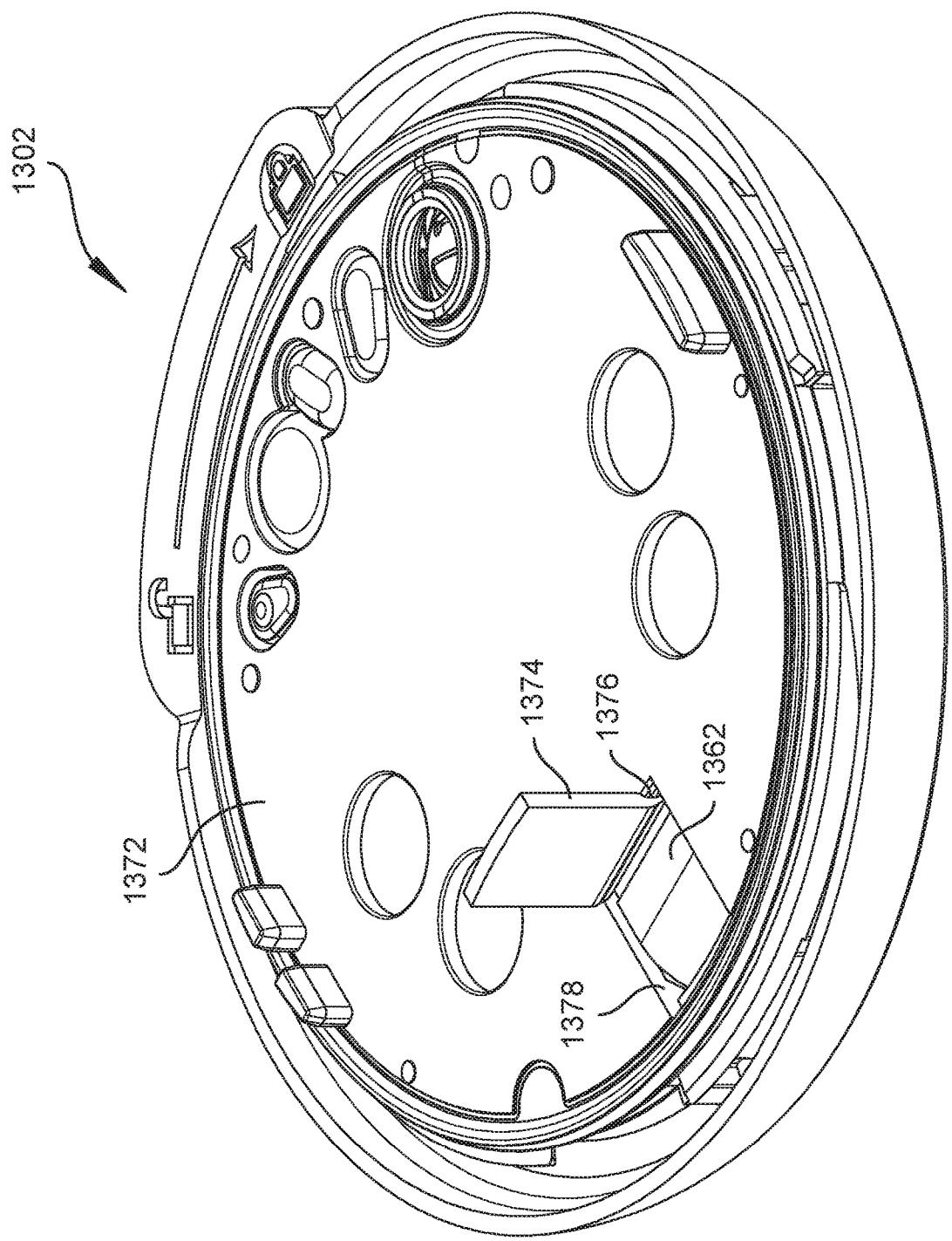
FIG. 66 is a perspective view of one embodiment of a disposable housing assembly having a cover with a hatch.
Figure 67:
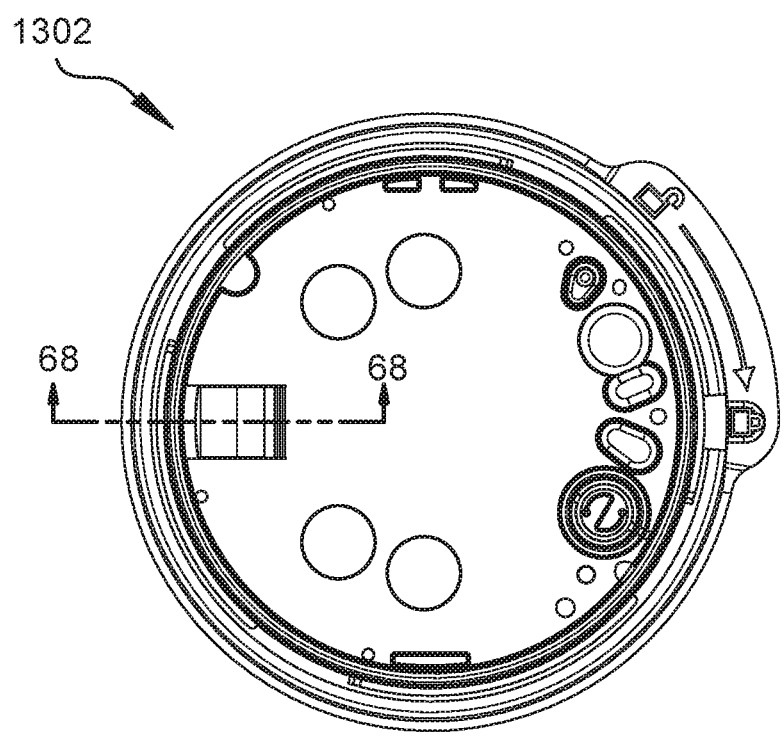
FIG. 67 is a top down view of the embodiment of a disposable housing assembly of FIG. 66.
Figure 68:
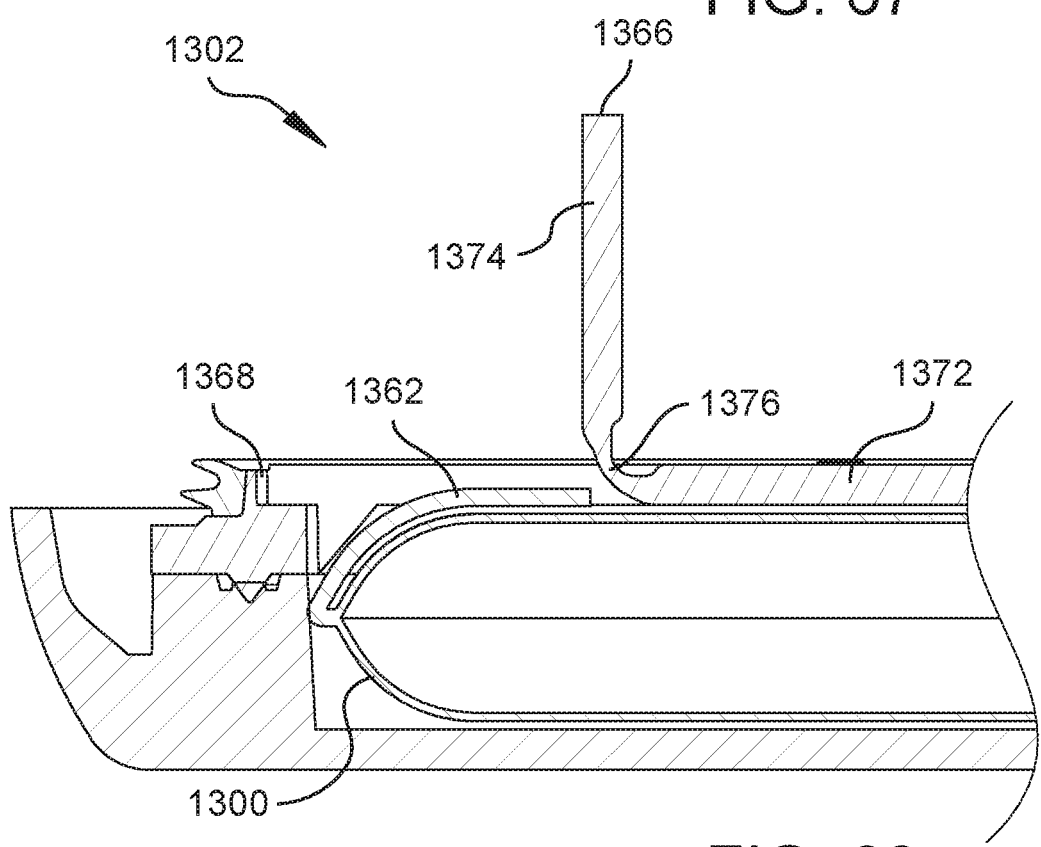
FIG. 68 is a cross sectional view taken at line 68-68 of FIG. 67.

Referring now also to FIGS. 66-68, an exemplary disposable housing assembly 1302 with an installed reservoir assembly 1300 is shown. As shown, the disposable housing assembly 1302 includes a cover member 1372 having a hatch 1378 with a flap 1374. The flap 1374 may be actuated between an open position and a closed position. The flap 1374 may be hingedly or pivotally coupled to the cover member 1372. In the example embodiment, a living hinge 1376 is provided between the flap 1374 and the remainder of the cover member 1372.

When in the open position 1374 (shown), access to the reservoir assembly 1300 through the hatch 1378 may be possible. Such an arrangement may be used in embodiments where the reservoir assembly 1300 is filled after being installed in a disposable housing assembly 1302. Before the reservoir assembly 1300 is filled, the fill extension 1362 may extend through the hatch 1378. A filling assembly 1206 (see, e.g. FIG. 61) may then easily interface with the fill extension 1362 such that fluid may be dispensed into the reservoir assembly 1300. A fluid displacement tool 1280 (see, e.g. FIG. 63) and sealing assembly 1282 (see, e.g. FIG. 63) may also engage the fill extension 1362 through the hatch 1378. Once sealed, the fill extension 1362 may be folded over into the hatch 1378 as shown and the flap 1374 may be actuated to the closed position. In some embodiments, the flap 1374 may include at least one catch member (not shown) on an end face 1366 of the flap (e.g. opposite the living hinge 1376). The catch member(s) may engage a latch feature on the wall 1368 of the disposable housing assembly 1302 or cover member 1372 when the flap has been displaced into the closed position. Once engaged, the catch member and latch feature may inhibit displacement of the flap 1374 back into the open position. Such an arrangement may be particularly useful in single use applications.

Figure 69:
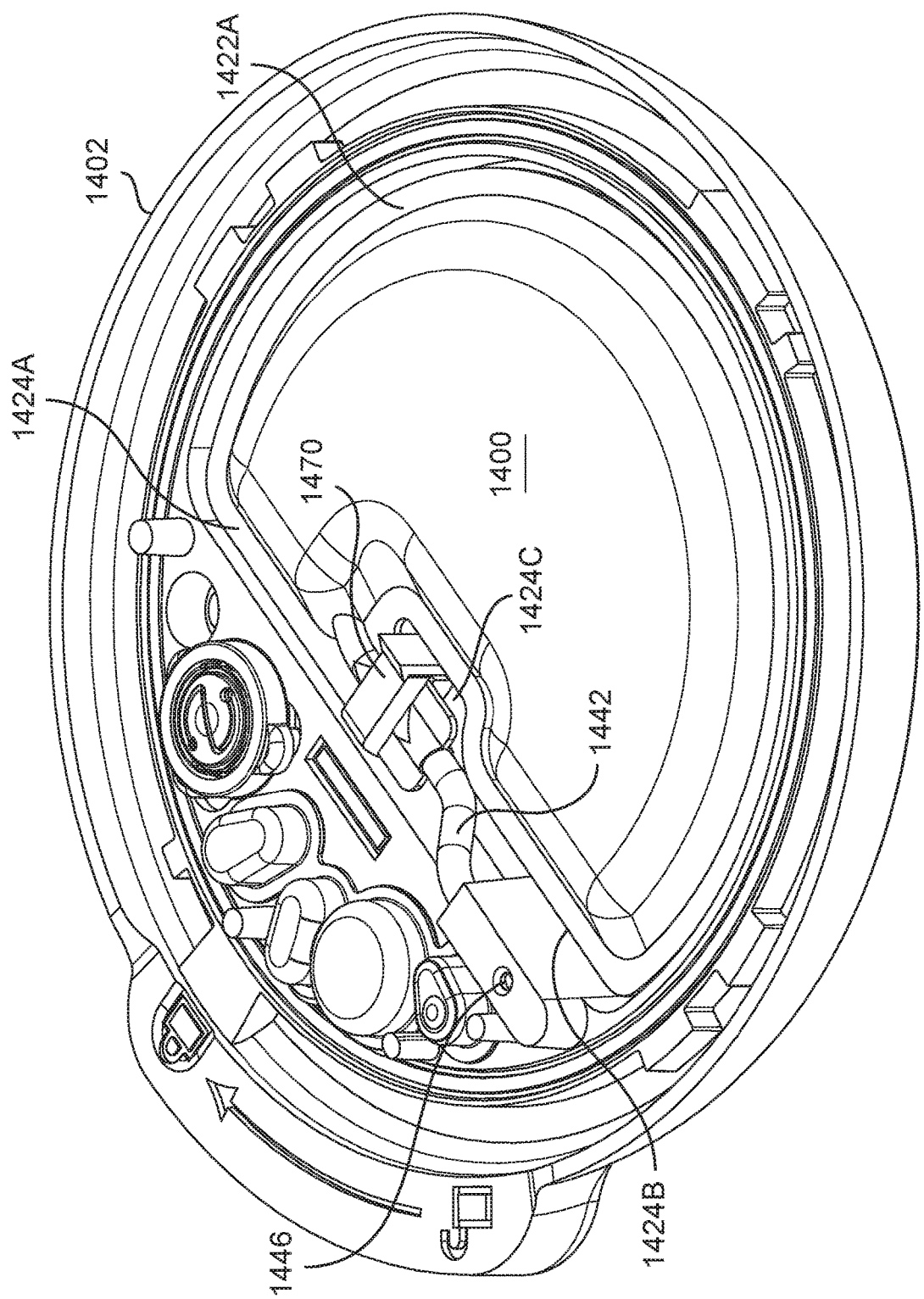
FIG. 69 is a perspective view of one embodiment of a reservoir assembly in one embodiment of a disposable housing assembly with an embodiment of a clamp occluder.
Figure 70:
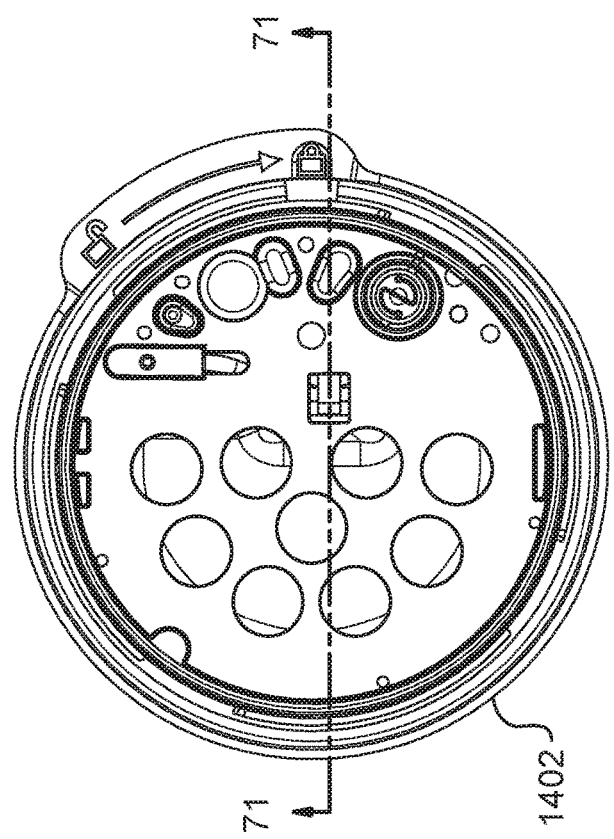
FIG. 70 is a top down view of the embodiment of a reservoir assembly, disposable housing assembly, and occluder of FIG. 69.
Figure 71:
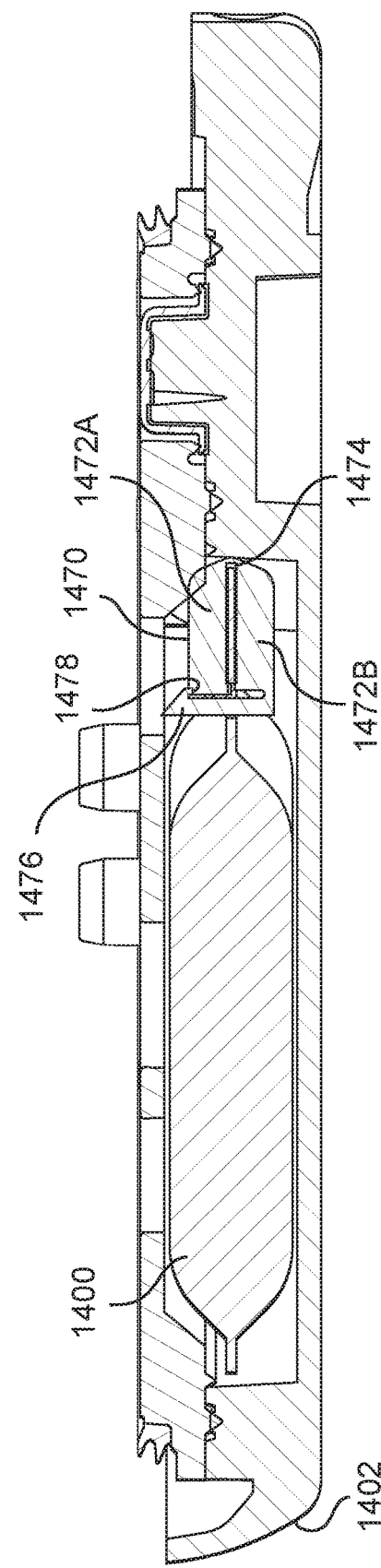
FIG. 71 is a cross-sectional view taken at line 71-71 of FIG. 70.

Referring now also to FIG. 69-71, a number of views of an example reservoir assembly 1400 installed in a disposable housing assembly 1402 are depicted. The reservoir assembly 1400 includes a rounded side 1422A and a number of flat sides 1424A-C. Each of the flat sides 1424A-C extend substantially parallel to one another but are positioned in different planes. The reservoir assembly 1400 includes an outlet portion 1440 extending substantially parallel to the flat sides 1424A-C. In the example embodiment, the outlet portion 1440 is partially defined by flat side 1424A. In the example embodiment, the outlet portion 1440 is attached to a piece of tubing 1442. The tubing 1442 may be glued or otherwise bonded into the outlet portion 1440. The tubing 1442 leads from the outlet portion 1440 of the reservoir assembly 1400 to a connector 1444 in the disposable housing assembly 1402. The tubing 1442 may be glued or otherwise bonded into to the connector 1444. The connector 1444 includes an introduction port 1446 to allow for glue or another bonding agent to be administered into the connector 1444 in order to bond the tubing 1442 into place. The connector 1444 may provide a fluid pathway to various fluid channels and circuitry included in the disposable housing assembly 1402. The tubing 1442 may be entirely disposed on a side of an occluder 1470 proximal to the connector 1444. This may allow for a greater range of tubing 1442 materials to be use as longer term compatibility of the tubing 1442 with the fluid contained in the reservoir assembly 1400 may not be an issue.

As shown, the reservoir assembly 1400 is in a filled state with an occluder 1470 in an occluding state. As best shown in FIG. 71, a cross-section through the occluder 1470, the occluder 1470 may be a clamp. The occluder 1470 includes a first occluding arm 1472A and second occluding arm 1472B. The first and second occluding arms 1472A, B may be connected to one another via a hinge 1474. In the example embodiment, the hinge 1474 is a living hinge. The occluder 1470 may also include a latch arm 1476. The latch arm 1476 includes a latch feature which in the example embodiment is depicted as an undercut 1478. When the exemplary occluder 1470 is in the occluding state, the occluder arms 1472A, B may be brought together around the outlet portion 1440 to clamp the fluid pathway through the outlet portion 1440. When in the occluding state, the occluder arms 1472A, B may be substantially parallel to one another and substantially perpendicular to the latch arm 1476. One of the occluder arms 1472A, B may catch on the underside of the undercut 1478 keeping the occluder 1470 in the occluding state. When ready for use, latch arm 1476 may be actuated (manually or via an actuator) from its resting position (shown) to a deflected position. In the deflected position, the undercut 1478 may be displaced away from the occluder arm 1472A, B such that the occluder arm 1472A, B may freely swing about the hinge 1474. This may allow the occluder 1470 to transition from the occluding state to a flow permitting state.

Figure 72:
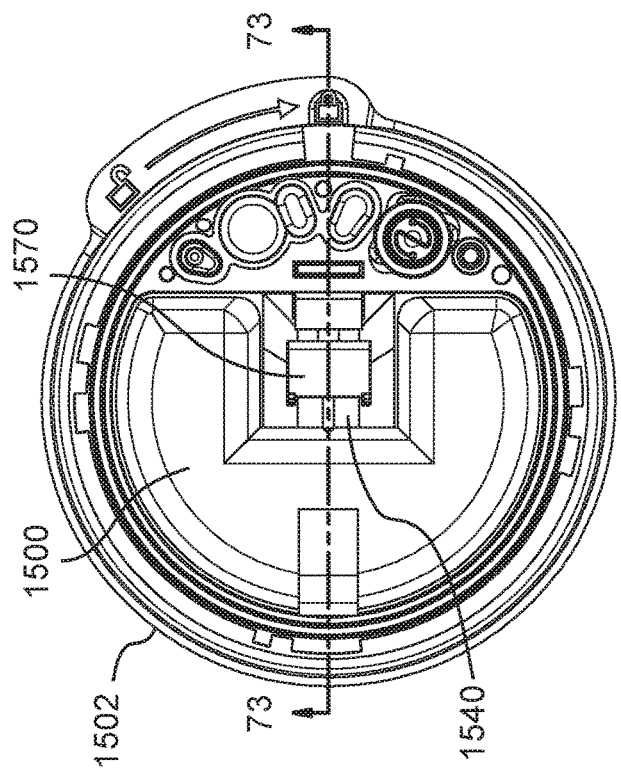
FIG. 72 is a top down view of one embodiment of a reservoir assembly in one embodiment of a disposable housing assembly with an embodiment of a clamp occluder.
Figure 73:
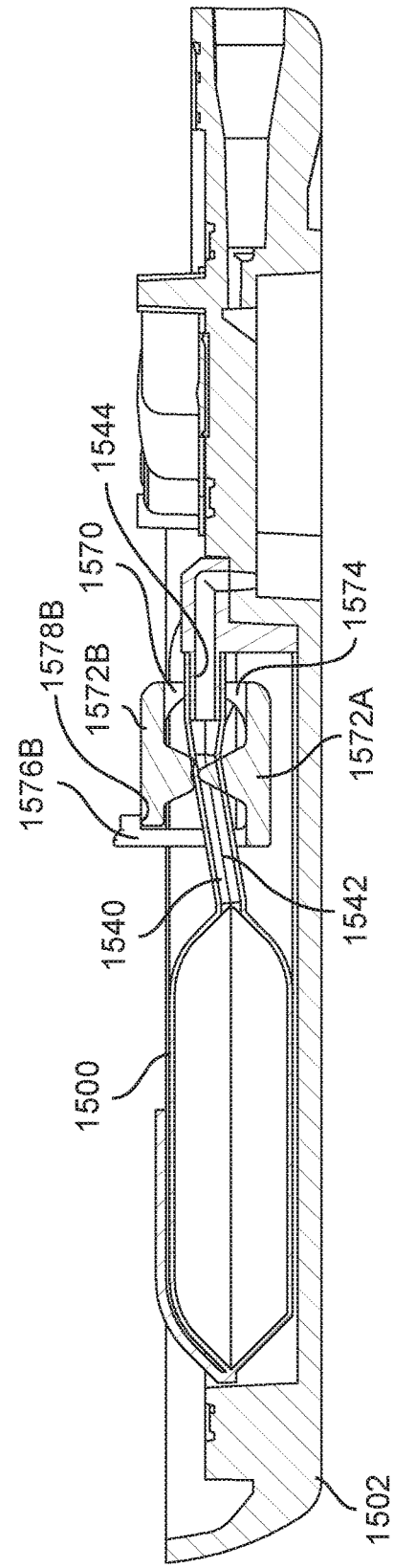
FIG. 73 is a cross-sectional view taken at line 73-73 of FIG. 72.

Referring now also to FIGS. 72-73, another example reservoir assembly 1500 installed in a disposable housing assembly 1502 is depicted. The reservoir assembly 1500 is substantially "E" like in shape. As shown, the interior volume of the reservoir assembly 1500 has a "C" like footprint. An outlet portion 1540 extends from the center of the "C" shape forming the middle projection of the "E". The outlet portion 1540 includes a flow conduit 1542 which may couple to a projection 1544 extending from a connector portion of the disposable housing assembly 1502. As best shown in FIG. 73, an occluder 1570 may be positioned around the outlet portion 1540 in an occluding state so as to block flow through the flow conduit 1542.

Figure 74:
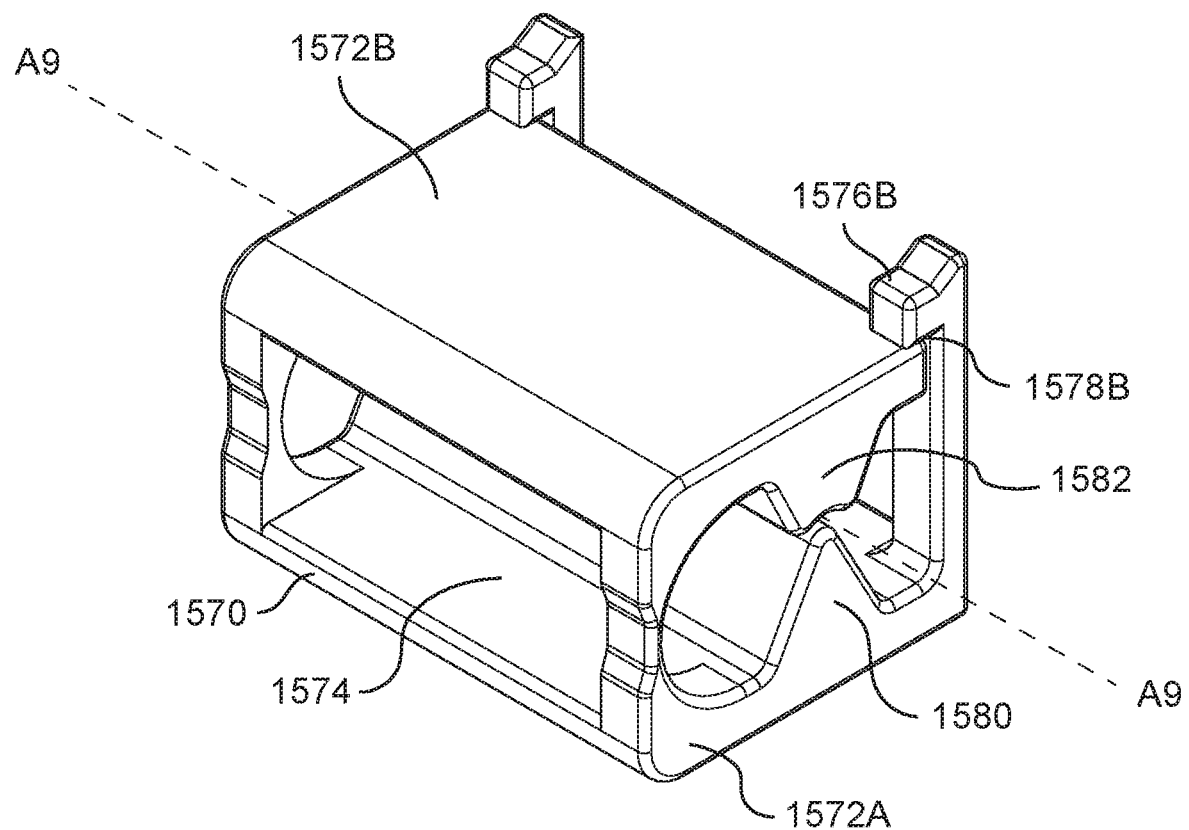
FIG. 74 is a perspective view of one embodiment of a clamp-type occluder.
Figure 75:
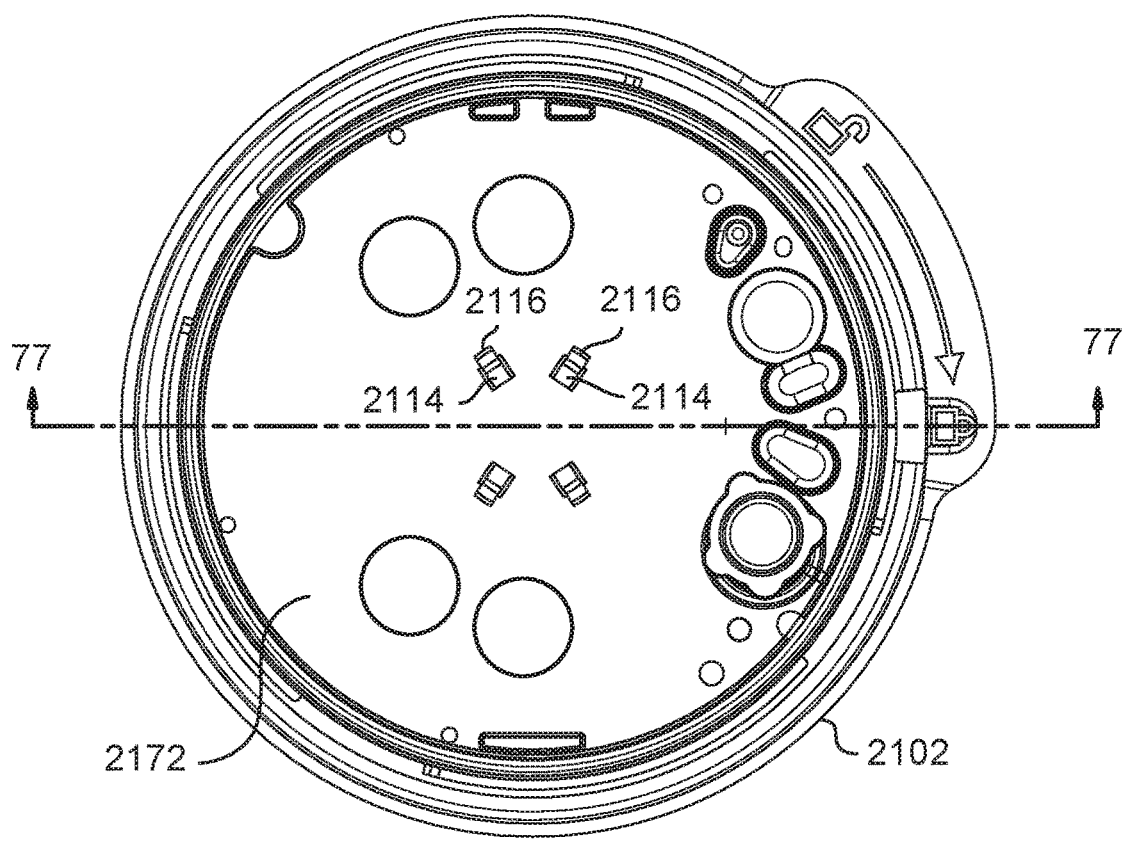
FIG. 75 is a top down view of one embodiment of a disposable housing assembly and an embodiment of a clamp type occluder.
Figure 76:
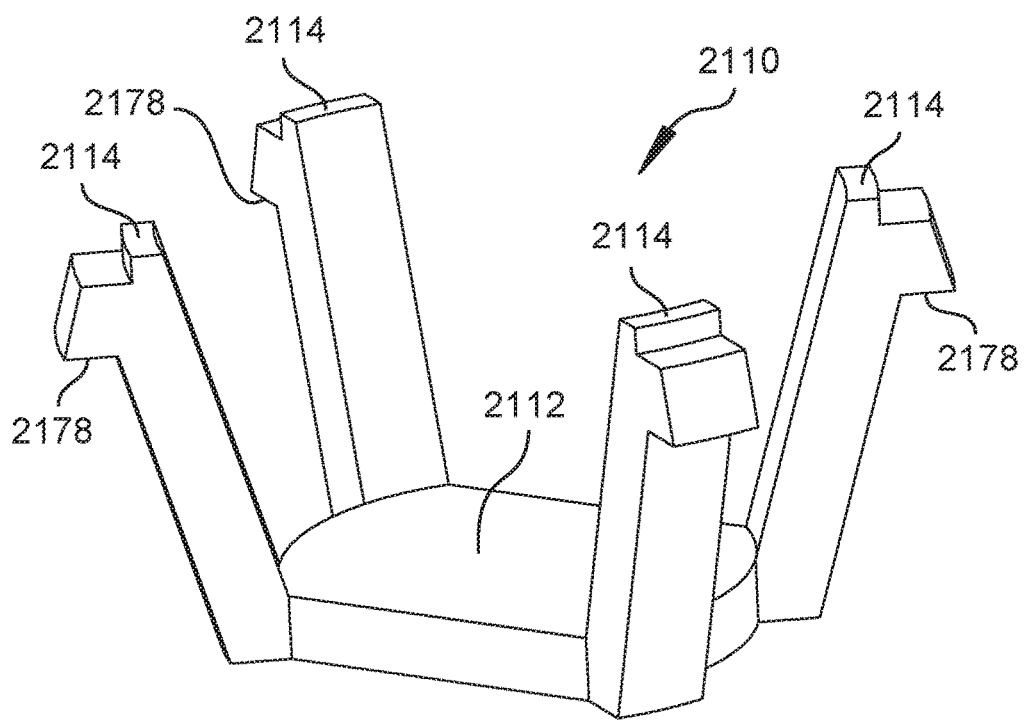
FIG. 76 is a perspective view of one embodiment of a clamp type occluder.

Referring now also to FIG. 73 and FIG. 74, the occluder 1570 includes a central passage 1574 which may be sized to accommodate the outlet portion 1540 of the reservoir assembly 1500. Two occluder arms 1572A, B are also included in the example embodiment. The walls of the central passage 1572 may act as a living hinge about which the occluder arm 1572A, B may pivot. A nub 1580 or similar projection may extend from one of the occluder arms 1572A, B toward an axis A9 of the central passage 1574. A projection 1582 including a recess 1584 sized to accept at least a portion of the nub 1580 may be included on the occluder arm 1572A, B opposite the nub 1580. When in the occluding state, and as best shown in FIG. 73, the flow conduit 1542 may be pressed between the nub 1580 and recess 1584 to clamp the flow conduit 1542 closed.

Still referring primarily to FIGS. 73-74, the occluder 1570 may include latch arms 1576A, B. At least one of the latch arms 1576A, B may include a latch feature. In the example embodiment both of the latch arms 1576A, B include an undercut 1578A, B which serves as the latch feature. When the exemplary occluder 1570 is in the occluding state, the occluder arms 1572A, B may be displaced toward one another to clamp flow conduit 1542 in the outlet portion 1540. When in the occluding state, the occluder arms 1572A, B may be substantially parallel to one another and substantially perpendicular to the latch arms 1576A, B. One of the occluder arms 1572A, B may catch on the underside of the undercuts 1578A, B keeping the occluder 1570 in the occluding state. When ready for use, latch arms 1576A, B may be actuated (manually or via an actuator) from their resting position (shown) to a deflected position. In the deflected position, the undercuts 1578A, B may be displaced away from the occluder arm 1572A, B such that the occluder arm 1572A, B may freely swing to an open position. This may allow the occluder 1570 to transition from the occluding state to a flow permitting state.

Referring now also to FIGS. 75-78, another embodiment of an exemplary occluder 2110 is depicted. The occluder 2110 is depicted alone in FIG. 76 and in an exemplary disposable housing assembly 2102 in FIGS. 75, 77, and 78. As shown, the occluder 2110 includes a platform 2112 and a number of arms 2114 which extend from the platform 2112. Latch features may be present on at least some of the arms 2114. As shown, each of the arms 2114 may include a latch feature. In the example embodiment all of the arms 2114 include an undercut 2178 which serves as the latch feature.

The arms 2114 may project through cutouts 2116 in a cover member 2172 of the disposable housing assembly 2102. The undercuts 2178 of the occluder 2110 may rest on a face of the cover member 2172 keeping the occluder in place in an occluding position. As shown best in the cross section of FIG. 77, when in the occluding state, the platform 2112 occluder 2110 may be held against an occluder bar 2180 on the side of the cover member 2172 opposite the side against which the undercuts 2178 rest. In this state a fluid pathway through the outlet portion of a reservoir assembly (see, e.g., FIG. 60-65) may be pinched closed between the platform 2112 and the occluder bar 2180.

The arms 2114 may be attached to the platform 2112 in a cantilevered manner. To displace the occluder 2110 form an occluding state to a flow permitting state, the arms 2114 may be actuated (manually or via an actuator) inward toward the center of the platform 2112. In a deflected state, the arms 2114 may have been displaced a distance sufficient to allow the undercuts 2178 to no longer rest on the top face of the cover member 2172. The arms 2114 may pass through the cutouts 2116 in the cover member 2172 and the occluder 2110 may fall into the interior of the disposable housing assembly 2102 as shown in FIG. 78. After dropping into the disposable housing assembly 2102, the platform 2112 of the occluder 2110 may be a greater distance from the occluder bar 2180 of the cover member 2172. This distance may be sufficient to allow the fluid conduit in the outlet portion of the installed reservoir assembly to be substantially unrestricted such that fluid may be dispensed from the reservoir assembly.

Referring now also to FIGS. 79-87, a number of views of an example reservoir assembly 1600 in a disposable housing assembly 1602 are depicted. The reservoir assembly 1600 is substantially "E" like in shape with an outlet portion 1640 of the reservoir assembly 1600 forming the middle projection of the "E" similarly as described in relation to FIGS. 72-73. A sliding occluder 1670 is included in the example embodiment to prevent undesired flow through the outlet portion 1640.

As shown, the disposable housing assembly 1602 may include a trough structure 1604 against which the outlet portion 1640 of the reservoir assembly 1600 may rest when installed in the disposable housing assembly 1602. The walls 1606 of the trough structure 1604 may help to guide the reservoir assembly 1600 into the proper orientation when it is installed in the disposable housing assembly 1602. As shown, each of the walls 1606 may include a track 1608. The track 1608 may include a substantially straight section 1610 including a serif 1612 at one end. The occluder 1670 may include projections 1672 which may extend into the tracks 1608. The tracks 1608 may act as guides which direct displacement of the occluder 1670 as the occluder 1670 is slide from an occluding state to a flow permitting state.

Figure 79:
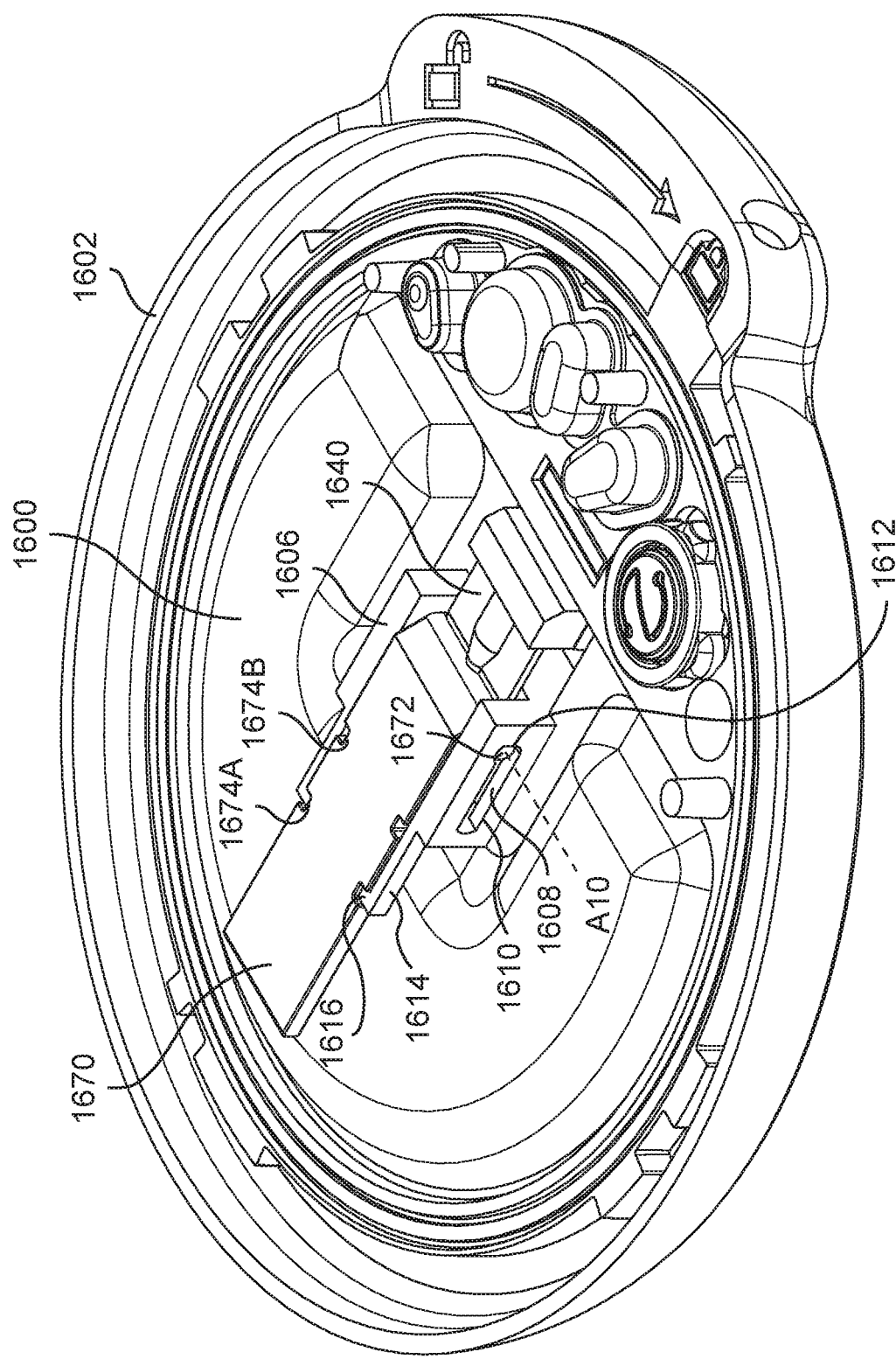
FIG. 79 is a perspective view of one embodiment of a disposable housing assembly, reservoir assembly, and slide type occluder.

Referring now also to FIGS. 79-81, the occluder 1670 is shown in an occluding state. When in the occluding state 1670, the projections 1672 of the occluder 1670 may be positioned at least partially in the serifs 1612 of the tracks. The occluder blade 1676 may press the fluid conduit 1642 of the outlet portion 1640 closed to inhibit passage of fluid through the outlet portion 1640. In the example embodiment, the occluder blade 1676 includes a rounded contact face 1678 at an end of the occluder 1670.

The trough 1604 of the disposable housing assembly 1602 is ramped in the example embodiment. As a result, the distance between the track 1608 and the surface of the trough 1604 on which the outlet portion 1640 rests is shortest at the end of the track 1608 where the serif 1612 is located. This distance may be chosen so as to generate an interference which pushes the occluder 1670 projections 1672 into the serifs 1612 when the occluder 1670 is in the occluding state. When in the serifs 1612, the projections 1672 of the occluder 1670 may help to lock the occluder 1670 in place and prevent inadvertent disengagement of the occluder 1670.

At least one of the walls of 1606 of the trough 1604 may include an interlock arm 1614. In the example embodiment shown in FIGS. 79-87, both walls 1606 include an interlock arm. The interlock arm 1614 may include a mating feature which interlocks with a cooperating structure on the occluder 1670. When the mating feature and cooperating structure are engaged with one another, the occluder 1670 may be inhibited from inadvertent displacement. In the example embodiment, the interlock arms 1614 include a projection 1616 that may engage a notch 1674A, B in the occluder 1670. In other embodiments, a notch may be included in the interlock arm 1614 and a projection may be included on the occluder 1670. As shown, the occluder 1670 includes a number of sets of notches 1674A, B. This may allow the occluder 1670 to be locked in a number of positions. For example, the occluder 1670 may be locked in an occluding position and a flow permitting position depending on which notches 1674A, B the projections 1616 of the interlock arms 1614 are interacting with. In FIG. 79, the projections 1616 are engaged with notches 1674A to lock the occluder 1670 in the occluding state.

Figure 82:
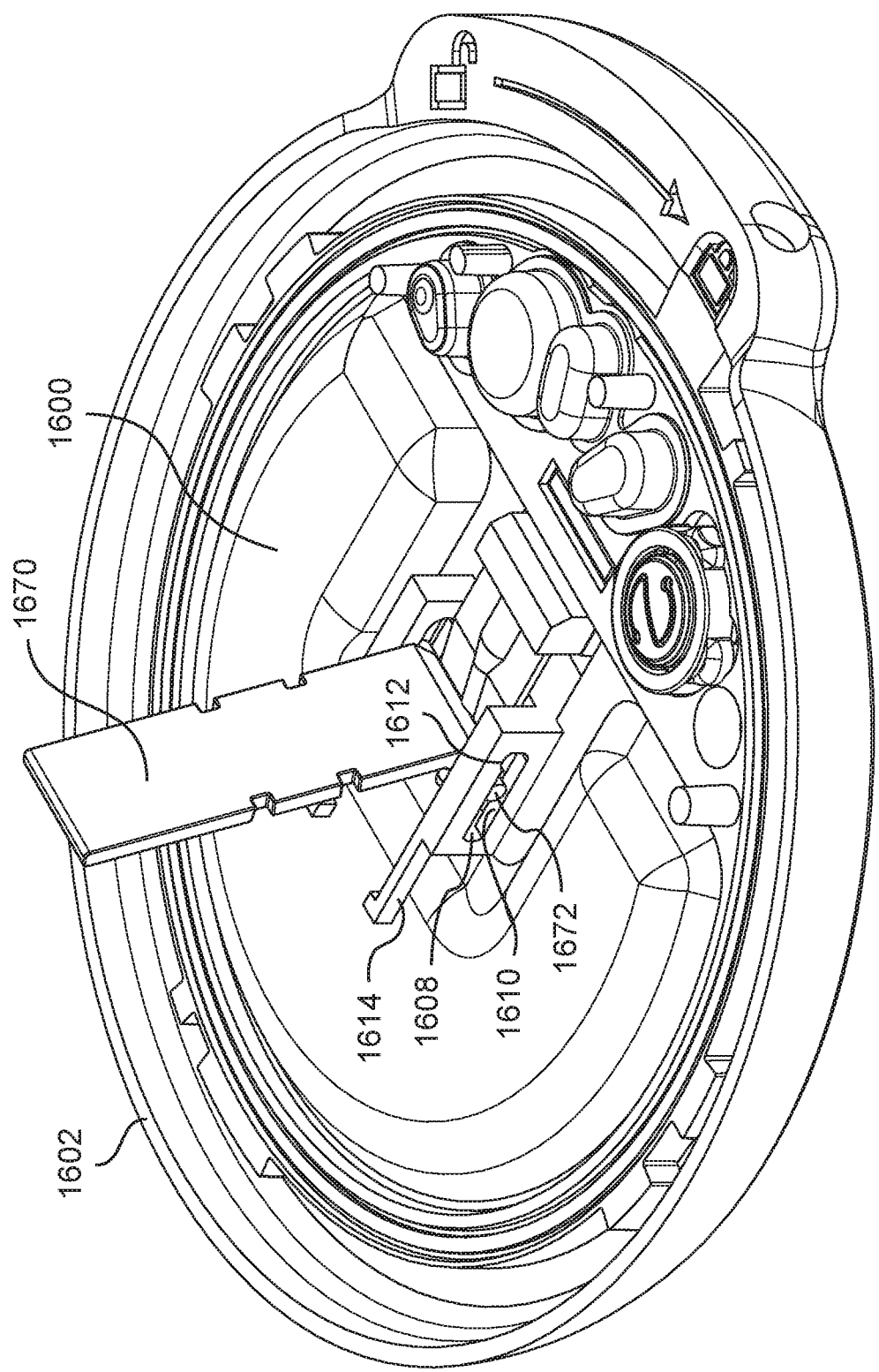
FIG. 82 is one embodiment of a disposable housing assembly, reservoir assembly, and slide type occluder of FIG. 79 with the occluder pivoted away from the disposable housing assembly and displaced away from an occluding position.

Referring now also to FIGS. 82-84, the occluder 1670 may be displaced manually or via an actuation mechanism from the occluding state to a flow permitting state. In various embodiments, the occluder 1670 may be pivoted about a pivot axis A10. In the example embodiment, the pivot axis A10 is the axis along which the projections of the occluder 1670 extend. When pivoted about the pivot axis A10 away from the disposable housing assembly 1602, the interlock arms 1614 may disengage the notches 1674A, B of the occluder 1670. The projections 1672 of the occluder 1670 may then be free to slide along the length of the tracks 1608. The occluder 1670 is shown displaced to an intermediary portion of the track 1608 in FIGS. 81-82. Where a serif 1612 is included in each of the tracks 1608 a downward force may be applied to bring the projections 1672 of the occluder 1670 out of the serif 1612 and even with the straight segment 1610 of the track 1608.

Depending on the embodiment, the contact face 1678 of the occluder blade 1676 may contoured such that the occluder blade 1676 may press against the outlet portion 1640 and close the fluid conduit 1642 when the occluder has been pivoted about axis A10 away from the disposable housing assembly 1602. This may be desirable as it may allow the occluder 1670 to also act as a hatch similar to hatch 1374 of FIG. 66. The occluder 1670 may pivoted about axis A10 to allow access to a fill extension (not shown, see 1262 of FIGS. 60-66 for example) of the reservoir assembly 1600. As the occluder 1670 may still occlude the outlet portion 1640 when in a pivoted position, the reservoir assembly 1600 may be filled with the occluder 1670 in the pivoted position.

Figure 85:
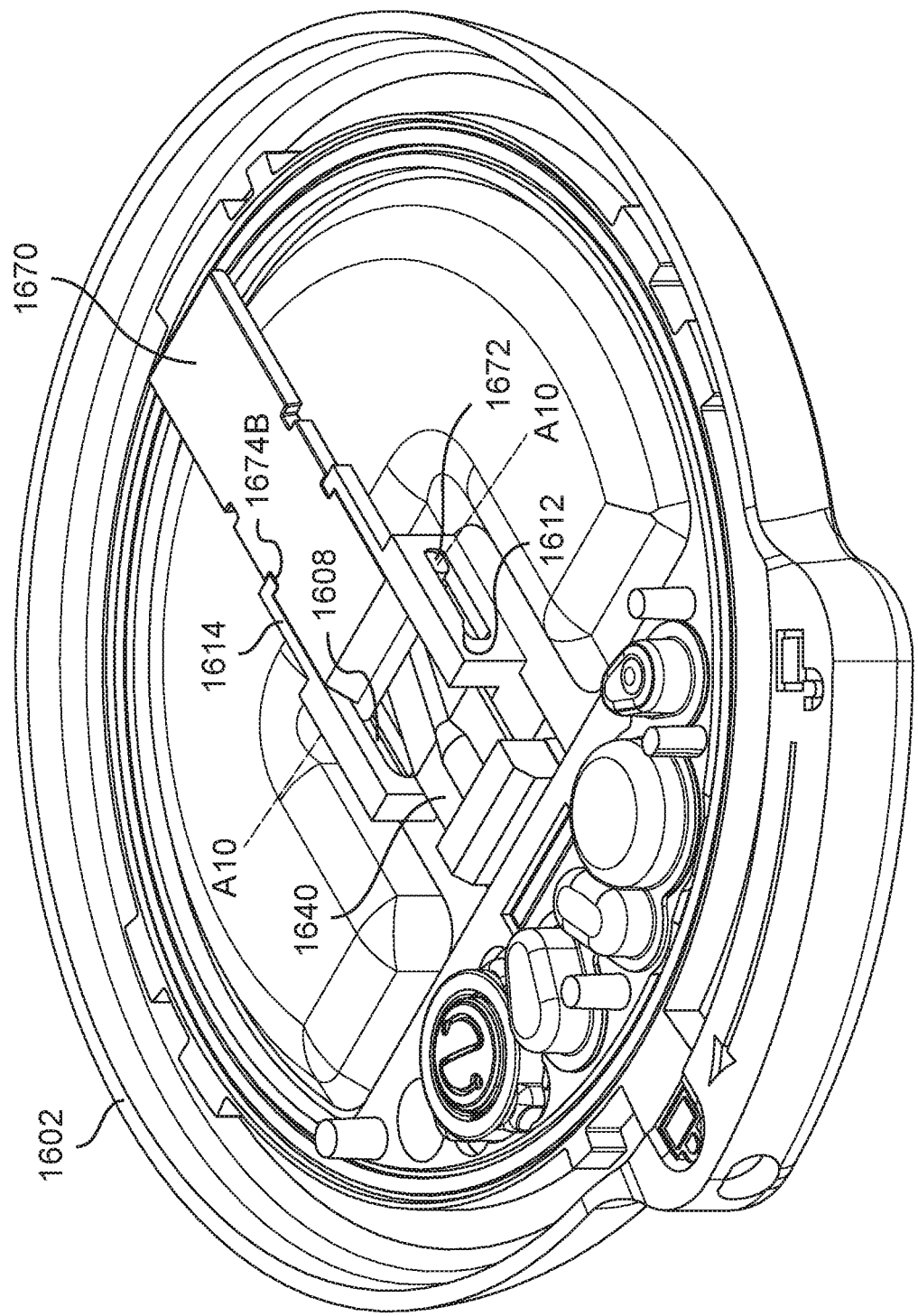
FIG. 85 is a perspective view of an embodiment of a disposable housing assembly, reservoir assembly, and slide type occluder of FIG. 79 where the slide occluder has been displaced to a flow permitting state.

Referring now also to FIGS. 85-87, once the projections 1672 of the occluder 1670 have reached the end of the track 1608 opposite the serifs 1612, the occluder 1670 may be in a flow permitting state. The occluder 1670 may be rotated about the pivot axis A10 back toward the disposable housing assembly 1602. The interlock arms 1614 of the disposable housing assembly may engage notches 1672B of the occluder 1670 to lock the occluder 1670 in the open, flow permitting state. The occluder blade 1676 may be out of or at least in minimal contact with the outlet portion 1640 and flow through the flow conduit 1642 may be substantially unimpeded.

Figure 90:
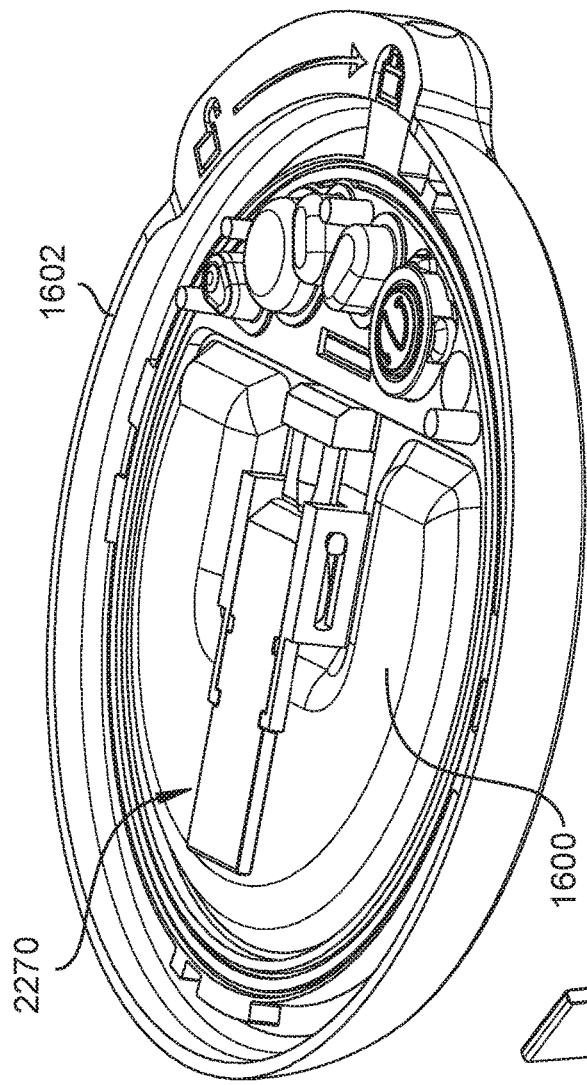
FIG. 90 is a perspective view of one embodiment of a disposable housing assembly of FIG. 88 with one embodiment of the cover removed, one embodiment of a reservoir assembly installed, and one embodiment of an occluder in an occluding state.
Figure 91:
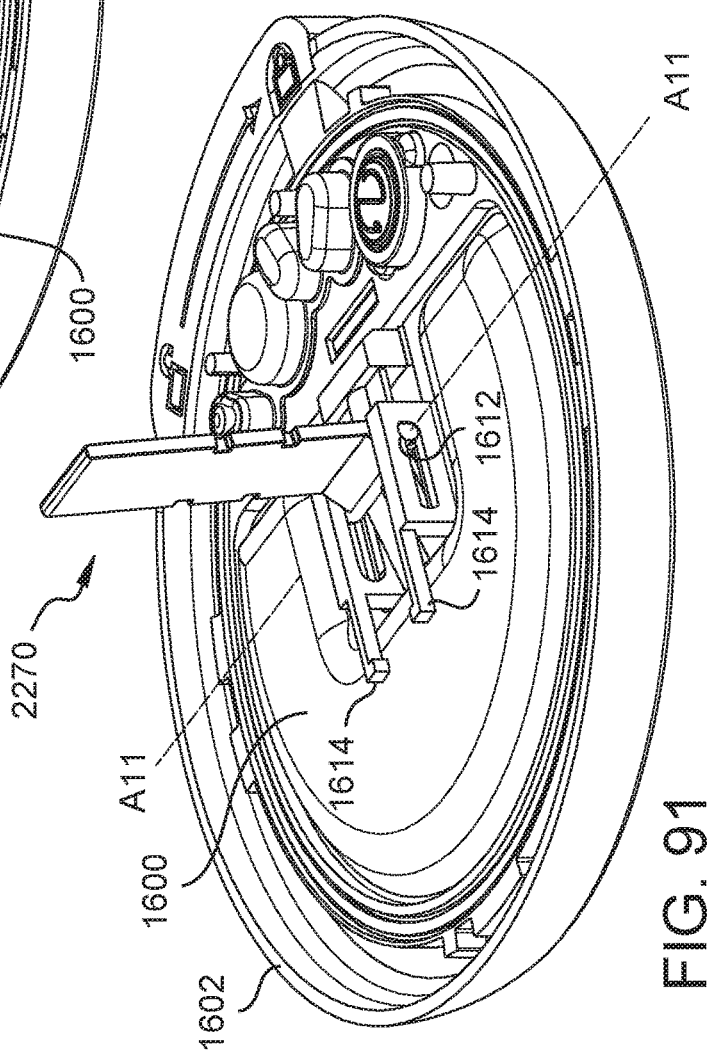
FIG. 91 is a perspective view of one embodiment of the disposable housing assembly of FIG. 88 with the cover removed, one embodiment of a reservoir assembly installed, and the occluder in a pivoted occluding state.

Referring now also to FIGS. 88-91, the example embodiment of FIGS. 79-87 is shown with an alternative occluder 2270. The example occluder 2270 is shown exploded out of the disposable housing assembly 1602 in FIG. 88. As best shown in FIG. 89, the projections 2272 of the occluder 2270 which ride along the track 1608 have an elongate shape with a width dimension greater than its height dimension. As shown in FIG. 90, when the projections 2272 are positioned in the end of the track 1608 including the serif 1612, the occluder 2270 may be rotated away from the disposable housing assembly 1602. When pivoted about pivot axis A11 away from the disposable housing assembly 1602, the elongate projection 2272 may rotate up into the serif 1612 as shown in FIG. 91. This may help to hold the occluder 2270 in the pivoted position and prevent inadvertent displacement from that position. In the pivoted position, the occluder 2270 may be in an occluding state and the reservoir assembly 1600 may be filled. Once filled, the occluder 2270 may be pivoted back toward the disposable housing assembly.

To actuate the occluder 2270 out of the occluding state, the occluder 2270 may be displaced to a second position in which its projections 2272 are pushed to the end of the track 1608 opposite the serif 1612. Due to the elongate shape of the projections 2272, the occluder 2270 may be inhibited from being pivoted about its pivot axis A11 during this actuation. Thus, the displacement of the occluder 2270 during actuation to the flow permitting state may be substantially constrained to a displacement within a plane. This may help to limit the ability to access the space under the cover member 1681 where the reservoir assembly 1600 is located. During displacement, the interlock arm 1614 may deflect away from the occluder 2270 such that they are out engagement with notches 2274A. As shown best in FIG. 88, the cover member 1681 includes a cutout 1683 into which the arms may deflect. Once the occluder 2270 has been displaced to the second position, the interlock arms 1614 may spring back inward toward the occluder 2270 to engage notches 2274B. This engagement may help to prevent inadvertent displacement of the occluder 2270.

Figure 92:
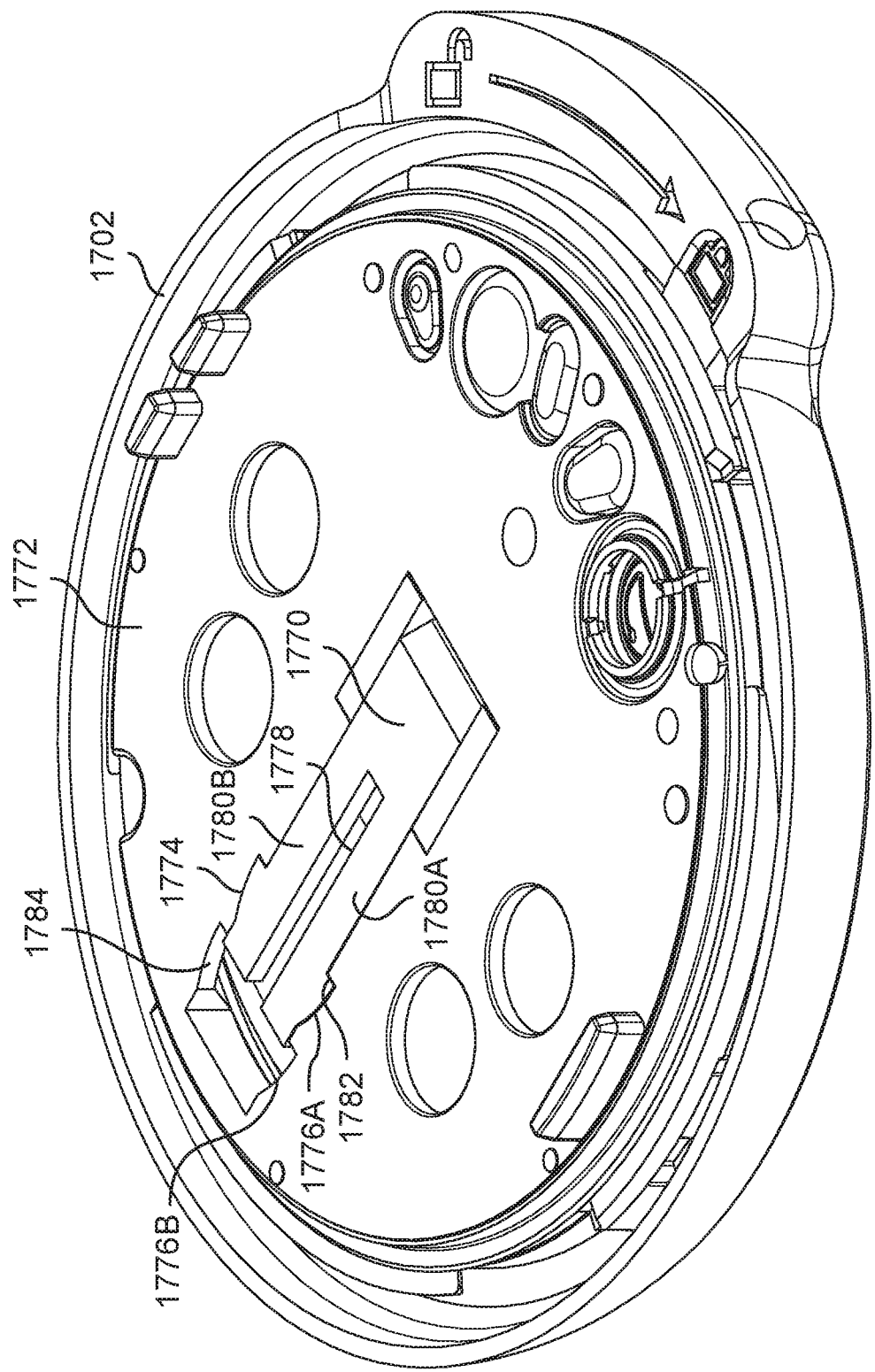
FIG. 92 is a perspective view of one embodiment of a disposable housing assembly with one embodiment of a slide occluder.
Figure 93:
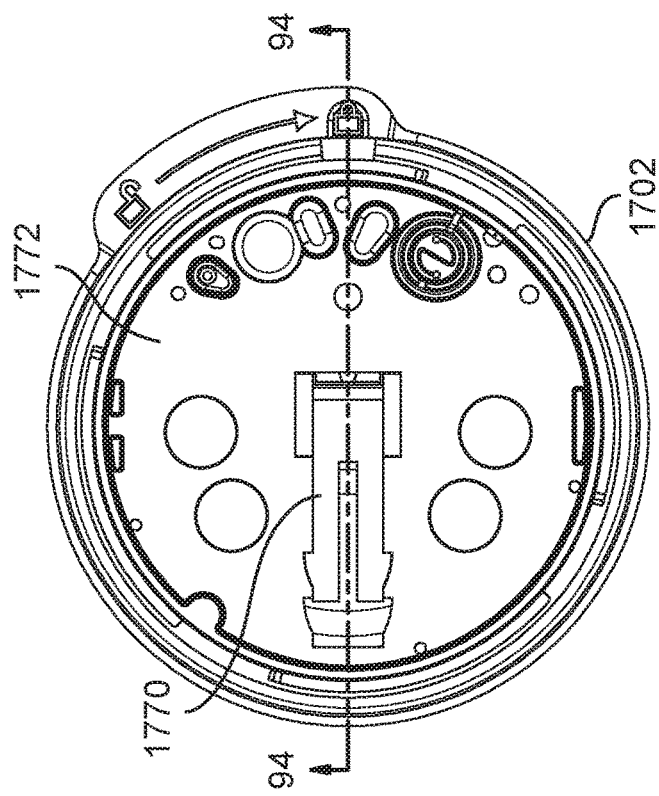
FIG. 93 is a top down view of one embodiment of a disposable housing assembly and slide occluder of FIG. 93.
Figure 94:
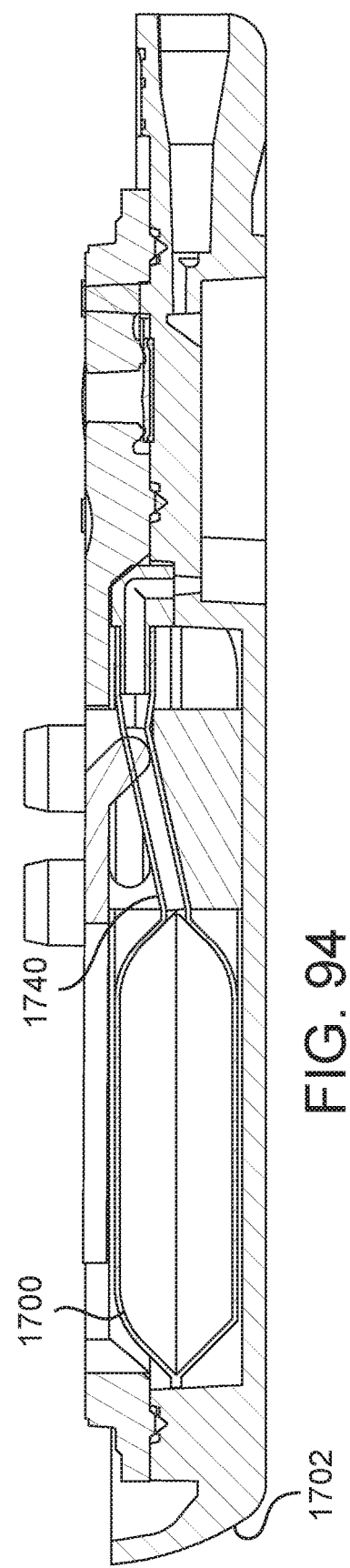
FIG. 94 is a cross sectional view taken at line 94-94 of FIG. 93.

In certain embodiments, and referring now primarily to FIGS. 92-94, interlock arms may not be included. Instead, a cover member 1772 of the disposable housing assembly 1702 may include an interlock cutout 1784. The interlock cutout 1784 may be sized to accept at least one projection 1774 included in the occluder 1770. The example occluder 1770 includes two projections 1774. The example interlock cutout 1784 includes a plurality of tiers 1176A, B each of which being able to accept the projections 1774 of the occluder 1770. When the projections 1774 are disposed within a tier 1776A, B of the interlock cutout 1774, the occluder 1770 may be locked in place. As best shown in FIG. 94, the occluder 1770 is shown locked into its occluding state inhibiting flow through the outlet section 1740 of the reservoir assembly 1700.

Still referring to FIGS. 92-94, the projections 1774 may be barb type projections. Each of the projections 1774 may be disposed on a respective deflection arm 1780A, B. The deflection arms 1780A, B are separated by a slit 1778 extending through the occluder 1770 intermediate the projections 1774. The width of the slit 1778 may be chosen to allow for a desired degree of deflection of the deflection arms 1780A, B. As the example occluder 1770 is displaced in the plane of the cover member 1772 toward tier 1776B, the ramped shape of the interlock cutout 1774 at tier 1776A may force the deflection arms 1780A, B to deflect inward toward one another. In turn, this may cause the distance between the projections 1774 to become smaller. Once the end of the projections 1774 pass into tier 1776B, the deflection arms 1780A, B may spring back into a non-deflected, resting orientation. The step or lip 1782 of the projection may then catch against the edge of the second tier 1776B of the interlock cutout 1774. Consequentially, the occluder 1770 may be ratcheted into the flow permitting configuration and prevented from inadvertently returning to the occluding state. Though the exemplary occluder 1770 may be restricted to displacement in the plane of the cover member 1772, other embodiments may be capable of pivoting as described in relation to FIGS. 79-87.

Figure 95:
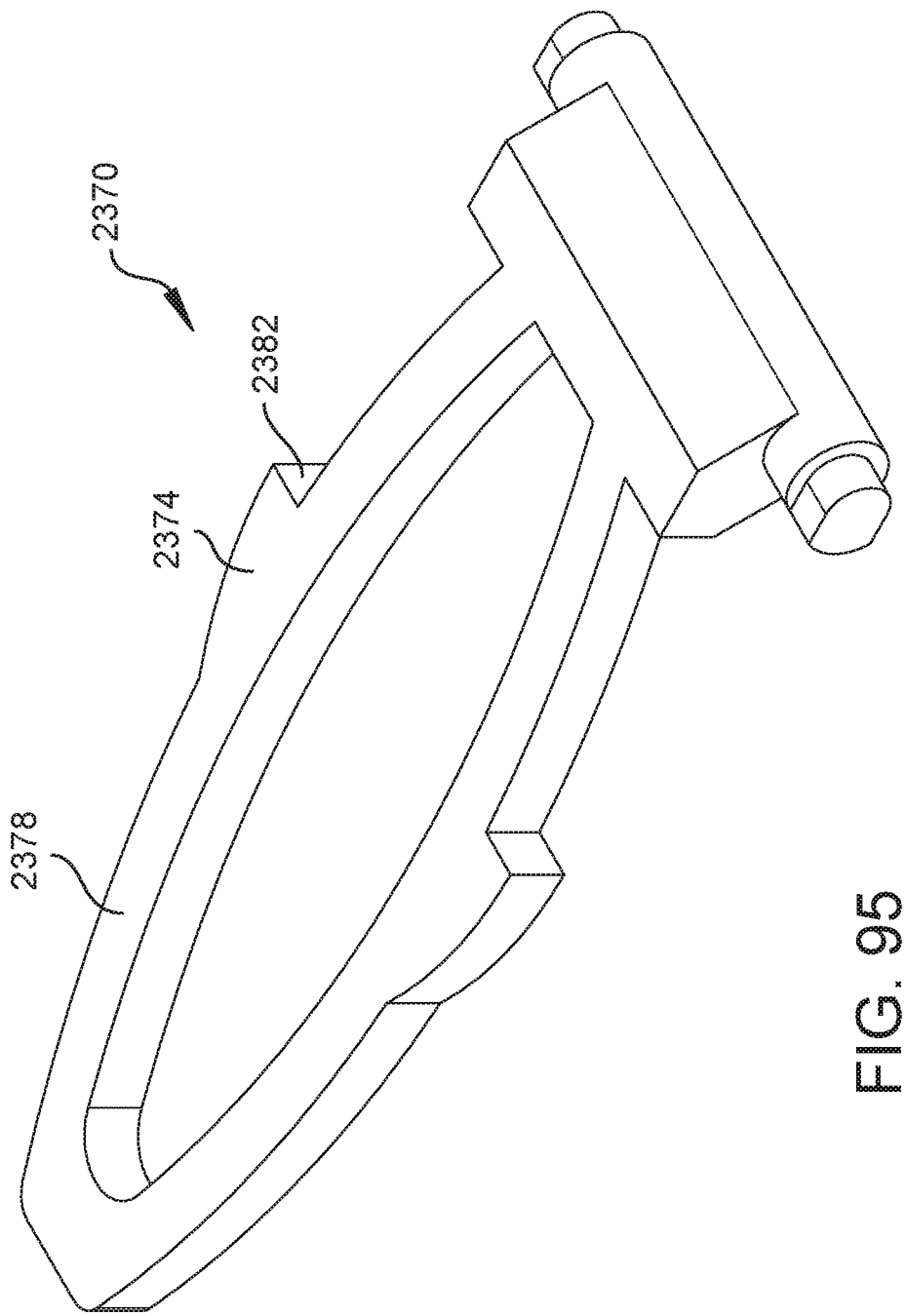
FIG. 95 is a perspective view of one embodiment of a slide occluder.

Referring now also to FIG. 95 and alternative occluder 2370 including a hoop 2378 type structure instead of a slit is depicted. Such an occluder 2370 may be used with a disposable housing assembly 1702 similar to that in FIGS. 92-94. For instance, as the example occluder 2370 is displaced in the plane of the cover member 1772 toward tier 1776B, the ramped shape of the interlock cutout 1774 at tier 1776A may compress the hoop shape 2378. In turn, this may cause the distance between the projections 2374 on the hoop shape 2378 to become smaller. Once the end of the projections 2374 pass into tier 1776B, the hoop shape 2378 may spring back into a non-compressed, resting conformation. The step or lip 2382 of the projection 2374 may then catch against the edge of the second tier 1776B of the interlock cutout 1774. Consequentially, the occluder 2370 may be ratcheted into the flow permitting configuration and prevented from inadvertently returning to the occluding state.

Figure 96:
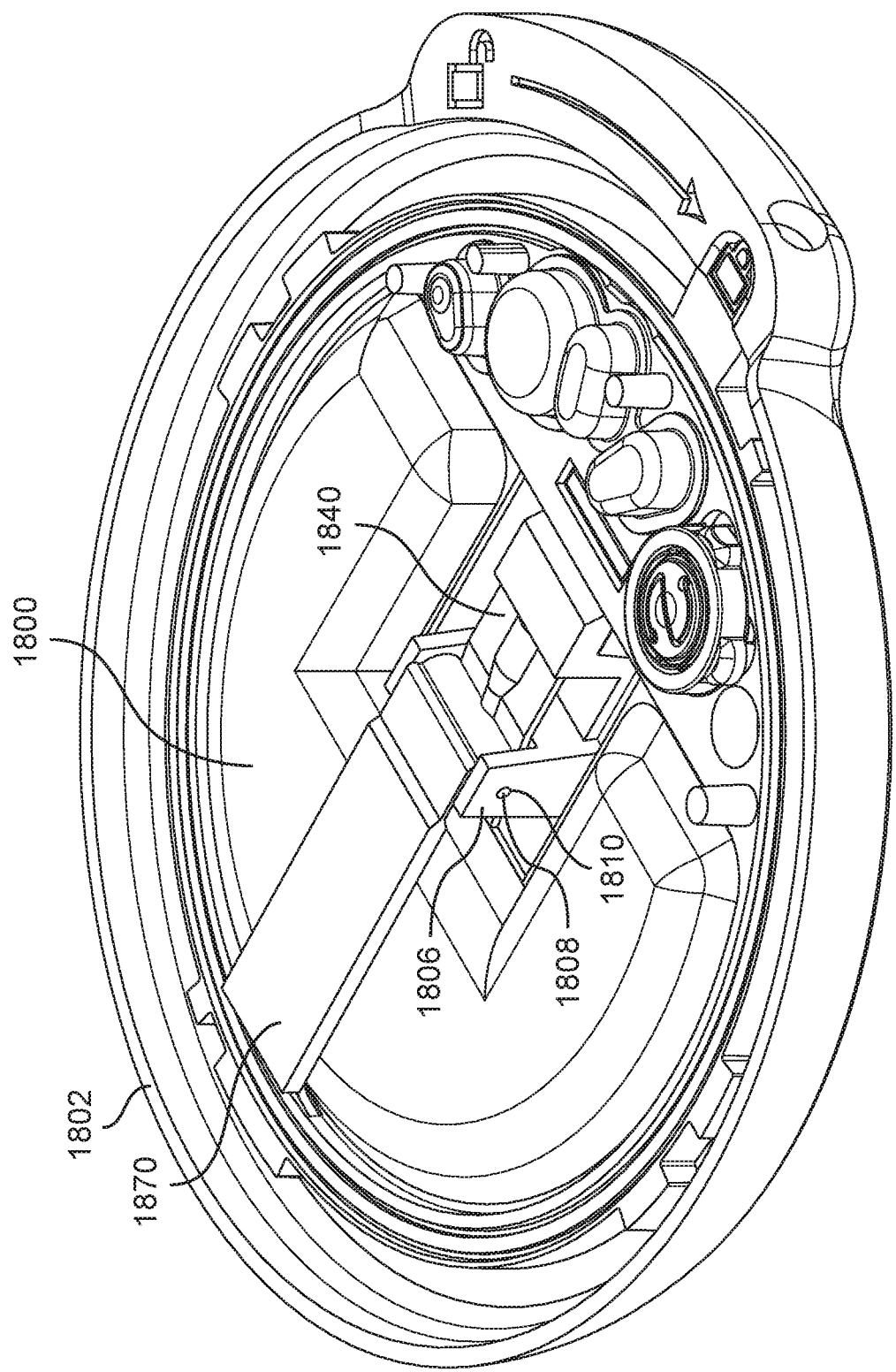
FIG. 96 is a perspective view of one embodiment of a disposable housing assembly, reservoir assembly, and cam type occluder.
Figure 97:
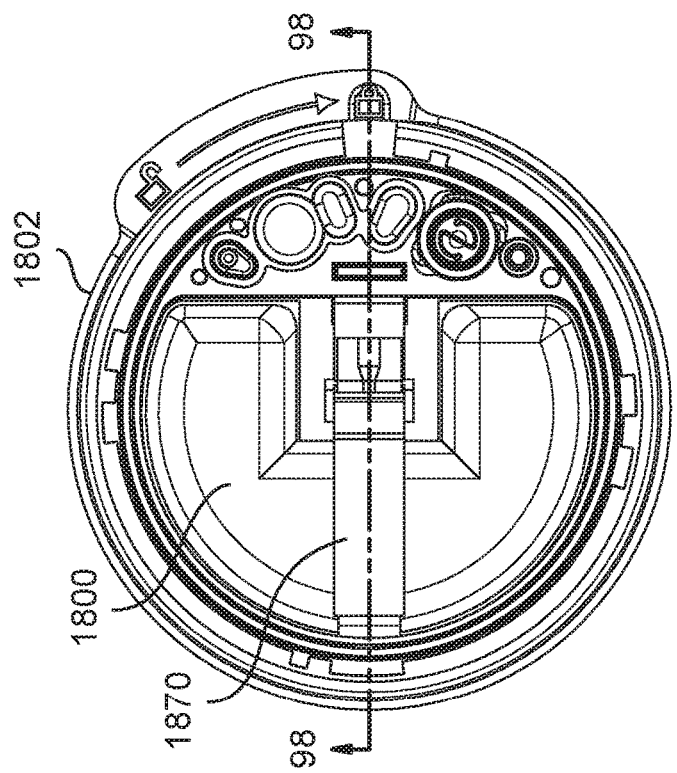
FIG. 97 is a top down view of one embodiment of a disposable housing assembly, reservoir assembly, and cam type occluder of FIG. 96.
Figure 98:
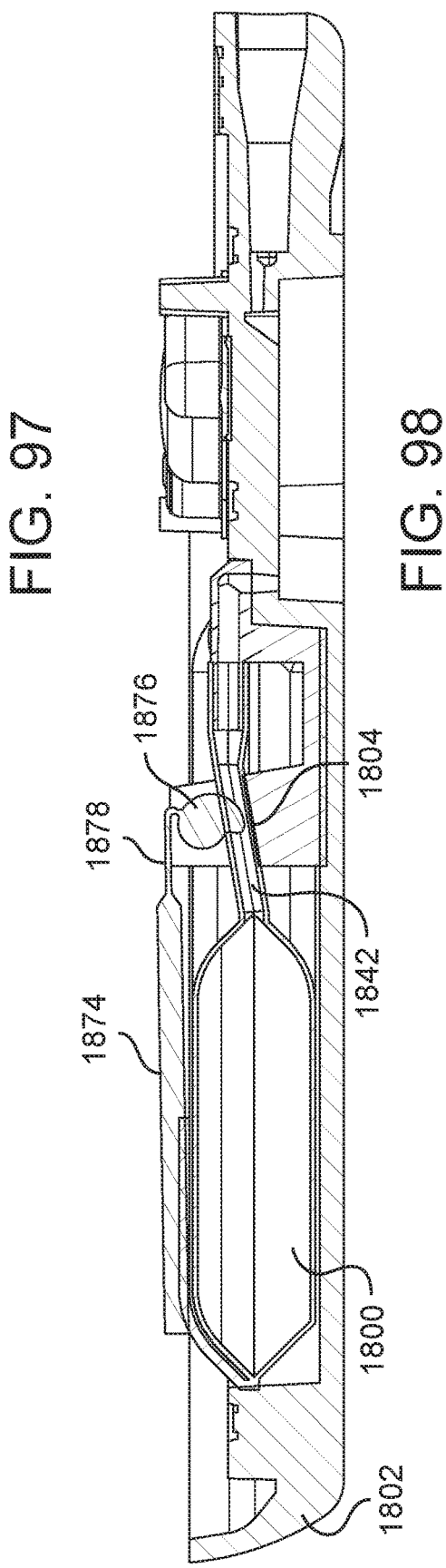
FIG. 98 is a cross section taken at line 98-98 of FIG. 97.

Referring now also to FIGS. 96-98, a number of views of another example reservoir assembly 1800 in a disposable housing assembly 1802 are depicted. The reservoir assembly 1800 is substantially "E" like in shape with an outlet portion 1840 of the reservoir assembly 1800 forming the middle projection of the "E" similarly as described in relation to FIGS. 72-73. A sliding occluder 1870 is included in the example embodiment to prevent undesired flow through the outlet portion 1840.

In the example embodiment shown in FIGS. 96-98, the occluder 1870 includes a main body portion 1874, a cam 1876 and an intermediary portion 1878 coupling the main body portion 1874 and the cam 1876. The disposable housing assembly 1802 may include a trough 1804 upon which the outlet portion 1840 of the reservoir assembly 1800 may rest when the reservoir assembly 1800 is installed in the disposable housing assembly 1802. The walls 1806 of the trough 1804 may include respective bearing mounts 1810 for pivot pins 1808 of the cam 1876.

As best shown in FIG. 98, the intermediary portion 1878 may be relatively thin and able to flex. The intermediary portion 1878 may be about 20-40% the thickness of the main body portion 1874. In the exemplary embodiment, the intermediary portion 1878 is about one third the thickness of the main body portion 1874. The cam 1876 is shown in an occluding position where flow through the fluid conduit 1842 of the outlet portion 1840 is inhibited. To transition the occluder 1870 from this occluding state to a flow permitting state, the main body portion 1874 of the occluder 1870 may be displaced (manually or via actuator) away from the outlet portion 1840. This may rotate the cam 1876 such that the section of the fluid conduit 1842 following the cam 1876 may no longer be pressed against the trough 1804. With the cam rotated out of the way, fluid flow through the fluid conduit 1842 of the outlet portion 1840 may be established. The cam 1876 of the example embodiment, is depicted as a snail type cam. Any other type of cam may be used in alternative embodiments. For example, an eccentric cam, elliptical cam, pear shaped cam, or geometrically shaped cam may be used.

Figure 99:
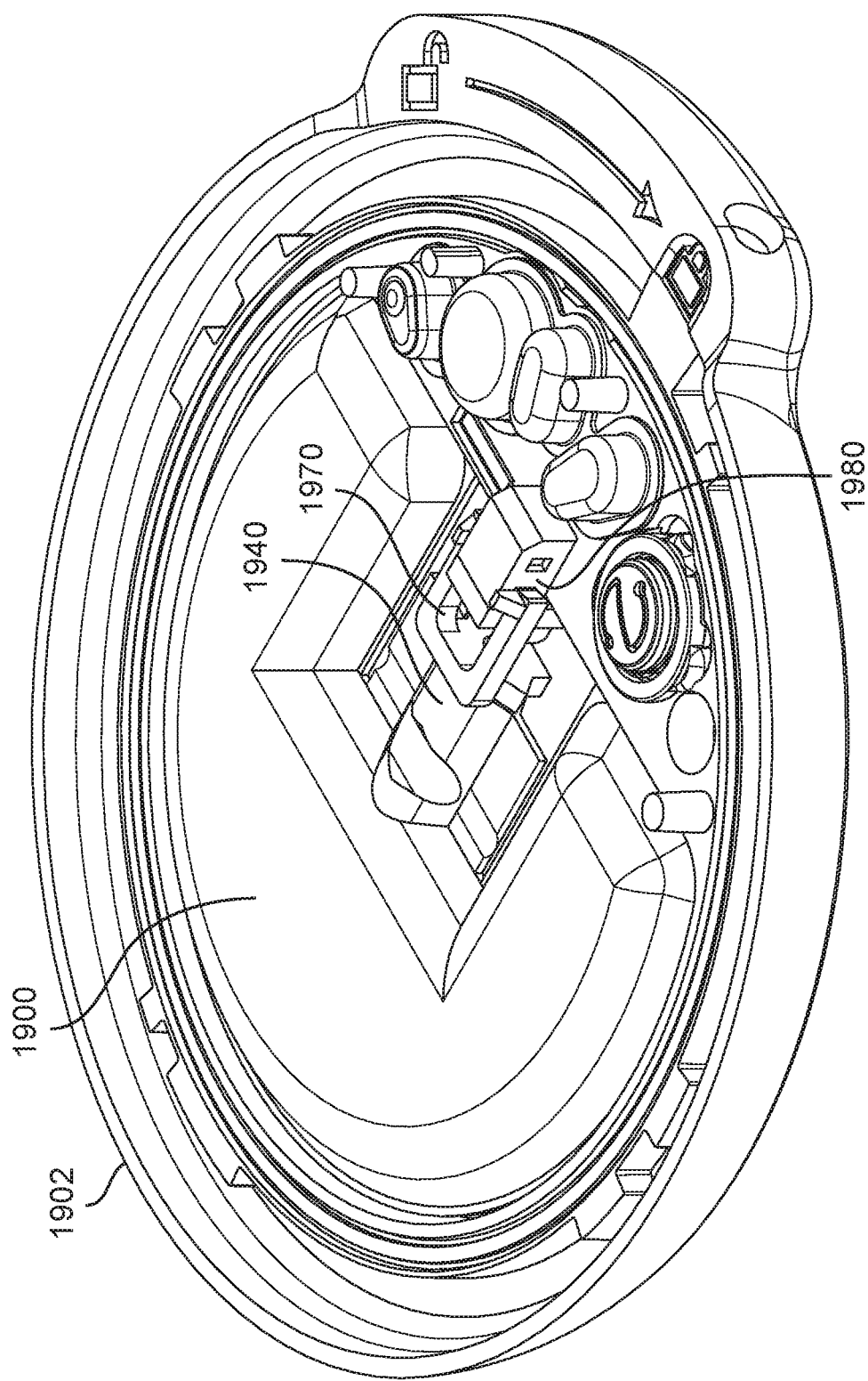
FIG. 99 is a perspective view of one embodiment of a disposable housing assembly and reservoir assembly having a sled coupled to its outlet portion.
Figure 100:
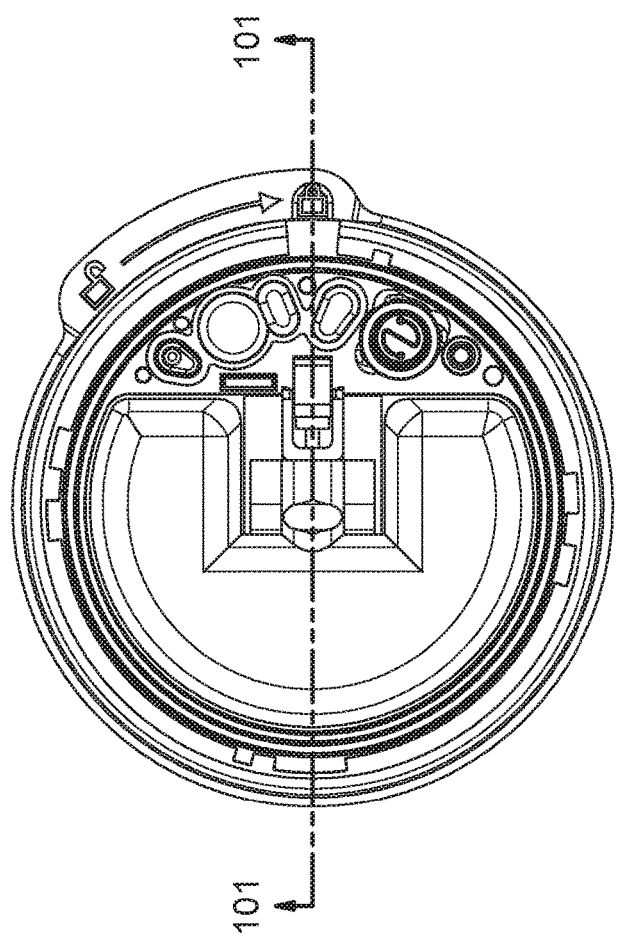
FIG. 100 is a top down view of one embodiment of a disposable housing assembly and reservoir assembly of FIG. 99.
Figure 101:
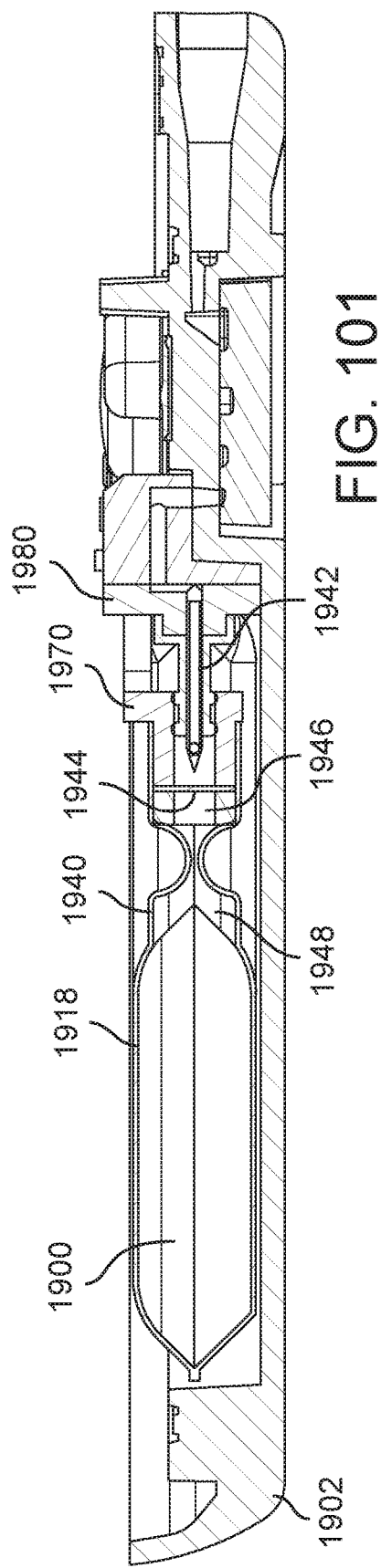
FIG. 101 is a cross sectional view taken at line 101-101 of FIG. 100.
Figure 102:
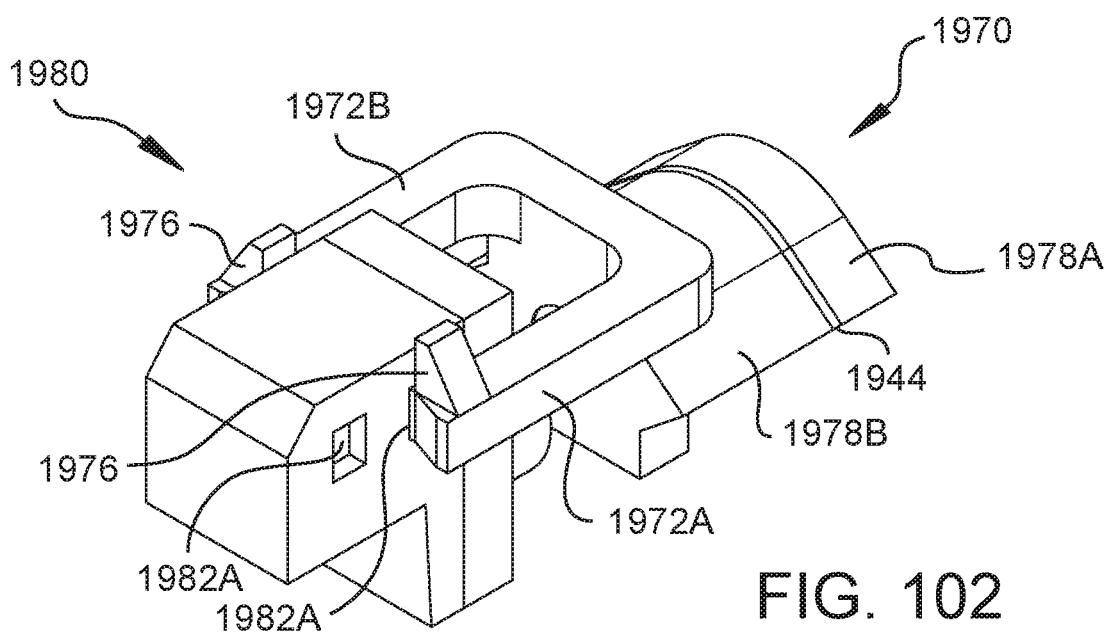
FIG. 102 is a perspective view of one embodiment of a sled and connector body in a first separated state.
Figure 103:
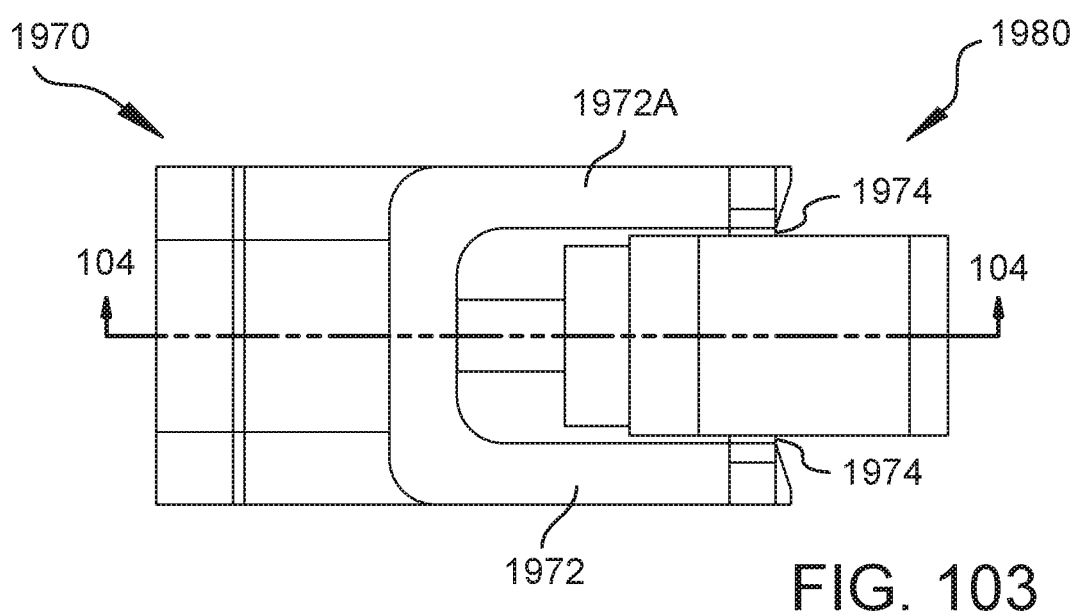
FIG. 103 is a top down view of one embodiment of a sled and the connector body of FIG. 102 in the first separated state.
Figure 104:
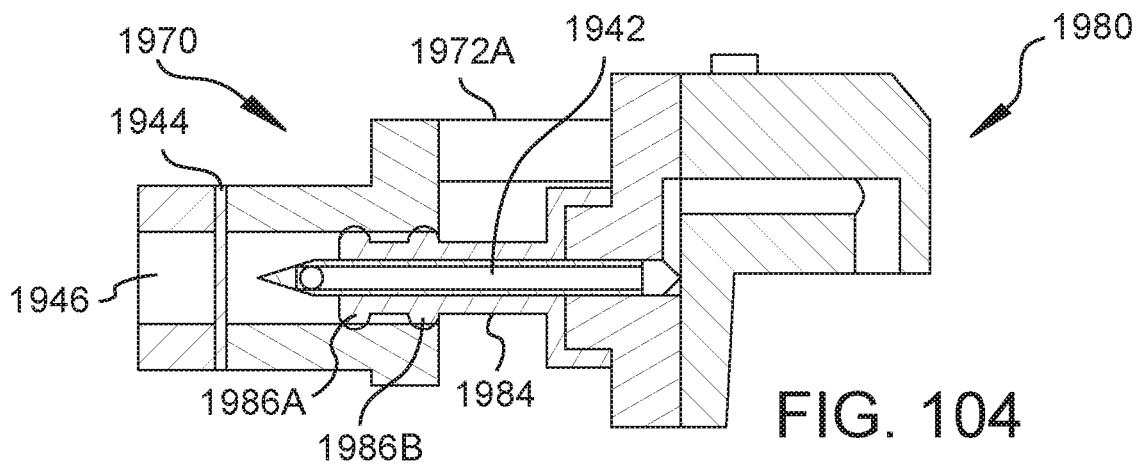
FIG. 104 is a cross section taken at line 104-104 of FIG. 103.
Figure 105:
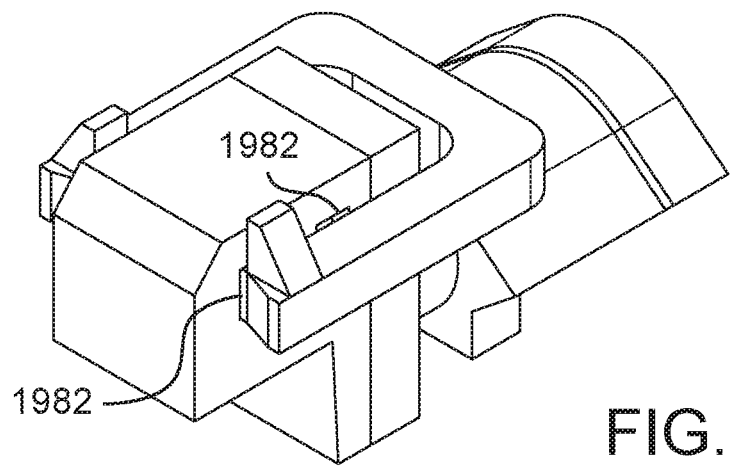
FIG. 105 is a perspective view of one embodiment of a sled and connector body of FIG. 102 in a second state in which a septum of the sled has been pierced by a piercing member of the connector body.
Figure 106:
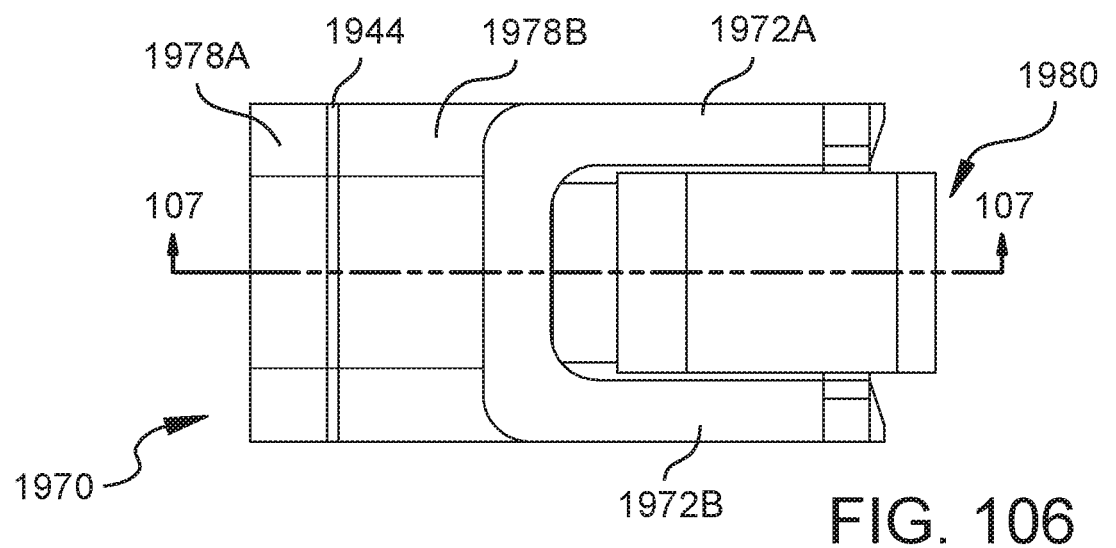
FIG. 106 is a top down view of one embodiment of a sled and connector body of FIG. 102 in the second state.

Referring now also to FIG. 99-101, a number of views of another example reservoir assembly 1900 in a disposable housing assembly 1902 are depicted. The reservoir assembly 1900 is substantially "E" like in shape with an outlet portion 1940 of the reservoir assembly 1900 forming the middle projection of the "E" similarly as described in relation to FIGS. 72-73. An occluder is not included in the example embodiment shown in FIGS. 99-101. Instead, the flow conduit 1948 of the outlet portion 1940 of the reservoir assembly 1900 is sealed with a septum 1944 as best shown in the cross-section in FIG. 101.

The outlet portion 1940 in the example embodiment is attached to a sled 1970. The sled 1970 may be displaced from a first position (shown in FIGS. 99-101) to a second position in which the septum 1944 has been pierced by a needle 1942 included in a connector body 1980 of the disposable housing assembly 1902. Once pierced, a flow pathway between the interior volume of the reservoir assembly 1900 and various fluid channels and circuitry of the disposable housing assembly 1902 may be established. In the first position, the outlet portion 1940 may be folded over on itself, accordioned, bunched up, or otherwise compacted into a slack state. Thus, when the sled 1970 is in the first position, the outlet portion 1940 includes sufficient slack to allow the sled 1970 and the attached segment of the outlet portion 1940 to displace to the second position. This second position may be referred to as an extended position.

Referring now also to FIGS. 102-107 a number of views of the sled and connector body 1980 are shown. The sled 1970 is shown in the first position in FIGS. 102-104 and in the second position in FIGS. 105-107. The sled 1970 may include two arms 1972A, B having projections 1974. The projections 1974 may engage with mating recesses 1982A, B included in the connector body 1980. Once engaged, the projections 1974 may hold the sled 1970 in position and prevent inadvertent displacement. The sled 1970 arms 1972A, B may also include a protuberance 1976. The protuberances 1976 may serve as a push surface for manual displacement of the sled 1970 via a user's thumb or other digit(s). The protuberances 1976 may also serve as an engagement element for an actuation mechanism depending on the embodiment.

The sled 1970 may be constructed from a plurality of pieces in some embodiments. In the example embodiment depicted in FIGS. 102-107, the sled includes a first portion 1978A, a second portion 1978B, and the septum 1944. The arms 1972A, B may be coupled to the second portion 1978B. Referring now also to FIG. 101, the reservoir 1918 material from which the outlet portion 1940 of the reservoir assembly 1900 is constructed may be bonded to an exterior surface of the first portion 1978A and at least a part of the second portion 1978B of the sled 1970. The first and second portions 1978A, B may have an airfoil like cross section in the area where the reservoir 1918 material is bonded to the sled 1970. This may help to allow the reservoir material 1918 to easily be bonded around the sled 1970 without bunching or being required to make a sharp bend. A fluid channel 1946 may extend through the first and second portions 1978A, B and be partitioned into two separate segments by the septum 1944. In the example embodiment, the septum 1944 is sandwiched between the first portion 1978A and second portion 1978B. One of the sections may be in direct fluid communication with the flow conduit 1948 of the outlet portion 1940. In certain embodiments, the septum 1944 may be constructed of the same material as the reservoir 1918. If this material is constructed of a number of different materials, the layer most compatible with the fluid stored within the reservoir assembly 1900 may be oriented facing the first portion 1978A of the sled 1970.

Still referring to FIGS. 102-107, the needle 1942 may be fitted with one or more gasket member 1984. In the example embodiment, the needle 1942 is surrounded by a compliant material including two sealing ribs 1986A, B. The sealing ribs 1986A, B may be compressed against the interior wall of the fluid conduit 1946 in the sled 1970 forming redundant, fluid tight seals. As shown, the needle 1942 includes an orifice 1945 which extends through a side wall of the needle 1942. In other embodiments, the orifice 1945 may be in line with the long axis of the needle 1942.

Figure 107:
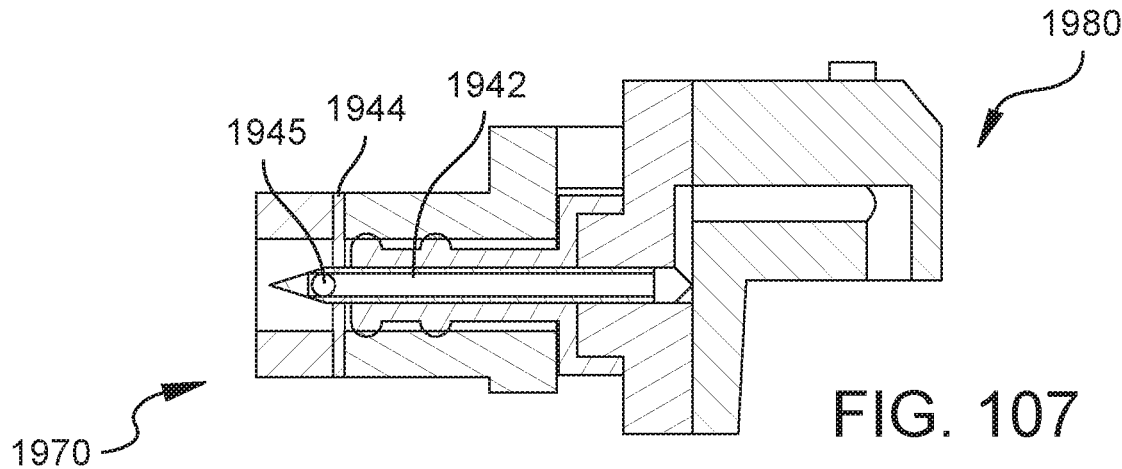
FIG. 107 is a cross section taken at line 107-107 of FIG. 106.

Referring now also to FIG. 107, the needle 1942 length may be chosen such that at its greatest extent, the needle 1942 projects into the fluid channel 1946 a distance less than the full length of the fluid channel 1946. Thus, when the sled 1970 has been advanced to the second position, the first portion 1978A of the sled 1970 may prevent the tip of the needle 1942 from contacting the reservoir 1918. In this manner, a sled 1970 may also act as a needle guard. In the example embodiment, when the sled 1970 is in the second position, the needle 1942 may project along about 95-97% of the length of the fluid channel 1946.

Figure 108:
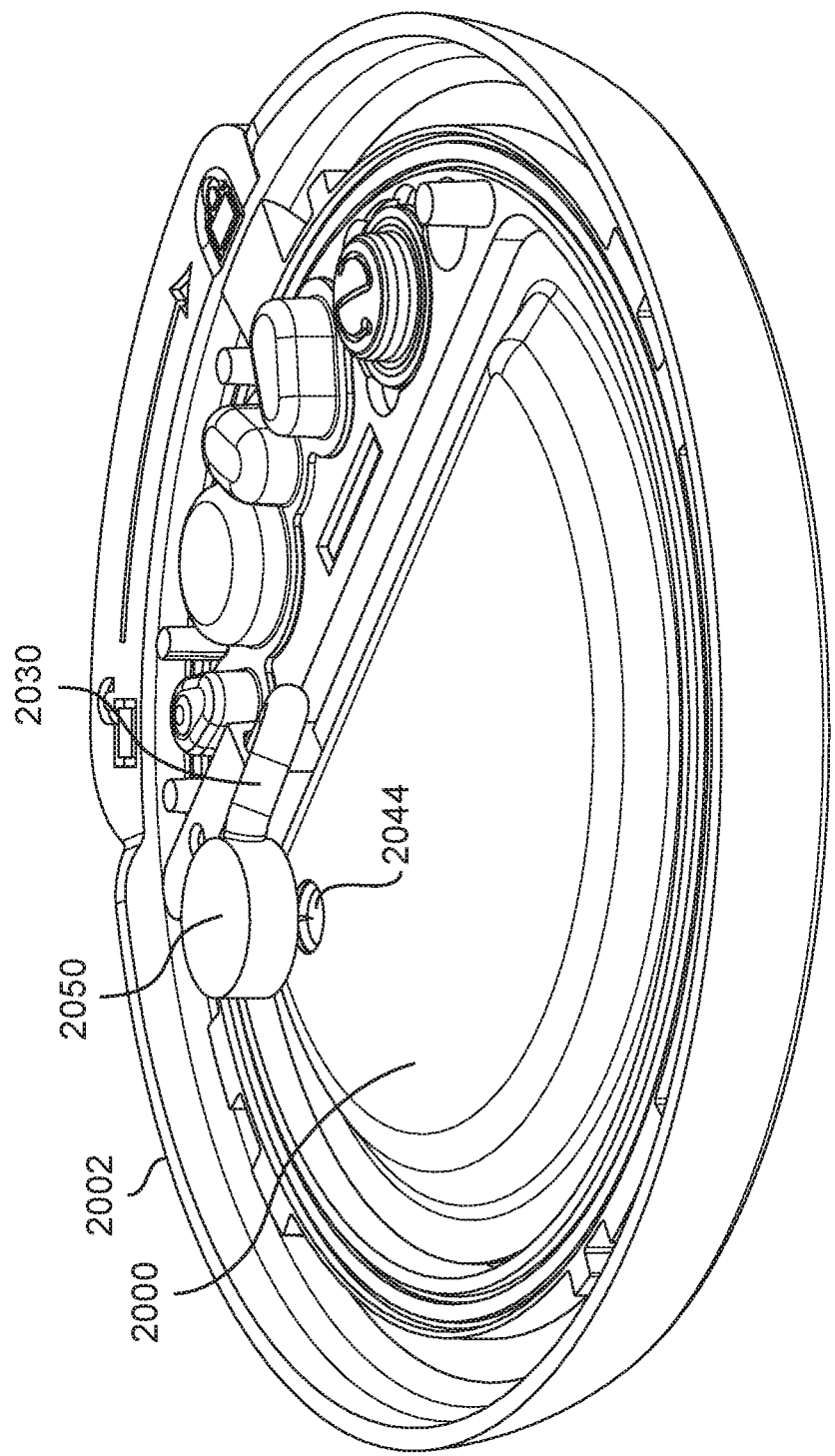
FIG. 108 is a perspective view of one embodiment of a disposable housing assembly including a reservoir having a port assembly with a septum.

Referring now also to FIGS. 108-110 a number of views of another exemplary embodiment of reservoir assembly 2000 in a disposable housing assembly 2002 are depicted. As shown, the reservoir assembly 2000 is substantially "D" like in shape. No outlet portion is included in the reservoir assembly 2000. Additionally, an occluder is not included in the example embodiment shown in FIGS. 108-110. Instead, the reservoir assembly 2000 includes an access port assembly 2040 as best shown in FIG. 110. The access port assembly 2040 includes a septum 2044. The septum 2044 may be made of a self sealing material such as a butyl elastomer or other elastomeric material. In certain embodiments, the reservoir assembly 2000 may be filled with a fill extension 1262 as described in FIGS. 60-65. In other embodiments, filling of the reservoir assembly 2000 may be accomplished via the septum 2044.

The example embodiment includes a tack assembly 2050 which is coupled to the disposable housing assembly 2002 via tubing 2030. The tubing 2030 may couple to a connector body 2080 on the disposable housing assembly 2002 which places the lumen of the tubing 2030 into fluid communication with the various fluid channels and circuitry included in the disposable housing assembly 2002. The connector body 2080 may include an introduction port 2082 for glue, adhesive, or the like to affix the tubing 2030 into the connector body 2080. The tack assembly 2050 may include a needle 2052 and a body 2054. The body 2054 may include a flow pathway 2056 which places the lumen of the needle 2052 into communication with the lumen of the tubing 2030. Though not shown in FIGS. 108-110, a removable guard which surrounds the needle 2052 may be included. A contact surface 2058 of the body 2054 may include an adhesive to help anchor the tack assembly 2050 onto the reservoir assembly 2000 during use.

Figure 111:
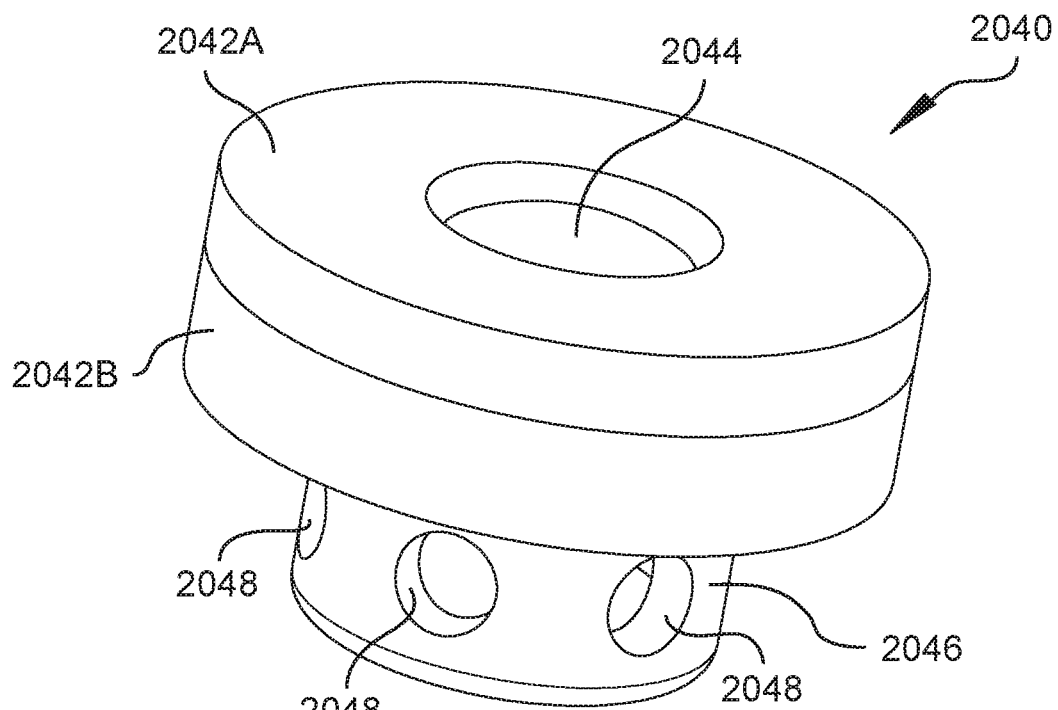
FIG. 111 is a perspective view of one embodiment of a port assembly.
Figure 112:
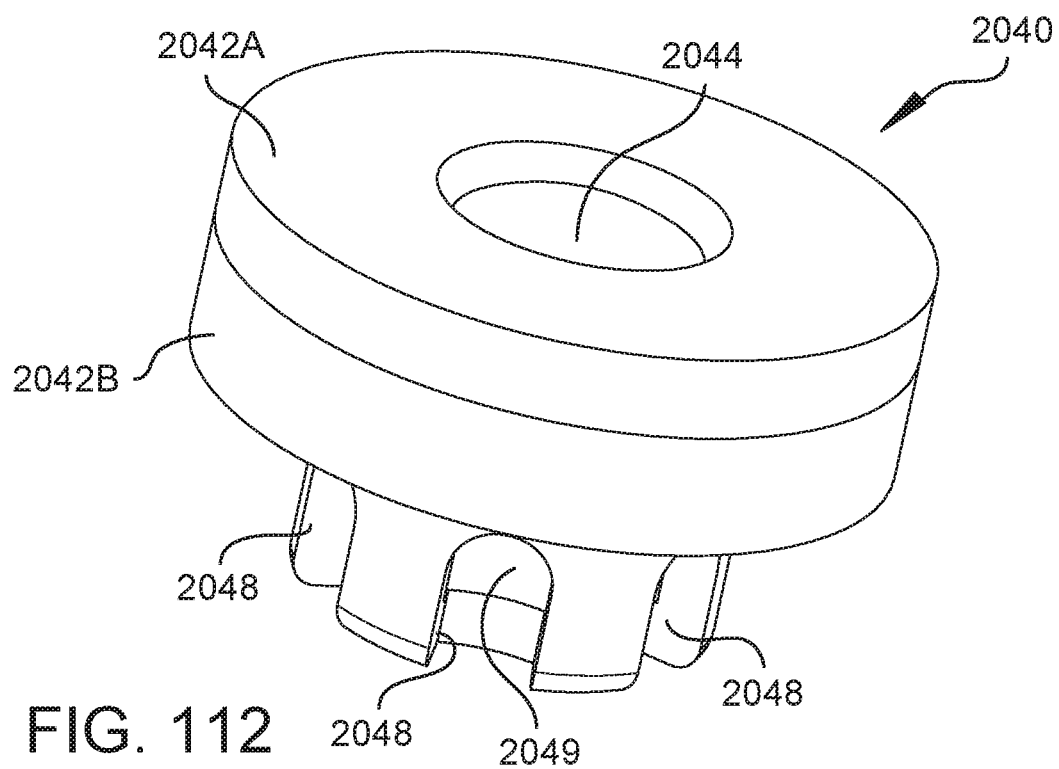
FIG. 112 is a perspective view of one embodiment of a port assembly.

Referring now also to FIG. 111 and FIG. 112 two example access port assemblies 2040 are shown. Each of the access port assemblies 2040 includes a septum 2044. The septum 2044 may be captured between a first portion 2042A and second portion 2042B of the access port assembly 2040. The first portion 2042A and second portion 2042B of the access port assembly may capture the septum 2044 between one another when first portion 2042A and second portion 2042A are coupled to one another. The first portion 2042A and second portion 2042B may be coupled together in any suitable manner including ultrasonic welding, heat bonding, laser welding, snap fit, interference fit, etc.

As shown, the second portion 2042B of an access port assembly may include a well 2046. The well 2046 may act as a guard and ensure that the reservoir 2018 material is prevented from contacting the needle 2052. The walls of the well 2046 may include one or more fenestrations 2048. The fenestrations 2048 may be any suitable shape. In FIGS. 110 and 111, the fenestrations 2048 are round opening that are substantially circular. In FIG. 112, the fenestrations 2048 are arch type orifices in the side walls of the well 2046. The arch type fenestrations 2048 extend all the way down to a bottom plate 2049 of the well 2046. This may help to mitigate potential for fluid to be isolated out of communication with the interior of the well 2046 as the volume contained in the reservoir assembly 2000 is depleted. In alternative embodiments, the well 2046 may not include a wall with fenestrations 2048. Instead the well 2046 may be defined at least partially by a resilient mesh or screen material. The mesh material may not deform as the reservoir 2018 collapses and/or may be resistant to puncture by the needle 2052.

Referring now also to FIGS. 113-116, a number of views of another exemplary reservoir assembly 2400 are depicted. The reservoir assembly 2400 includes an outlet portion 2440 which includes a piercing member 2442. As best shown in FIG. 116, a cross section taken along the axis of the piercing member 2442, the piercing member 2442 may extend into the outlet portion 2440 and include an interior lumen 2444. The interior lumen 2444 may be in communication with a flow pathway in the outlet portion 2440 via at least one port 2446 in the piercing member 2442. The piercing member 2442 may, in some embodiments, be made of a plastic material to facilitate bonding of the reservoir 2418 material to the piercing member 2442 (e.g. via heat bonding).

The reservoir assembly 2400 is in FIGS. 113-116 also includes an occluder 2470. The occluder 2470 may include a rod member 2472. An end face of the rod member 2472 may include a recess 2476 which may be sized to accept the outlet portion 2440 of the reservoir assembly 2400. Once the outlet portion 2440 has been positioned in the recess 2476, the rod member 2472 may be rotated about its longitudinal axis. This rotation may cause the outlet portion 2440 to kink closed and cutting off fluid communication between the interior volume of the reservoir assembly 2400 and the piercing member 2442. A fill extension 1262 (see, e.g. FIG. 60) may be included to allow for filling of the reservoir assembly 2400 while the occluder 2470 is in the rotated, occluding state. In alternative embodiments, filling of the reservoir assembly 2400 may be performed through the lumen of the piercing member 2442. When the occluder 2470 is not in place or is in a flow permitting rotational orientation.

The rod member 2472 may include a projecting member 2478 such as a tab or similar protuberance. This projecting member 2478 may engage a receiving recess in a disposable housing assembly to hold the occluder 2470 in the rotated, occluding position. The disposable housing assembly may also include a septum separating various flow channels and passages in the disposable housing assembly from the surrounding environment. When the reservoir assembly 2400 is installed in the disposable housing assembly, the piercing member 2442 may extend through the septum (not shown). The occluder 2470 may be rotated out of the occluding orientation to a flow permitting orientation where the outlet portion 2440 is not kinked. In some embodiments, the occluder 2470 may be completely removed to permit flow through the outlet portion 2440 to the lumen of the piercing member 2442.

Figure 117:
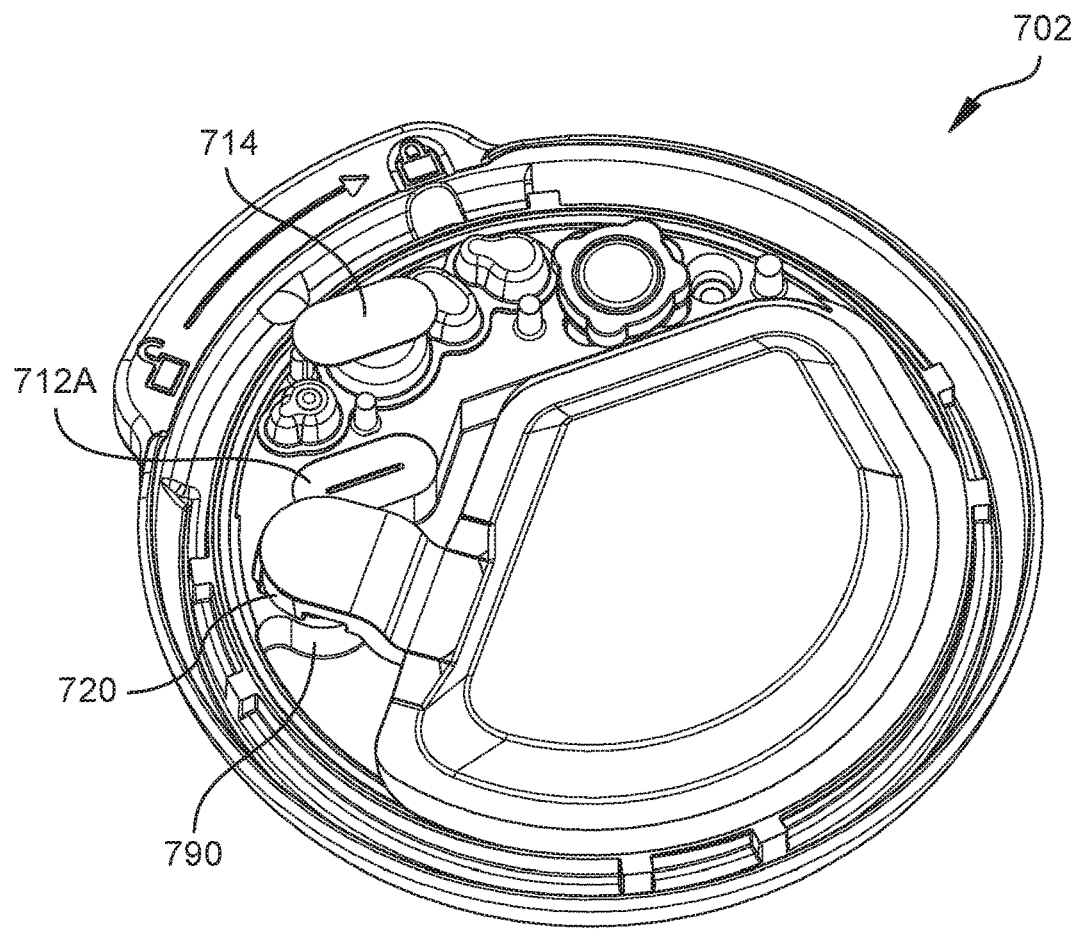
FIG. 117 is a perspective view of another example disposable hosing and example reservoir assembly with a cover plate exploded away from the body of the disposable housing assembly.
Figure 118:
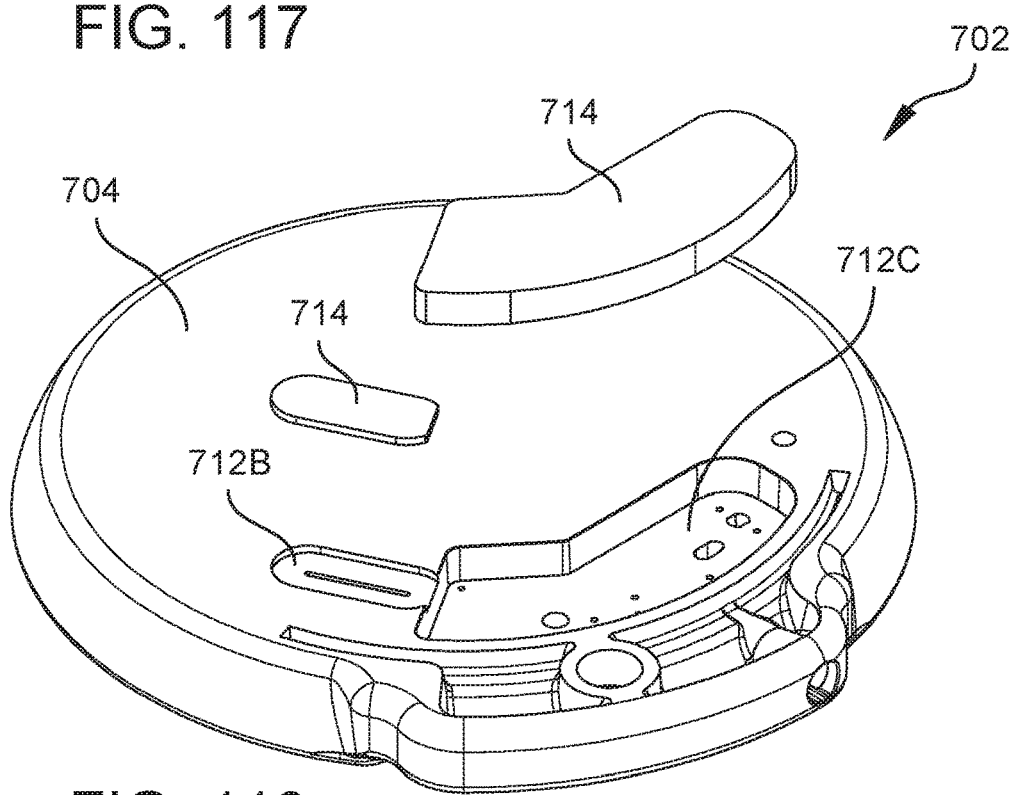

Referring now also to FIGS. 117-118, a disposable housing assembly 702 may include a number of recessed regions 712A-C which may be formed in the base portion 704 of the disposable housing assembly 702. The recessed regions 712A-C may each be sized to accept a cover plate 714. Each cover plate 714 may cooperate with its respective recessed region to defined one or more flow pathways. The cover plates 714 may be attached to the rest of the disposable housing assembly 702 in any suitable manner. In certain embodiments, the cover plates 714 may be laser welded to the base portion 704 after installation in the recessed regions 712A-C.

As shown, a base portion 704 of a disposable housing assembly 700 may include recessed regions 712A-C on both a first (e.g. bottom) face and second (e.g. top) face. Two recessed regions 712A-C may also be placed adjacent one another in a tiered relationship. For example recessed region 712B is adjacent recessed region 712C, but recessed to a shallower depth than recessed region 712C. The fluid pathway formed by recessed region 712A and its associated cover plate 714 facilitates transfer of fluid between the tiers on the opposing face of the base portion 704.

Such a tiered arrangement may allow for the placement of fluid pathways in a wide variety of locations in the base portion 704 while maximizing the amount of space available on an opposing side for other features of the disposable housing assembly 702. This may help to keep the overall size of the disposable housing assembly 702 small and easily carried or concealed on the body. As shown in the example embodiment, recessed region 712B is generally opposite a connector interface 790 for a port connector 720. Recessed region 712A is disposed generally opposite a portion of recessed region 712A and recessed region 712C.

Figure 119:
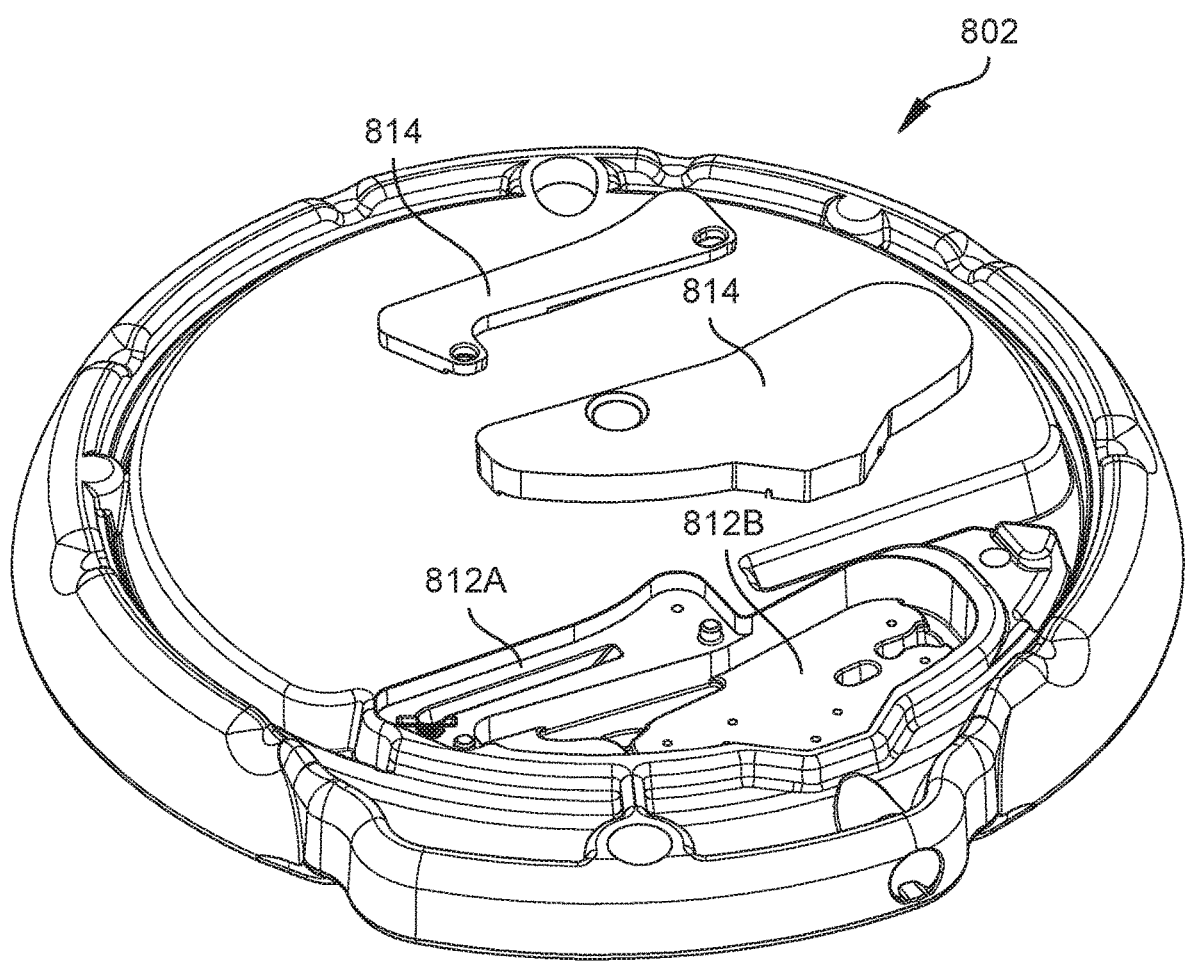

Referring now also to FIG. 119-122 a disposable housing assembly 802 that includes two recessed regions 812A, B is depicted. These recessed regions 812A, B are tiered with recessed region 812A being shallower in depth than recessed region 812B. Referring back to FIGS. 117-118, the recessed region 712A and its cover plate 714 act to provide a connector fluid path between fluid pathways in the tiers defined by recessed regions 712B-C and their associated cover plates 714. In FIG. 119, a variable depth flow path 830 is included to facilitate transition between tiers. Again, this may help to keep the disposable housing assembly 802 compact, allowing it to be easily carried or concealed by a user.

As best shown in FIG. 122, an enlarged view of an indicated portion of the cross section of FIG. 121 taken along the variable depth flow path 830, the variable depth flow path 830 may be partially included in the cover plate 814 and partially in the first recessed region 812A. A first region 831A of the variable depth flow path 830 is disposed opposite a connector interface 890 included in the disposable housing assembly 802. The first portion 831A of the variable depth flow path is recessed into the cover plate 714 associated with the recessed portion 812A. The recessed portion 812 is substantially flat such that when the cover plate 814 is sealed to the recessed region 812A, the recessed portion 812A forms a side wall of the variable depth flow path 830. This helps to maximize the amount of the thickness of the disposable housing assembly 802 which is available to define and support the connector interface 890.

The variable depth flow path 830 also includes a second region 831B in the example embodiment. The second region 831B acts as a transition region. A portion of the variable volume flow path 830 is recessed into the cover plate 814 as well as into the face of recessed portion 812A in the second region 831B. In this embodiment, a portion of the cross sectional area of the variable volume flow path 830 extends into both the cover plate 814 and the disposable housing assembly 802 throughout the second region 830. A third region 831C of the variable depth flow path 830 is also included in the example embodiment. The third portion 831C of the variable depth flow path 830 is recessed into the face of recessed region 812A. The adjacent face of the associated cover plate 814 is substantially flat such that when the cover plate 814 is sealed to the recessed region 812A, the cover plate 814 forms a side wall of the variable depth flow path 830. The third region 831C also includes an air trap 891. As shown, the air trap 891 includes a screen 895. The screen 895 is installed into a well 893 included in the third region 831C. The air trap 891 may operate similarly to as described in any one or more of the applications and/or patents incorporated herein by reference. The variable depth flow path 830 leads from the connector interface 890 to various valve stations 880 included in the disposable housing assembly 802. The valve stations 880 may be any of those described in any one or more of the applications and/or patents incorporated herein by reference.

Figure 123:
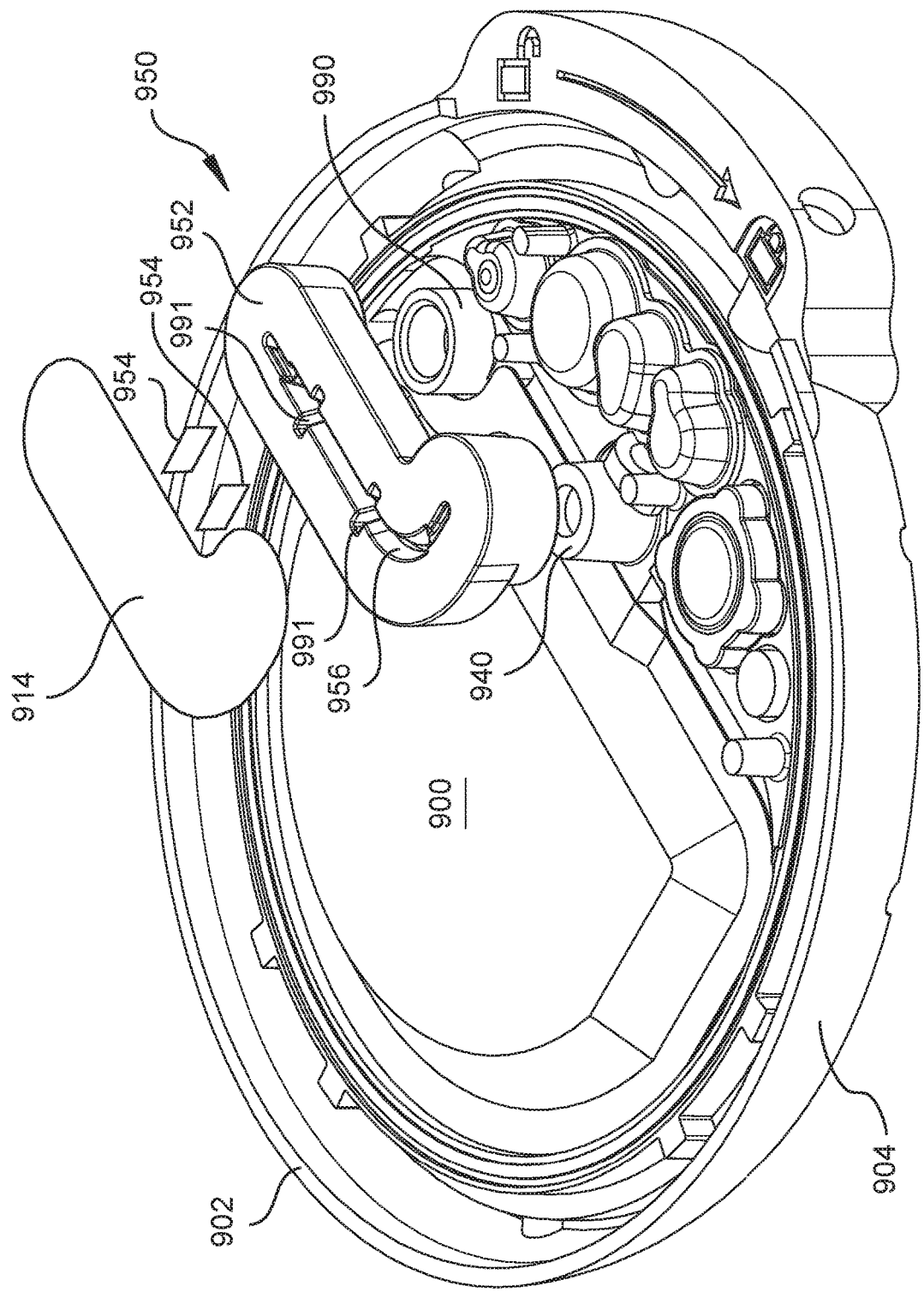
Figure 124:
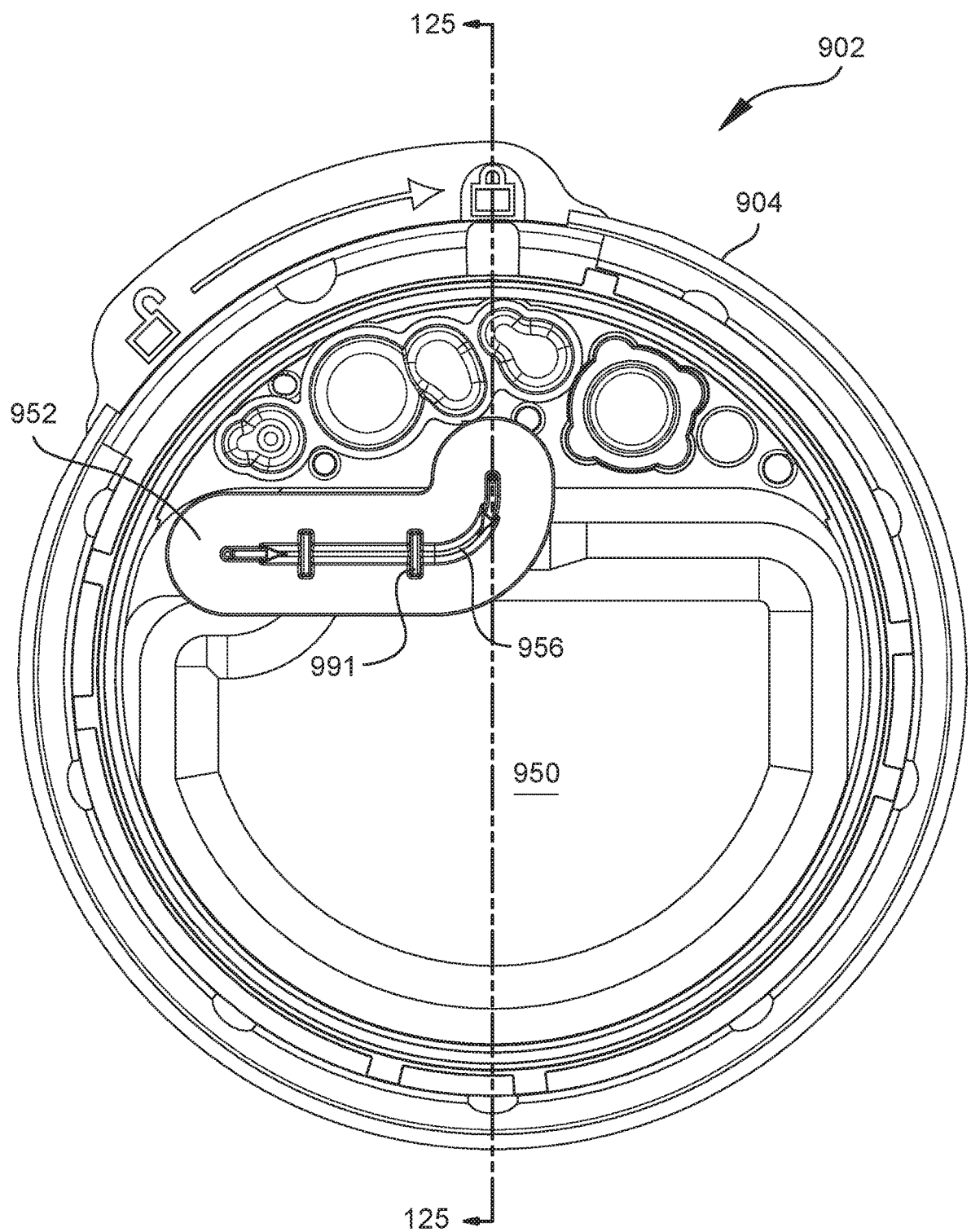
Figure 125:
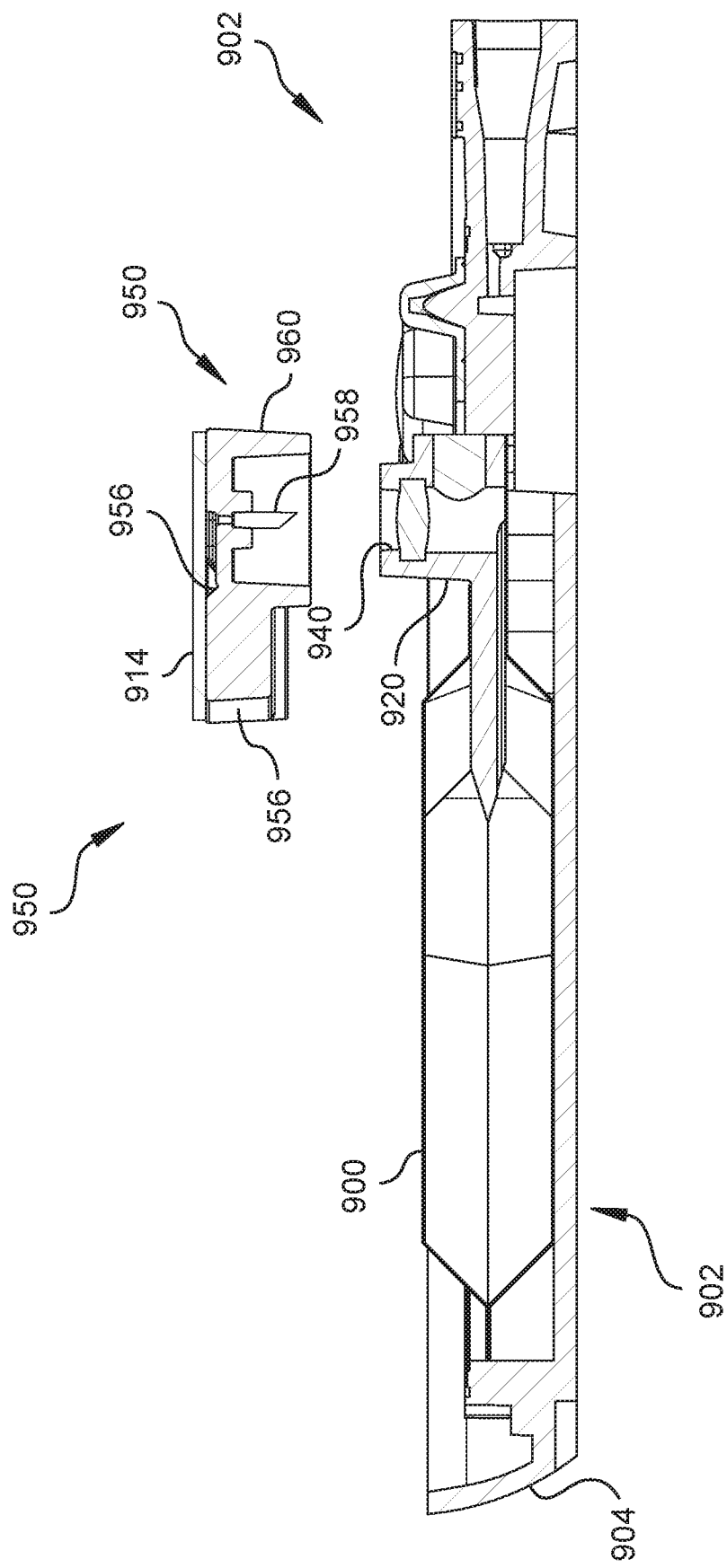

Referring now also to FIGS. 123-125, in some embodiments, a flow path may be provided in a self contained conduit sub-assembly 950 which is installed into a disposable housing assembly 902. Such a sub-assembly 950 may, once installed, establish fluid communication from a port of a reservoir assembly 900 to another port in the disposable housing assembly 902. In the shown example, the sub-assembly 950 establishes fluid communication from an outlet 940 of a reservoir assembly 900 to a first port 990 included in a connector of the base portion 904 of a disposable housing assembly 902. In certain embodiments, the user may install the sub-assembly 950 shortly before use. Installation of the sub-assembly 950 may puncture, displace, or otherwise overcome a seal provided in the reservoir assembly 900 thus placing the sub-assembly 950 into fluid communication with the interior volume of the reservoir assembly 900. Installation may also puncture, displace or otherwise overcome an optional seal provided in association with the port 990 of the base portion 904. This may place the sub-assembly 950 into fluid communication with various other pathways (see e.g. FIGS. 117-122) defined in the disposable housing assembly.

As shown, the example conduit sub-assembly 950 includes a base body 952 and a cover plate 914. The cover 914 may be laser welded to the base body 952 to enclose a recessed fluid pathway 956 defined in the base body 952. The cover plate 914 may also be attached in any other suitable manner. Alternatively the fluid pathway 956 may be entirely defined by the base body 952 and a cover plate 914 may not be included. Where a cover plate 914 is utilized, the cover plate 914 may include the recessed fluid pathway 956 instead of the base body 952. The flow path through the sub-assembly 950 may also be formed via a recessed fluid pathway 956 in both the base body 956 and the cover plate 914. A variable depth flow path similar to that described in relation to FIGS. 120-122 may also be included in some embodiments.

Figure 126:
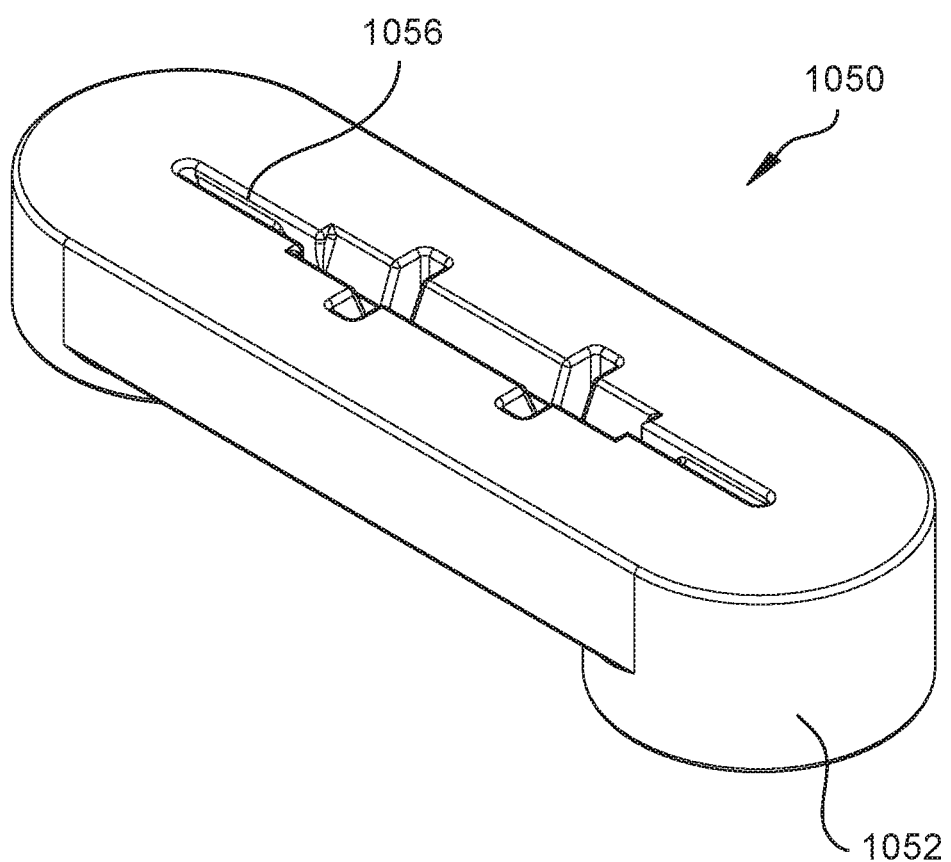

The base body 952 may have a shape which mimics the path of the flow path included in the sub-assembly 950. In the example embodiment, the flow path through the sub-assembly 950 as well as the base body 952 itself includes a curve. In other embodiments, and referring now to FIG. 126, the flow path 1056 of a conduit sub assembly 1050 may be substantially straight. The base body 1052 may be substantially straight as well. Flow paths which include multiple curved regions may also be used. In some examples, flow paths may include segments which are angled with respect to one another as opposed to connected by a curve.

The conduit sub-assembly 950 may include additional components. For example, the sub-assembly 950 may include one or more air traps 991. As best shown in FIG. 123, two air traps 991 are included in the conduit sub-assembly 950 in the example embodiment. The air traps 991 may include screens 954 which are assembled into wells in the base body 952. The air traps 991 may be similar to as described elsewhere in the specification. A conduit sub-assembly 950 may also include at least one needle 958. A needle 958 may be included in a connector interface which engages the outlet 940 of the port connector 920 of the reservoir assembly 900. When installed on the port connector 920, the needle of the sub-assembly may pierce a septum 962 included in the port connector 920 to establish fluid communication with the interior volume of the reservoir assembly 900. A needle 958 may also be included as part of a connector interface which engages port 990 of the base portion 904. The needle 958 may similarly pierce a septum to establish fluid communication between the sub-assembly 950 and the base portion 904 flow paths. In alternative embodiments, the port connector 920 may include a pin like those described in relation to FIGS. 18-21 or in any one or more of the applications and/or patents incorporated herein by reference. The sub-assembly 950 may include a port interface with a post including, but not limited to any of those described in any one or more of the applications and/or patents incorporated herein by reference.

Referring now also to FIGS. 127-132, in certain embodiments, a conduit sub-assembly 1150 which includes a plurality of base bodies 1152A, B connected together by tubing 1170 may be included. A first base body 1152A may serve as a connector which mates with a port connector 1120 which is included in a reservoir assembly (see, e.g. FIGS. 2-3). Upon mating, and referring primarily to FIG. 131, a needle 1158 in the first base body 1152A may penetrate a septum 1162. This may establish fluid communication between the interior volume of the reservoir assembly and the conduit sub-assembly 1150. In alternative embodiments, a pin and post type interaction may be used as described elsewhere herein.

As best shown in FIG. 131, the port connector 1120 may include an outlet 1140 and an inlet 1142 which may be placed in fluid communication with each other via a common fluid channel or chamber 1148. A fill port similar to those described elsewhere herein may also be included depending on the embodiment. The inlet 1142 may be recessed into a thin base of the port connector 1120. The outlet 1140 may be defined at a first end region of the port base portion 1122. The inlet 1142 may extend from this end region to the opposing end of the base portion 1122. The reservoir 1118 (shown in FIG. 131) may be heat bonded or otherwise secured to the port connector 1120. A protuberance 1128 in the sheeting 1116B is included to seal the common fluid channel 1148 when the sheeting 1116B has been bonded to the base portion 1122. The sheets 1116A, B of the reservoir 1118 may be bonded together around an intermediate portion of the base portion 1122. Since the base portion 1122 is relatively thin, the angle of the sheeting with respect to a horizontal midplane through the base portion 1122 may be relatively shallow. For example, the angle may be 25°-10°. In the specific embodiment shown in FIGS. 127-131, the angle would be about 13°. This may simplify joining of the sheeting 1116A, B of the reservoir 1118 and may help to minimize bunching or pocketing of fluid in the reservoir assembly when the reservoir assembly is emptied.

The first base body 1152A may include at least one catch feature 1172. In the example shown in FIGS. 127-132 two catch features 1172 are included. A greater or lesser number may be included in other embodiments. The catch features 1172 are shown as ramps which gradually thicken as distance from a bottom face 1174 of the first base body 1152A increases. The ramps terminate prior to the opposing face 1176 of the first base body 1152A creating a step. The port connector 1120 may include a catch engaging member 1178 for each of the catch features 1172 in the first base body 1152A. In the exemplary embodiment, the catch engaging members 1178 are cantilevered projections which include a fenestration 1180. As the first base body 1152A is advanced toward the port connector 1120, the ramps of the catch feature 1172 may contact the cantilevered projections of the engaging members 1178 once the first base body 1152A reaches a first position. Further advancement of the first base body 1152A to an intermediate position may cause the cantilevered projects to deflect outward. When the first base body 1152A has been advanced to a third, fully installed position, the end of the ramp may be within the fenestration 1180. Thus, the cantilevered projections of the catch engaging members 1178 may be free to displace inward out of their deflected state to a resting state. In this position, the step of the ramp may catch against the edge of the fenestration 1180 and may couple the first base member 1152A to the port connector 1120. In some embodiments, the interaction of catch feature(s) 1172 and catch engaging feature(s) 1178 may inhibit removal of the first base body 1152A so as to prevent reuse. In certain embodiment, upon advancement of the first base body 1152A to the third position, a tactile or audible click may be produced. This may act as feedback to the user allowing them to know that a coupling has been fully and robustly established.

The catch member 1172 and catch engaging member 1178 may disposed in the opposite configuration in certain embodiments. That is, the catch member 1172 may be disposed on a port connector 1120 and the catch engaging member 1178 may be disposed on the first base body 1152A. Other embodiments of port connectors described herein may include catch features 1172 or catch engaging members 1178 that cooperate with a suitable interface on the portion of the disposable housing assembly to which they are installed. The second base body 1152B may similarly include catch features 1172 or catch engaging members 1178 which couple to a cooperating feature in the disposable housing assembly 1178.

A catch member 1172 or catch engaging member 1178 may serve to generate a keyed relationship between the port connector and the portion of a disposable housing assembly to which it engages. This may dictate a prescribed installation orientation and prevent a reservoir assembly from being installed in an improper orientation. In certain embodiments, a keyed engagement between a port connector and the portion of a disposable housing assembly to which it is engaged may be present, but not necessarily include a latching or catch type engagement.

Referring now also to FIG. 132, the second base body 1152B may include a connector 1190. In the exemplary embodiment, the connector 1190 is a male connector which may fit into a corresponding female mating recess in a disposable housing assembly. The connector 1190 may be surrounded by one or more gasketing members 1192. In the example, two o-ring type gasketing members 1192 are depicted. The gasketing members 1192 help to form a fluid tight seal when the connector 1190 is brought into engagement with the disposable housing assembly.

Referring now also to FIG. 130, the first and second base body 1152A, B may include a cover plate 1114. A cover plate 1114 may be coupled (e.g. via laser weld) to each of first and second base bodies 1152A, B to form a sealed fluid pathway as described elsewhere herein. In other embodiments, fluid pathways included in the first and/or second bodies 1152A, B may be completely defined by the respective first or second body 1152A, B. The tubing 1170 connecting the first and second body 1170 may be attached to the first and second body 1152A, B in any suitable manner. Glue, epoxy, adhesive, solvent bonding, heat bonding, etc. may be used depending on the embodiment.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A reservoir assembly comprising:
   a reservoir; and
   a port connector comprising:
      a flange extending outward and mating to the reservoir;
      an inlet formed in the flange and extending from an interior volume of the reservoir;
      an outlet wherein fluid contained in the interior volume of the reservoir exits the reservoir, the inlet forming a channel having an open side extending to the outlet; and
      a filling port configured wherein the reservoir may be filled with a fluid.

2. The reservoir assembly of claim 1, wherein the reservoir is at least partially constructed of a flexible material.

3. The reservoir assembly of claim 1, wherein the reservoir is at least partially constructed of a rigid material.

4. The reservoir assembly of claim 1, wherein the reservoir is at least partially constructed of a flexible material and is at least partially constructed of a rigid material.

5. The reservoir assembly of claim 1, wherein the reservoir comprising a perimeter edge comprising at least one contoured segment.

6. The reservoir assembly of claim 1, wherein the reservoir comprising a perimeter edge comprising at least one round segment.

7. The reservoir assembly of claim 1, wherein the reservoir comprising a perimeter edge comprising at least one arcuate segment.

8. The reservoir assembly of claim 5, wherein at least a portion of the at least one contoured segment is defined by the port connector.

9. The reservoir assembly of claim 1, wherein at least a section of the port connector is substantially perpendicular to a top and a bottom side formed by the reservoir.

10. The reservoir assembly of claim 1, wherein the port connector further comprises a common fluid channel.

11. The reservoir assembly of claim 10, wherein the common fluid channel is an intermediary conduit between the inlet and the outlet.

12. The reservoir assembly of claim 10, wherein the common fluid channel is an intermediary conduit between the inlet, the outlet, and the filling port.

13. The reservoir assembly of claim 10, wherein fluid exiting the reservoir passes from the inlet, through the common fluid channel, and to the outlet.

14. The reservoir assembly of claim 1, further comprising a common fluid channel connecting the filling port and the inlet.

15. The reservoir assembly of claim 14, wherein the port connector further comprising a pin, wherein the pin blocks the outlet and at least partially extends into the common fluid channel.

16. The reservoir assembly of claim 15, wherein the pin is displaceable within the port connector.

17. The reservoir assembly of claim 16, wherein the pin selectively seals off fluid communications between the inlet and the outlet.

18. The reservoir assembly of claim 15, further comprising a stopper removably attached to the filling port.

19. The reservoir assembly of claim 15, wherein the pin is displaceable between a first position and a second position, the pin sealing the outlet in the first position, at least a portion of the pin in the common fluid channel in the second position.

20. The reservoir assembly of claim 18, wherein the port connector is configured to accept a fill nozzle at a first time and the stopper at a second time.

21. The reservoir assembly of claim 1, wherein the inlet defines a trough open on one side.

* * * * *